United States Patent
Mozaffari et al.

(10) Patent No.: US 12,070,505 B2
(45) Date of Patent: Aug. 27, 2024

(54) TARGETED PEPTIDE-DRUG CONJUGATES

(71) Applicant: Chapman University, Orange, CA (US)

(72) Inventors: Saghar Mozaffari, Orange, CA (US); David Salehi, Orange, CA (US); Parvin Mahdipoor, Orange, CA (US); Rakesh Tiwari, Orange, CA (US); Hamidreza Montazeri Aliabadi, Rancho Santa Margarita, CA (US); Keykavous Parang, Irvine, CA (US); Khalid Zoghebi, Orange, CA (US)

(73) Assignee: Chapman University, Orange, CA (US)

( * ) Notice: Subject to any disclaimer, the term of this patent is extended or adjusted under 35 U.S.C. 154(b) by 154 days.

(21) Appl. No.: 17/673,519

(22) Filed: Feb. 16, 2022

(65) Prior Publication Data
US 2022/0265839 A1 Aug. 25, 2022

Related U.S. Application Data

(60) Provisional application No. 63/149,771, filed on Feb. 16, 2021.

(51) Int. Cl.
*A61P 35/00* (2006.01)
*A61K 31/704* (2006.01)
*A61K 47/64* (2017.01)

(52) U.S. Cl.
CPC ............ *A61K 47/64* (2017.08); *A61K 31/704* (2013.01); *A61P 35/00* (2018.01)

(58) Field of Classification Search
None
See application file for complete search history.

(56) References Cited

PUBLICATIONS

Hall R, Alasmari A, Mozaffari S, Mahdipoor P, Parang K, Montazeri Aliabadi H. Peptide/Lipid-Associated Nucleic Acids (PLANAs) as a Multicomponent siRNA Delivery System. Mol Pharm. Mar. 1, 2021;18(3):986-1002. doi: 10.1021/acs.molpharmaceut.0c00969. Epub Jan. 26, 2021. PMID: 33496597. (Year: 2021).*
Aliabadi, H. M. et al., "Effective Response of Doxorubicin-Sensitive and -Resistant Breast Cancer Cells to Combinational SiRNA Therapy" J. Control. Release 2013, 172 (1), 219-228.
Chhikara, B. S. et al., "Critical Evaluation of Pharmaceutical Rational Design of Nano-Delivery Systems for Doxorubicin in Cancer Therapy."J. Mater. Nanosci. 2019, 6 (2), 47-66.
Kratz, F., "Doxo-Emch (INNO-206): The First Albumin-Binding Prodrug of Doxorubicin to Enter Clinical Trials" Expert Opinion on Investigational Drugs. 2007. https://doi.org/10.1517/13543784.16.6.855.
Mandal, D. et al., "Cell-Penetrating Homochiral Cyclic Peptides as Nuclear-Targeting Molecular Transporters" Angew. Chemie—Int. Ed. 2011, 50 (41), 9633-9637.
Nasrolahi Shirazi, A. et al., "Cyclic Peptide Containing Hydrophobic and Positively Charged Residues as a Drug Delivery System for Curcumin" Curr. Drug Deliv. 2016, 13 (3), 409-417.
Nasrolahi Shirazi, A. et al., "Design and Biological Evaluation of Cell-Penetrating Peptide-Doxorubicin Conjugates as Prodrugs" Mol. Pharm. 2013, 10 (2), 488-499.
Wang, Y. et al., "Synthesis and Preliminary Antitumor Activity Evaluation of a DHA and Doxorubicin Conjugate" Bioorganic Med. Chem. Lett. 2006, 16 (11), 2974-2977.

* cited by examiner

*Primary Examiner* — Thomas S Heard
(74) *Attorney, Agent, or Firm* — K&L Gates LLP; Louis C. Cullman; Michelle Glasky Bergman

(57) ABSTRACT

Provided herein are drug delivery systems comprising a peptide targeting agent and a pharmaceutical agent for delivery of chemotherapeutic agents. Also provided are methods of treating cancer comprising administration of the drug delivery system disclosed herein.

6 Claims, 36 Drawing Sheets
(29 of 36 Drawing Sheet(s) Filed in Color)

[(WR)₈WKβA]

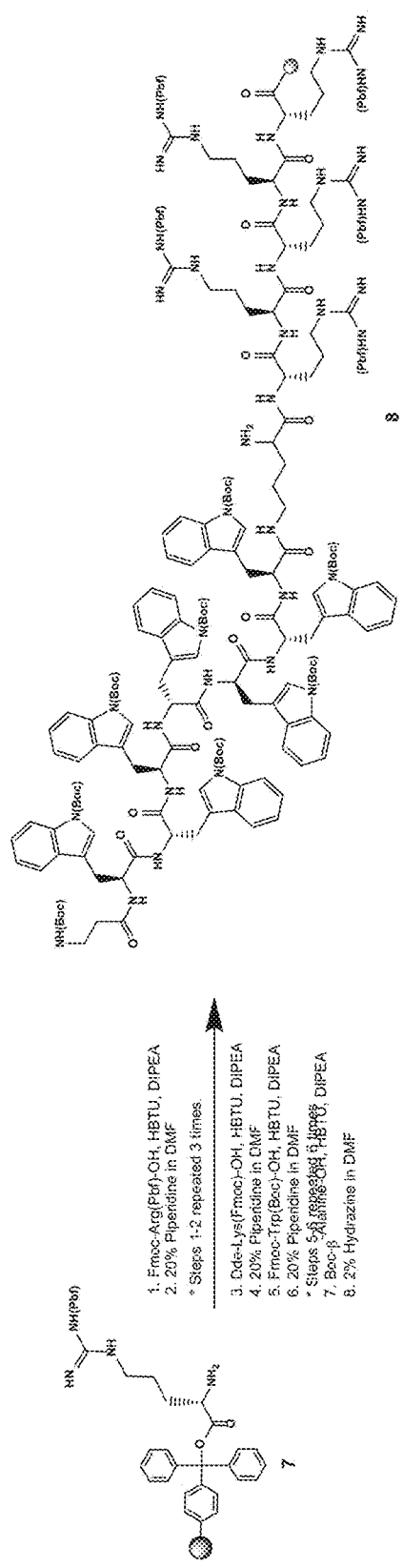
Figure 3 (Scheme 1)
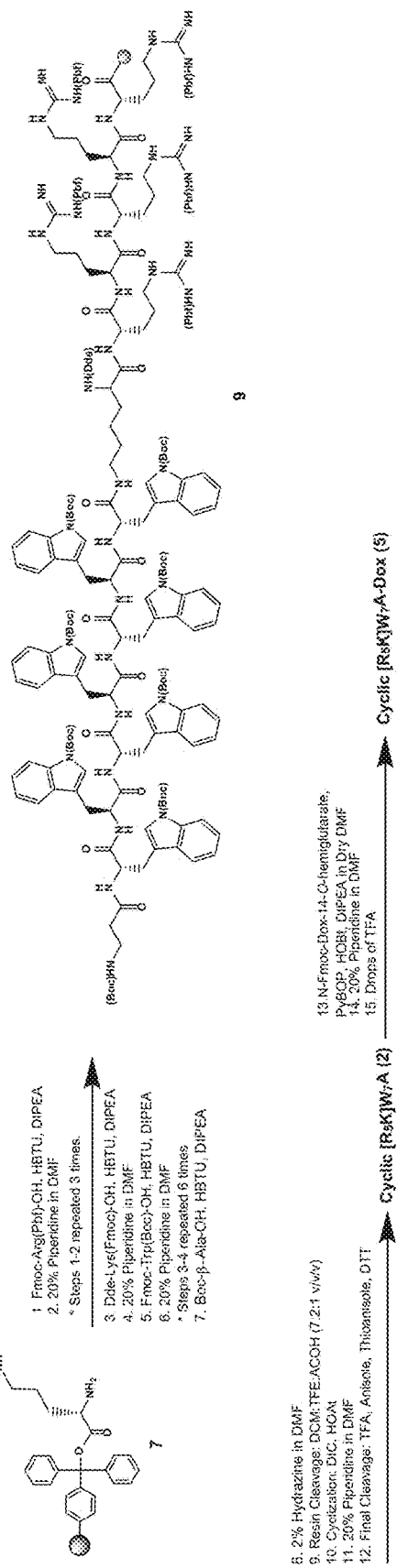
Figure 4 (Scheme 2)

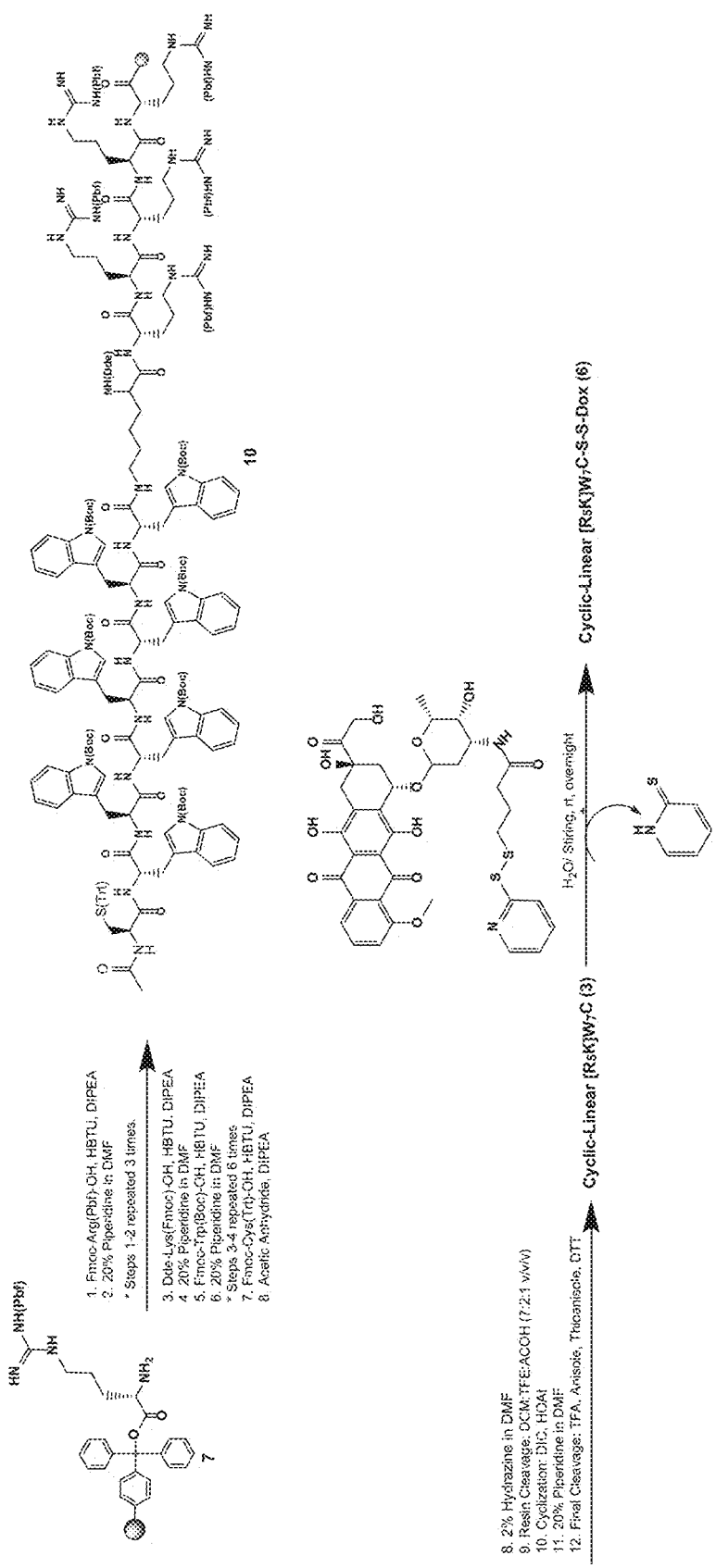
Figure 5 (Scheme 3)

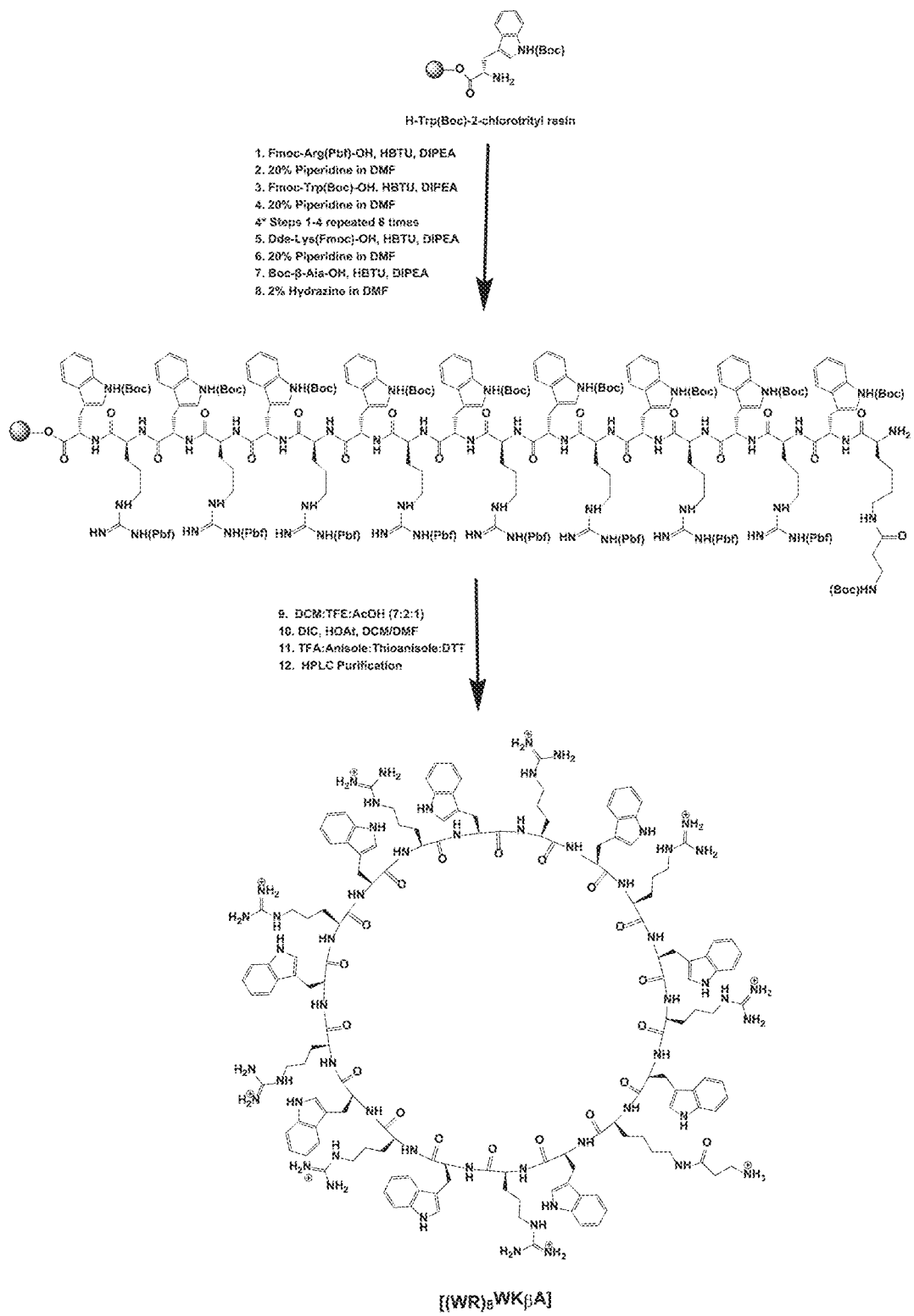
Figure 20 (Scheme 4)

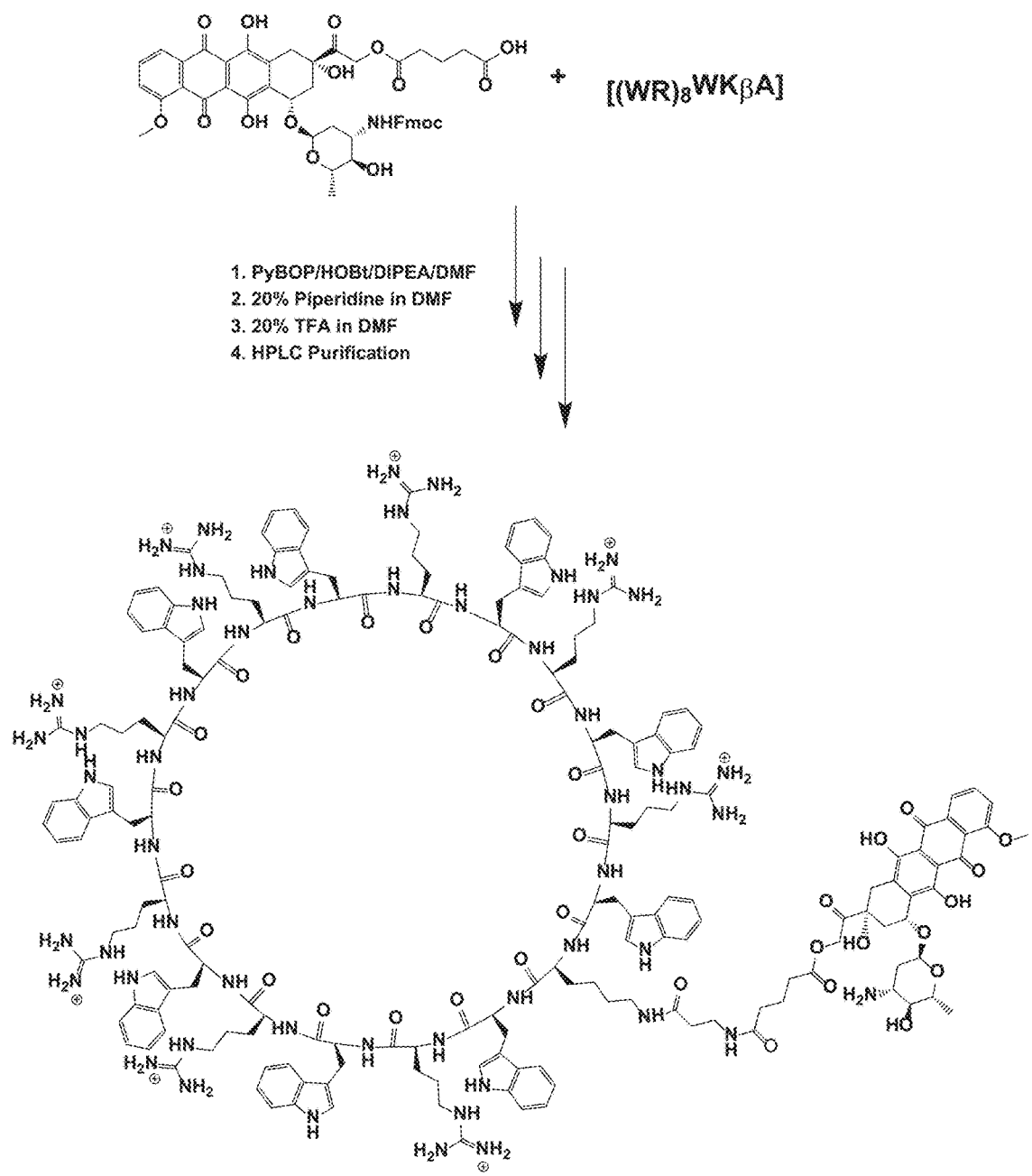
Figure 21 (Scheme 5)

TARGETED PEPTIDE-DRUG CONJUGATES

CROSS-REFERENCE TO RELATED APPLICATIONS

This application claims the benefit of U.S. Provisional Patent Application 63/149,771 filed Feb. 16, 2021, the entire contents of which is incorporated by reference herein.

FIELD

The present disclosure relates to delivery of chemotherapeutic drugs.

BACKGROUND

As a defense mechanism, cancer cells often develop resistance after initial exposure to several chemotherapeutic drugs. One of the major drawbacks limiting use of some chemotherapeutic agents application is acquired resistance developed by different tumor cells. Resistance to chemotherapeutics is known as multidrug resistance (MDR), and includes different mechanisms such as enhanced drug efflux out of the cells via ATP-binding cassette family (ABC) transporters, alteration of intracellular target molecules, activation of DNA repair enzymes, and modulation of apoptotic pathways. Among these, the overexpression of ATP-dependent efflux pump membrane proteins such as permeability glycoprotein (P-gp) is the most frequent. For example, intracellular doxorubicin accumulation is dependent on multiple factors, including cellular uptake, nuclear localization, cellular retention, and low efflux from the cells. P-gp overexpression efficiently removes doxorubicin and reduces its intracellular concentration.

Additionally, chemotherapeutic agents often exhibit undesirable pharmacokinetic properties such as low bioavailability, high volume of distribution, rapid blood excretion, and short half-life. Consequently, extremely high doses are required in cancer chemotherapy to elicit therapeutic effects, leading to the possibility of many side effects.

Chemical conjugation with a parent drug has been a widely used drug delivery system, and is referred to as a prodrug strategy. Anticancer drugs' biological activity and adverse events can be altered using drug delivery systems, modifying physicochemical properties such as lipophilicity and enhanced cellular uptake, and increasing the activity through chemical conjugation with different chemical moieties. Many techniques have been developed to improve drug delivery, such as using liposomes, gold nanoparticles, peptides, metal nanoparticles, and other covalent/noncovalent systems. Drug delivery systems can be used to overcome multidrug resistance proteins (MRPs) efflux pumps involved in chemotherapeutic agent resistance.

SUMMARY

Disclosed herein are drug delivery systems comprising a peptide targeting agent and a pharmaceutical agent. The peptide targeting agent comprises a cyclic peptide or a hybrid cyclic-linear peptide.

Thus, disclosed herein is a drug delivery system comprising a peptide targeting agent conjugated to a pharmaceutical agent, wherein the peptide targeting agent is a cyclic or hybrid cyclic linear peptide comprising tryptophan (W), arginine (R), and lysine (K) residues.

In some embodiments, the peptide targeting agent comprises (2)

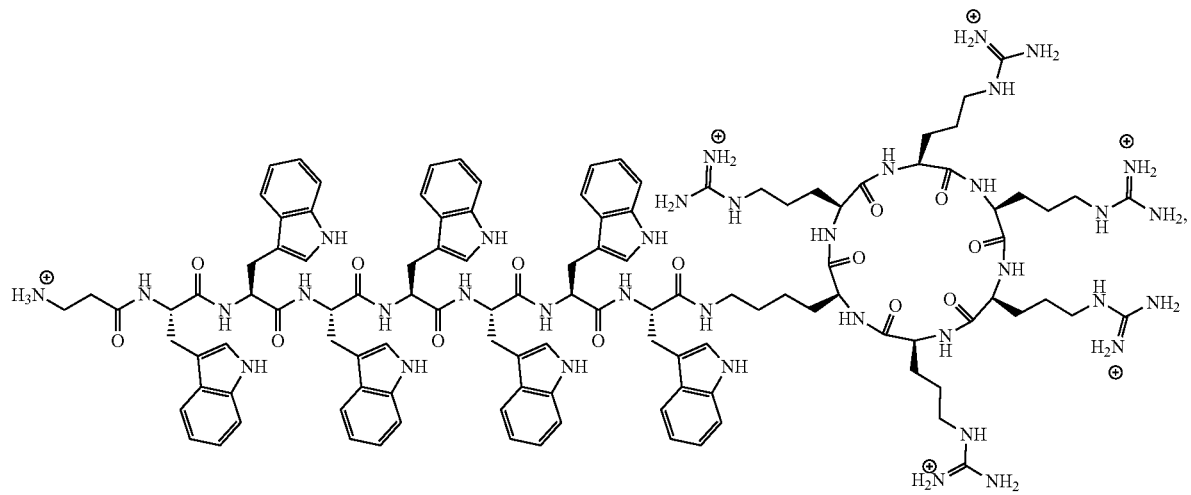

Cyclic-Linear [R₅K]W₇A

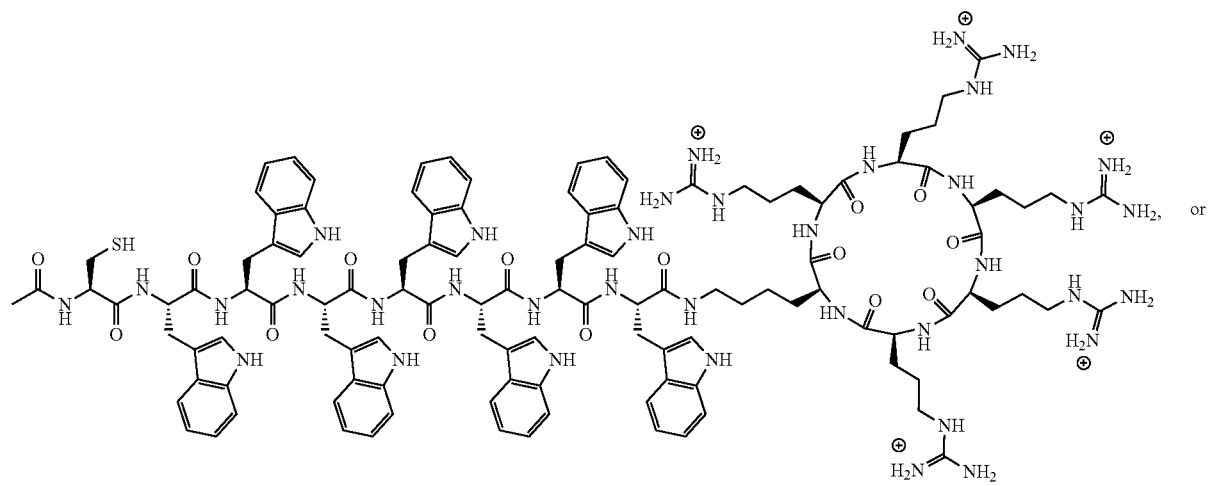
Cyclic-Linear [R₅K]W₇C
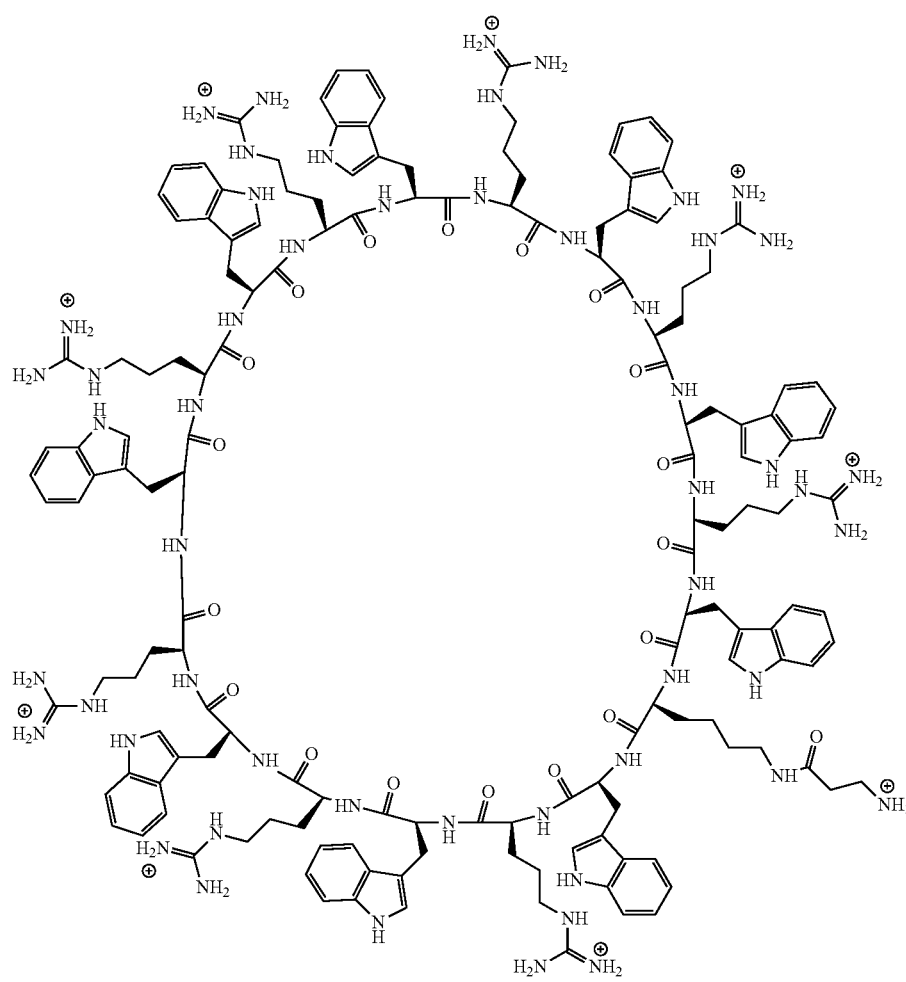
cyclic [(WR)₈WKβA]

In some embodiments, the peptide targeting agent comprises cyclic-linear [R$_5$K]W$_7$A. In some embodiments, the peptide targeting agent comprises cyclic-linear [R$_5$K]W$_7$C. In some embodiments, the peptide targeting agent comprises cyclic [(WR)$_8$WKβA].

In some embodiments of the drug delivery system, the pharmaceutical agent is selected from altretamine, bendamustine, busulfan, carboplatin, carmustine, chlorambucil, cisplatin, cyclophosphamide, dacarbazine, ifosfamide, lomustine, mechlorethamine, melphalan, oxaliplatin, temozolomide, thiotepa, trabectedin, streptozocin, azacitidine, 5-fluorouracil, 6-mercaptopurine, capecitabine, cladribine, clofarabine, cytarabine, decitabine, floxuridine, fludarabine, gemcitabine, hydroxyurea, methotrexate, nelarabine, pemetrexed, pentostatin, pralatrexate, thioguanine, trifluridine, tipiracil, daunorubicin, doxorubicin, epirubicin, idarubicin, valrubicin, bleomycin, dactinomycin, mitomycin-c, mitoxantrone, irinotecan, topotecan, etoposide, mitoxantrone, teniposide, cabazitaxel, docetaxel, nab-paclitaxel, paclitaxel, vinblastine, vincristine, vinorelbine, all-trans-retinoic acid, arsenic trioxide, asparaginase, eribulin, hydroxyurea, ixabepilone, mitotane, omacetaxine, pegaspargase, procarbazine, romidepsin, and vorinostat, and combinations thereof. In some embodiments, the chemotherapeutic drug is doxorubicin.

Also disclosed herein are methods of treating cancer comprising administering a drug delivery system disclosed herein to a subject in need thereof. In some embodiments, the drug delivery system comprises a peptide targeting agent conjugated to a pharmaceutical agent, wherein the peptide targeting agent is cyclic-linear [R$_5$K]W$_7$A, cyclic-linear [R$_5$K]W$_7$C, or cyclic [(WR)$_8$WKβA]. In some embodiments, the peptide targeting agent is cyclic-linear [R$_5$K]W$_7$A. In some embodiments, the peptide targeting agent is cyclic-linear [R$_5$K]W$_7$C. In some embodiments, the peptide targeting agent is cyclic [(WR)$_8$WKβA].

In some embodiments of the method of treating cancer, the pharmaceutical agent is a chemotherapeutic agent selected from altretamine, bendamustine, busulfan, carboplatin, carmustine, chlorambucil, cisplatin, cyclophosphamide, dacarbazine, ifosfamide, lomustine, mechlorethamine, melphalan, oxaliplatin, temozolomide, thiotepa, trabectedin, streptozocin, azacitidine, 5-fluorouracil, 6-mercaptopurine, capecitabine, cladribine, clofarabine, cytarabine, decitabine, floxuridine, fludarabine, gemcitabine, hydroxyurea, methotrexate, nelarabine, pemetrexed, pentostatin, pralatrexate, thioguanine, trifluridine, tipiracil, daunorubicin, doxorubicin, epirubicin, idarubicin, valrubicin, bleomycin, dactinomycin, mitomycin-c, mitoxantrone, irinotecan, topotecan, etoposide, mitoxantrone, teniposide, cabazitaxel, docetaxel, nab-paclitaxel, paclitaxel, vinblastine, vincristine, vinorelbine, all-trans-retinoic acid, arsenic trioxide, asparaginase, eribulin, hydroxyurea, ixabepilone, mitotane, omacetaxine, pegaspargase, procarbazine, romidepsin, and vorinostat, and combinations thereof. In some embodiments, the chemotherapeutic agent is doxorubicin.

In some embodiments, the cancer is acute lymphoblastic leukemia, acute myeloid leukemia, adrenocortical carcinoma, anal cancer, astrocytoma, bile duct cancer, bladder cancer, bone cancer, brain tumor, breast cancer, carcinoid tumor, carcinoma, cervical cancer, chronic lymphocytic leukemia, chronic myelogenous leukemia, myeloproliferative disorders, colorectal cancer, cutaneous T-cell lymphoma, endometrial cancer, ependymoma, esophageal cancer, Ewing's family of tumors, germ cell tumor, retinoblastoma; gallbladder cancer, gastric cancer, glioma, hairy cell leukemia, head and neck cancer; hepatocellular cancer, Hodgkin's lymphoma, islet cell carcinoma, Kaposi's sarcoma, kidney cancer, laryngeal cancer, lip and oral cavity cancer, liver cancer, lung cancer, non-small cell lung cancer, small cell lung cancer, lymphoblastic leukemia, lymphocytic leukemia, lymphoma, non-Hodgkin's lymphoma, Waldenstrom's macroglobulinemia, mesothelioma, malignant thymoma, medulloblastoma, melanoma, multiple endocrine neoplasia syndrome, multiple myeloma/plasma cell neoplasm, mycosis fungoides, myelodysplastic syndromes, myelogenous leukemia, myeloid leukemia, nasopharyngeal cancer, neuroblastoma, oral cancer, oropharyngeal cancer, osteosarcoma/malignant fibrous histiocytoma of bone, ovarian cancer, pancreatic cancer, parathyroid cancer, penile cancer, pheochromocytoma, pituitary tumor, prostate cancer, rectal cancer, renal cell cancer, retinoblastoma, rhabdomyosarcoma, salivary gland cancer, sarcoma, Sezary syndrome, skin cancer, soft tissue sarcoma, squamous neck cancer, testicular cancer, thymoma, thyroid cancer, trophoblastic tumor, urethral cancer, uterine sarcoma, vaginal cancer, vulvar cancer, or Wilms' tumor. In some embodiments, the cancer is breast cancer. In some embodiments, the cancer is a triple negative breast cancer.

In some embodiments, as a result of administration of the peptide-targeting agent/pharmaceutical agent conjugate, the cancer in the subject is treated.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 3. Synthesis of hybrid cyclic-linear [R$_5$K]W$_7$A (2) (Scheme 1).

FIG. 4. Synthesis of [R$_5$K]W$_7$A-Dox (5) (Scheme 2).

FIG. 5. Synthesis of [R$_5$K]W$_7$C—S—S-Dox (6) (Scheme 3).

FIG. 20. Synthesis of cyclic peptide [(WR)₈WKβA]. (Scheme 4)

FIG. 21. Synthesis of cyclic peptide [(WR)₈WKβA]-Dox conjugate. (Scheme 5)

FIG. 28A depicts a schematic representation of the possible susceptible bonds in [(WR)₈WKβA]-Dox conjugate. FIG. 28B depicts stability analysis of [(WR)₈WKβA]-Dox conjugate in human plasma. FIG. 28C depicts intracellular release of free Dox from [(WR)₈WKβA]-Dox conjugate.

DETAILED DESCRIPTION

Figure 1:
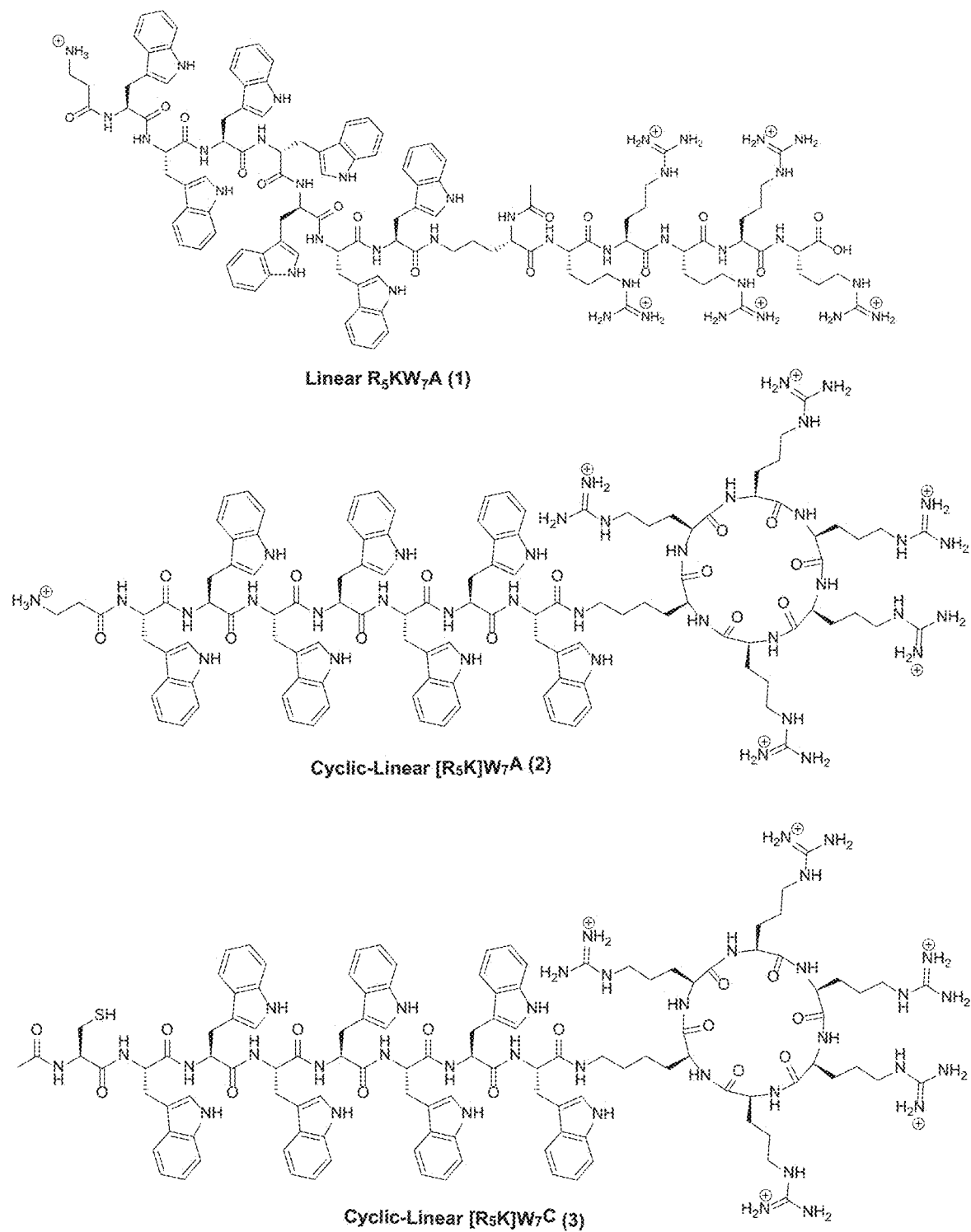
FIG. 1 depicts the structure of linear R$_5$KW$_7$A (1), cyclic-linear [R$_5$K]W$_7$A (2), cyclic-linear [R$_5$K]W$_7$C (3), and cyclic [(WR)$_8$WKβA].
Figure 1:
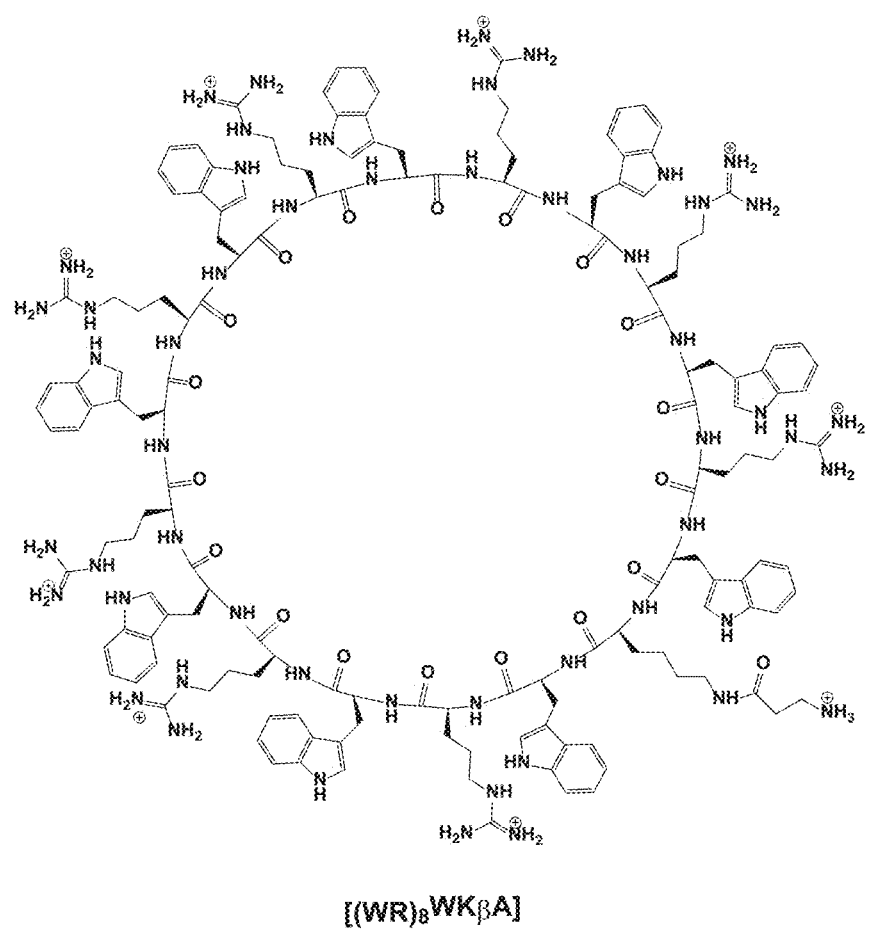

Disclosed herein are drug conjugates which demonstrate preferential uptake in cancer cells, even in cancers exhibiting multiple drug resistance.

Provided herein are drug delivery systems comprising a peptide targeting agent and a pharmaceutical agent for delivery of chemotherapeutic agents. Also provided are methods of treating cancer comprising administration of the drug delivery system disclosed herein.

The inherent resistance in cells that have never been exposed to anticancer drugs and the development of resistance after the initial response is one of the major limitations of cancer chemotherapy treatment. Several mechanisms of inherent and acquired multi-drug resistance have been studied, including alteration of the target protein and drug metabolism, decreased membrane permeability, and/or efflux pumping.

One of these chemotherapeutic agents, doxorubicin (Dox) is used for treatment of breast cancer, leukemia, and lymphoma treatment as an effective chemotherapeutic agent. However, Dox use is restricted due to inherent and acquired resistance and an 8-fold increase in the risk of potentially fatal cardiotoxicity and development of resistance associated with it. Doxorubicin Is a well-known, widely used anthracycline anticancer agent and has been approved by FDA for the treatment of leukemias, sarcomas, and lymphoma, as well as breast, gastric, ovarian, lung, and thyroid cancer. Dox acts through the inhibition of topoisomerase II (TOPO II)-DNA complex. DNA damage occurs by intercalating of Dox with the DNA double helix.

Moreover, the clinical application of Dox has demonstrated undesirable pharmacokinetic properties, such as low bioavailability, rapid distribution, and excretion of the drug, due to the hydrophilic nature and a high volume of distribution. Thus, a higher dose of Dox is required in cancer chemotherapy to achieve an adequate therapeutic effect. However, a higher cumulative dose leads to dose-dependent side effects, such as cardiotoxicity, nephrotoxicity, and extravasation.

Intracellular Dox accumulation is dependent on many parameters, such as cellular uptake, retention, re-localization, and efflux from the cell. Among these factors, uptake of Dox is affected by the efflux mechanism in a number of cancer cells such as ovarian carcinoma cells. And leads to the decreased levels of intracellular Dox. The overexpression of energy-dependent efflux pump integral membrane proteins such as P-glycoprotein (P-gp) removes drugs and thus reduces intracellular anticancer drug concentrations.

The biological efficacy and toxicity of an anticancer drug can be modified by using drug delivery systems and altering the physicochemical properties, such as lipophilicity, cellular uptake, and prolonging activity through chemical conjugation with various chemical moieties. One of the main applications of drug delivery systems is avoiding the P-gp and multidrug resistance proteins (MRPs) involved in drug efflux to overcome the resistance problem and P-gp-mediated drug efflux.

Chemical conjugation with a parent drug has been widely used as one of the drug delivery systems, which is referred to as a prodrug strategy. Several methods have been used to improve Dox delivery, including using gold nanoparticles, gold nanospheres, liposomes, peptides, and dendrimers. Several delivery systems of Dox have been explored, including metal nanoparticles, carbon nanotubes, dendrimers, liposomes, fullerenes, cyclic peptides, and other covalent/non-covalent systems).

Chemical conjugation of peptides with a parent drug has been widely used in Dox delivery. Conjugation of Dox with cell-penetrating peptides (CPPs) has been employed as one of the most effective methods to translocate the drug into various cell lines. For instance, Dox has been conjugated with different linear CPPs, including penetratin, tat, polyarginine, and maurocalcine. However, many of the above internalization mechanisms of CPP-based delivery systems involve endocytosis. Furthermore, many of these delivery systems did not resolve the cardiotoxicity of Dox. Finally, it is still challenging to develop efficient and safe prodrug carriers to enhance the delivery and retention of Dox into drug-resistant tumor cells. Thus, disclosed herein are systems for delivery of pharmaceutical agents, such as Dox, which overcomes these drawbacks.

Peptide Targeting Pharmaceutical Agent Conjugates

Disclosed herein are drug delivery systems comprising a peptide targeting agent and a pharmaceutical agent. The peptide targeting agent comprises a cyclic peptide or a hybrid cyclic-linear peptide.

In some embodiments, the pharmaceutical agent is a chemotherapeutic agent. In some embodiments, the chemotherapeutic agent is selected from altretamine, bendamustine, busulfan, carboplatin, carmustine, chlorambucil, cisplatin, cyclophosphamide, dacarbazine, doxorubicin, ifosfamide, lomustine, mechlorethamine, melphalan, oxaliplatin, temozolomide, thiotepa, trabectedin, streptozocin, azacitidine, 5-fluorouracil, 6-mercaptopurine, capecitabine, cladribine, clofarabine, cytarabine, decitabine, floxuridine, fludarabine, gemcitabine, hydroxyurea, methotrexate, nelarabine, pemetrexed, pentostatin, pralatrexate, thioguanine, trifluridine, tipiracil, daunorubicin, doxorubicin, epirubicin, idarubicin, valrubicin, bleomycin, dactinomycin, mitomycin-c, mitoxantrone, irinotecan, topotecan, etoposide, mitoxantrone, teniposide, cabazitaxel, docetaxel, nab-paclitaxel, paclitaxel, vinblastine, vincristine, vinorelbine, all-trans-retinoic acid, arsenic trioxide, asparaginase, eribulin, hydroxyurea, ixabepilone, mitotane, omacetaxine, pegaspargase, procarbazine, romidepsin, and vorinostat, and combinations thereof. In some embodiments, the chemotherapeutic agent is doxorubicin.

Cyclic and hybrid-cyclic peptides containing arginine (R) and tryptophan (W) residues are disclosed herein as non-covalent carriers for chemotherapeutic agents. In some embodiments, the peptides have the structure (2)

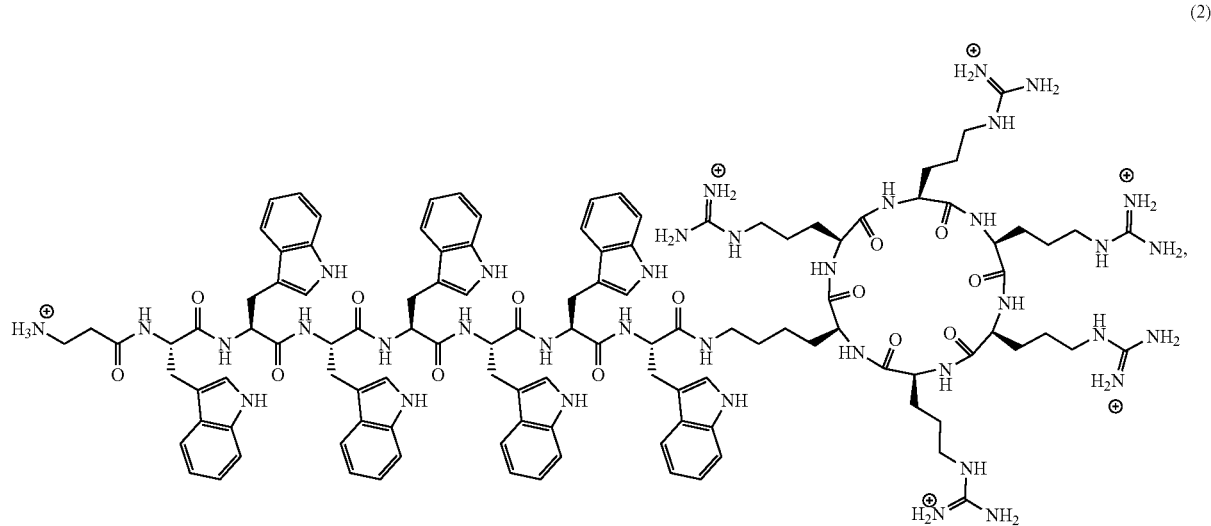

Cyclic-Linear [R$_5$K]W$_7$A

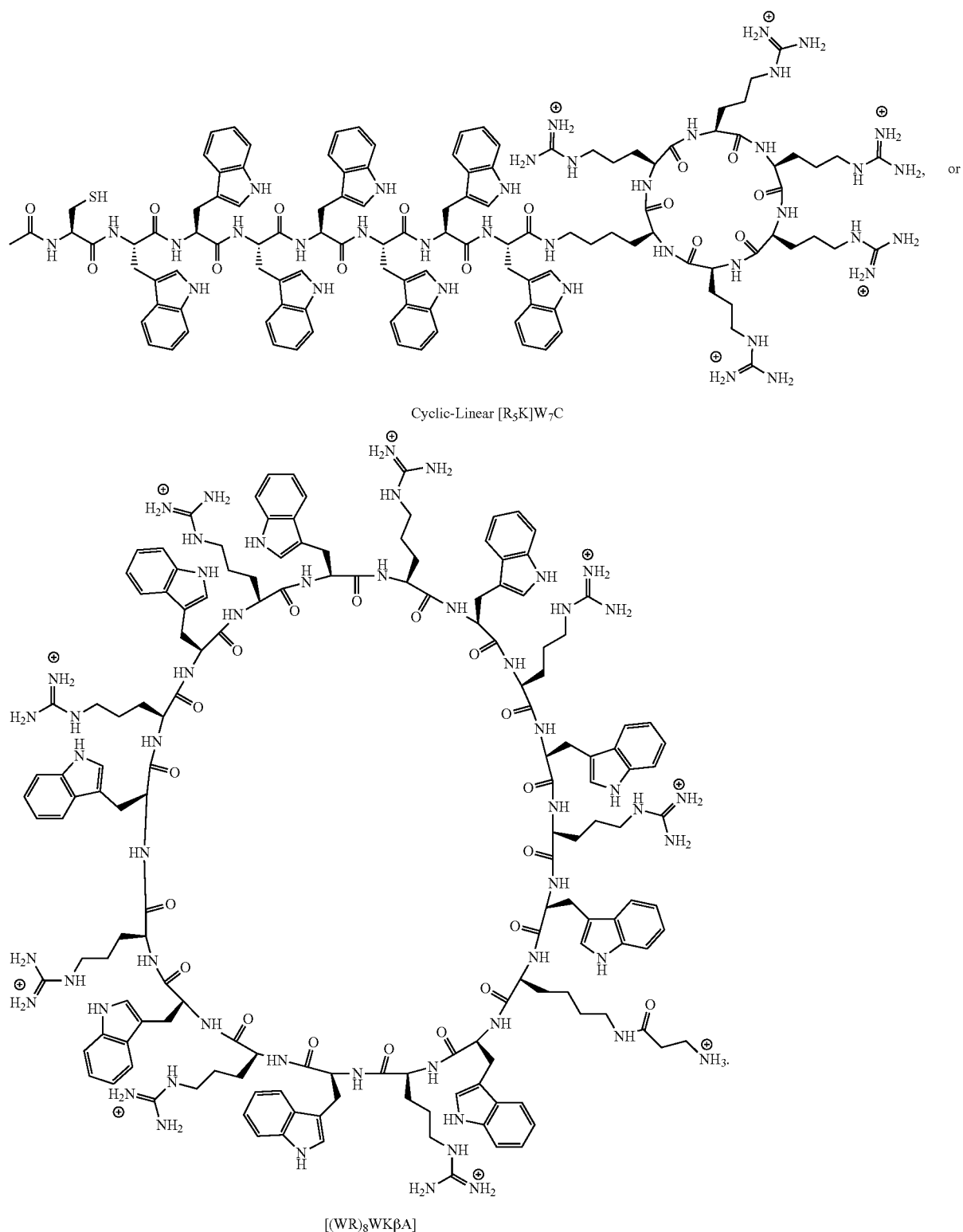

The conjugation of cyclic CPPs such as [WR]$_5$ with enhanced intracellular delivery of camptothecin (CPT), paclitaxel (PTX), Dox, and curcumin in different cancer cell lines with endosomal escape have been reported (El-Sayed, N. S. et al. *Molecules,* 24:1427, 2019; Nasrolahi Shirazi, A., et al. *Mol. Pharm.* 10:488-499, 2013; Nasrolahi Shirazi, A.; et al. *Curr. Drug. Deliv.* 13:409-417, 2016, which are incorporated herein by reference). Cyclic [W(RW)$_4$]-Dox enhanced the antiproliferative activity of Dox compared to the corresponding linear (RW)$_4$-Dox in human leukemia (CCRF-CEM), ovarian adenocarcinoma (SK-OV-3), colorectal carcinoma (HCT-116), and breast carcinoma (MDA-MB-468). [W(RW)$_4$]-Dox significantly improved the parent drug's cellular uptake and retention time in SK-OV-3 cancer cells. Flow cytometry analysis exhibited 3.3-3.6-fold higher cellular uptake of cyclic conjugate than parent Dox alone and the corresponding physical mixtures, linear (RW)$_4$+Dox, in SK-OV-3 and cyclic [W(RW)$_4$]+Dox cells after 24 h incubation (Mandal, D. et al. *Angew. Chem. Int. Ed.* 50:9633-9637, 2011, which is incorporated herein by reference).

Dox-thiol conjugates, thiolated doxorubicin (Dox-SH), thiol-reactive Dox-S—S-Pyr, and a Dox-S—S-cell-penetrating cyclic peptide, Dox-S—S—[C(WR)$_4$K] were synthesized, and their toxicity compared to Dox alone. All compounds showed high cellular uptake and were localized mostly in the nucleus in various cell lines. Further demonstrated was that Dox-S—S—[C(WR)$_4$K] exhibited less cytotoxicity in mouse myoblast cells in comparison to Dox.

Previous studies have demonstrated that hybrid cyclic-linear peptides [R$_5$K]W$_6$ and [R$_5$K]W$_5$ exhibited high efficiency to deliver siRNA into the MDA-MB-231 and MDA-MB-468 cells (Mozaffari, S. et al. *Polymers* 11:703, 2019, which is incorporated herein by reference). The hybrid cyclic-linear peptide [R$_5$K]W$_7$ significantly improved the uptake of a fluorescence-labeled phosphopeptide (F'-GpY-EEI), emtricitabine (F'-FTC), and stavudine (F'-d4T) (F'=5 (6)-carboxyfluorescein) by approximately 48-, 27-, and 36-fold, respectively, when compared with parent fluorescence-labeled compounds alone in CCRF-CEM cells after 3 h incubation.

Figure 2:
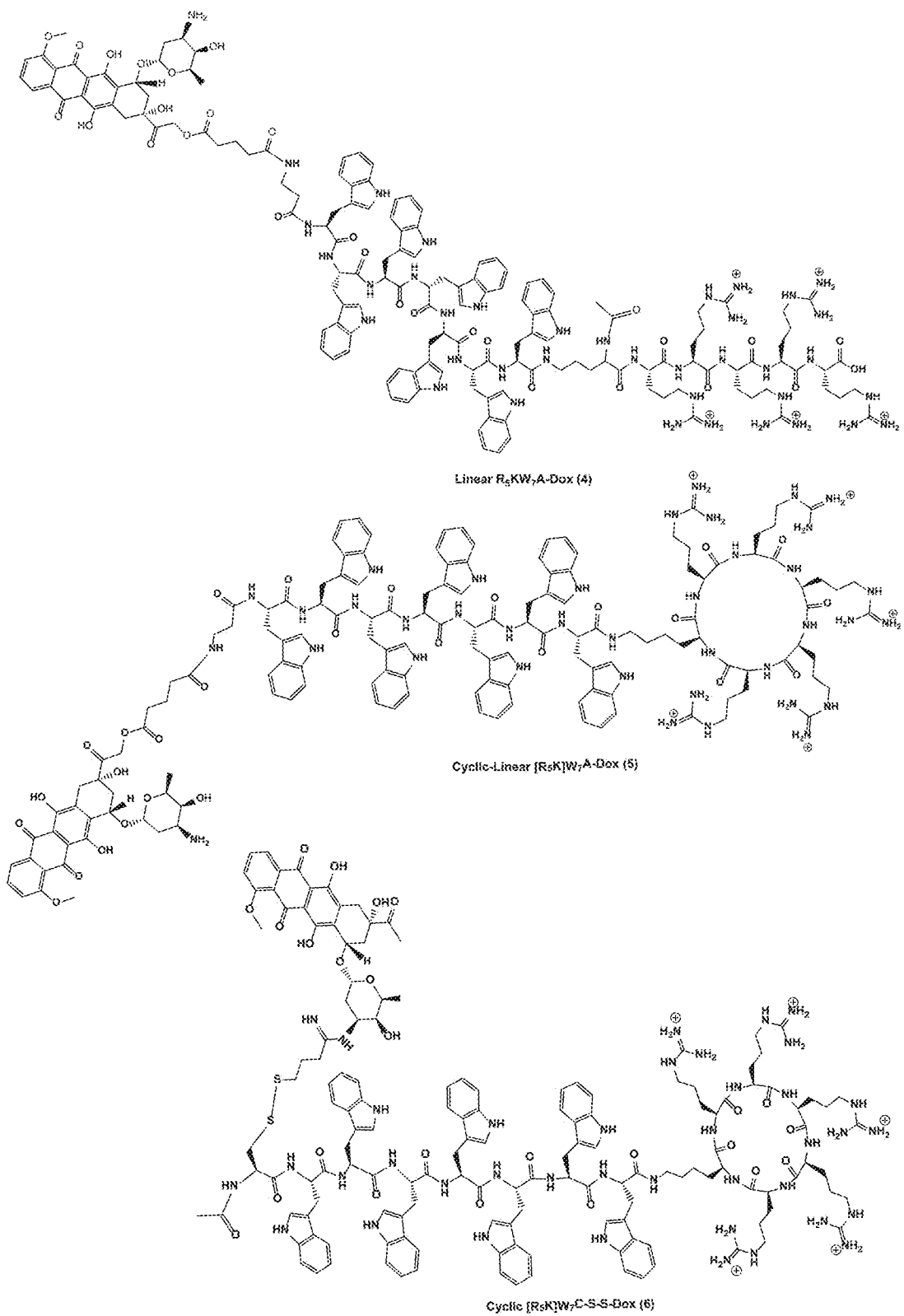
FIG. 2 depicts the structure of linear R$_5$KW$_7$A-Dox (4), cyclic-linear [R$_5$K]W$_7$A-Dox (5), and cyclic-linear [R$_5$K]W$_7$C—S—S-Dox (6) conjugates.

Also disclosed herein is the synthesis of linear R$_5$KW$_7$A (1), cyclic-linear [R$_5$K]W$_7$A (2), cyclic-linear [R$_5$K]W$_7$C (3), and cyclic [(WR)$_8$WKβA] peptides (FIG. 1). The peptides were used for the synthesis of peptide-drug conjugates (4-6, FIGS. 2 and 21) through an ester or disulfide linkage. The antiproliferative activities of the peptide-drug conjugates were evaluated in multiple cancer, normal, and drug-resistant cell lines.

Hybrid cyclic-linear peptide [R$_5$K]W$_7$A and linear peptide R$_5$KW$_7$A were conjugated with Dox through a glutarate linker to afford [R$_5$K]W$_7$A-Dox and R$_5$KW$_7$A-Dox conjugates to generate Dox derivatives. Alternatively, [R$_5$K]W$_7$C was conjugated with Dox via a disulfide linker to generate [R$_5$K]W$_7$C—S—S-Dox conjugate, where S—S is a disulfide bond. Comparative antiproliferative assays between conjugates [R$_5$K]W$_7$A-Dox, [R$_5$K]W$_7$C—S—S-Dox, linear R$_5$KW$_7$A-Dox, the corresponding physical mixtures of the peptides, and Dox were performed. [R$_5$K]W$_7$A-Dox conjugate was 2-fold more efficient than R$_5$KW$_7$A-Dox, and [R$_5$K]W$_7$C—S—S-Dox conjugates in inhibiting the cell proliferation of human leukemia cells (CCRF-CEM). Therefore, hybrid cyclic-linear [R$_5$K]W$_7$A-Dox conjugate was selected for further studies and inhibited the cell viability of CCRF-CEM (84%), ovarian adenocarcinoma (SK-OV-3, 39%), and gastric carcinoma (AGS, 73%) at a concentration of 5 μM after 72 h of incubation, which was comparable to Dox (5 μM) efficacy (CCRF-CEM (85%), SK-OV-3 (33%), and AGS (87%)). While [R$_5$K]W$_7$A-Dox had a significant effect on the viability of cancer cells, it exhibited minimal cytotoxicity to normal kidney (LLC-PK1, 5-7%) and heart cells (H9C2, <9%) at concentrations of 5-10 μM (compared to free Dox at 5 μM that reduced the viability of kidney and heart cells by 85% and 44%, respectively). The fluorescence microscopy images were consistent with the cytotoxicity studies, indicating minimal uptake of the cyclic-linear [R$_5$K]W$_7$A-Dox (5 μM) in H9C2 cells. In comparison, Dox (5 μM) showed significant uptake, reduced cell viability, and changed the morphology of the cells after 24 h. [R$_5$K]W$_7$A-Dox showed 16-fold and 9.5-fold higher activity against Dox-resistant cells MDA231R and MES-SA/MX2 (lethal dose for 50% cell death or LC$_{50}$ of 2.3 and 4.3 μM, respectively) compared to free Dox (LC$_{50}$ of 36 to 41 μM, respectively). These data, along with the results obtained from the cell viability tests, indicate comparable efficiency of [R$_5$K]W$_7$A-Dox to free Dox in leukemia, ovarian, and gastric cancer cells, significantly higher efficiency in Dox-resistant cells, and significantly reduced toxicity in normal kidney LLC-PK1 and heart H9C2 cells. A number of endocytosis inhibitors did not affect the cellular uptake of [R$_5$K]W$_7$A-Dox.

Also disclosed herein is the preparation of an amphiphilic cyclic peptide to yield [(WR)$_8$WKβA]-drug conjugate. The peptide-drug conjugate was designed to improve cellular uptake, prolong biological activity, and overcome intrinsic cellular efflux of the pharmaceutical agent. The antiproliferative activity of the peptide-Dox conjugate was evaluated in multiple cancer and Dox-resistant cell lines. The cellular and mechanism of uptake were investigated in the presence of endocytosis inhibitors. Cellular hydrolysis and release of free Dox were evaluated in the human leukemia (CCRF-CEM) cell line. Antiproliferative assays were performed in different cancer cell lines using the conjugate and the corresponding physical mixture of the peptide and Dox to evaluate the effectiveness of synthesized conjugate compared to the parent drug alone. [(WR)$_8$WKβA]-Dox conjugate showed higher antiproliferative activity at 10 μM and 5 μM than Dox alone at 5 μM. The conjugate inhibited the cell viability of ovarian adenocarcinoma (SK-OV-3) by 59% and the triple-negative breast cancer cells MDA-MB-231 and MCF-7 by 71% and 77%, respectively, at a concentration of 5 μM after 72 h of incubation. In contrast, Dox inhibited the proliferation of SK-OV-3, MDA-MB-231, and MCF-7 by 35%, 63%, and 57%, respectively. Furthermore, [(WR)$_8$WKβA]-Dox conjugate (5 μM) inhibited the cell viability of Dox-resistant cells (MES-SA/MX2) by 92%, while the viability of cells incubated with free Dox was only 15% at 5 μM. Confocal microscopy images confirmed the ability of both Dox conjugate and the physical mixture of the peptide with the drug to deliver Dox through an endocytosis-independent pathway, as the uptake was not inhibited in the presence of endocytosis inhibitors. The stability of Dox conjugate was observed at different time intervals using analytical HPLC when the conjugate was incubated with 25% human serum. Half-life (t$_{1/2}$) for [(WR)$_8$WKβA]-Dox conjugate was (~6 h), and more than 80% of the conjugate was degraded at 12 h. The release of free Dox was assessed intracellularly using the CCRF-CEM cell line. Approximately 100% of free Dox was released from the conjugate intracellularly within 72 h. These data confirm the ability of the cyclic cell-penetrating peptide containing tryptophan and arginine residues as an efficient tool for delivery of chemotherapeutic agents, such as Dox, and for overcoming resistance to chemotherapeutic agents.

Treatment

Examples of cancers which can be treated by the disclosed methods include acute lymphoblastic leukemia, acute myeloid leukemia, adrenocortical carcinoma, anal cancer, astrocytoma, bile duct cancer, bladder cancer, bone cancer, brain tumor, breast cancer, carcinoid tumor, carcinoma, cervical cancer, chronic lymphocytic leukemia, chronic myelogenous leukemia, myeloproliferative disorders, colorectal cancer, cutaneous T-cell lymphoma, endometrial cancer, ependymoma, esophageal cancer, Ewing's family of tumors, germ cell tumor, retinoblastoma; gallbladder cancer, gastric cancer, glioma, hairy cell leukemia, head and neck cancer; hepatocellular cancer, Hodgkin's lymphoma, islet cell carcinoma, Kaposi's sarcoma, kidney cancer, laryngeal cancer, lip and oral cavity cancer, liver cancer, lung cancer, non-small cell lung cancer, small cell lung cancer, lymphoblastic leukemia, lymphocytic leukemia, lymphoma, non-Hodgkin's lymphoma, Waldenstrom's macroglobulinemia, mesothelioma, malignant thymoma, medulloblastoma, melanoma, multiple endocrine neoplasia syndrome, multiple myeloma/plasma cell neoplasm, mycosis fungoides, myelodysplastic syndromes, myelogenous leukemia, myeloid leukemia, nasopharyngeal cancer, neuroblastoma, oral cancer, oropharyngeal cancer, osteosarcoma/malignant fibrous histiocytoma of bone, ovarian cancer, pancreatic cancer, parathyroid cancer, penile cancer, pheochromocytoma, pituitary tumor, prostate cancer, rectal cancer, renal cell cancer, retinoblastoma, rhabdomyosarcoma, salivary gland cancer, sarcoma, Sezary syndrome, skin cancer, soft tissue sarcoma, squamous neck cancer, testicular cancer, thymoma, thyroid cancer, trophoblastic tumor, urethral cancer, uterine sarcoma, vaginal cancer, vulvar cancer, and Wilms' tumor. In certain embodiments, the cancer is breast cancer. In some embodiments, the cancer is a triple negative breast cancer. Some embodiments specifically include one or more of these cancers. Other embodiments specifically exclude one or more of these cancers.

As used herein, the terms "treatment," "treating," and the like refer to obtaining a desired pharmacologic and/or physiologic effect. This may be observed directly as a slowing of tumor growth, stabilization of disease, or a partial or complete response (that is, tumor regression or elimination of tumors), or extended overall or disease-free survival. Treatment may also be observed as an amelioration or reduction of symptoms related to the underlying cancer. However, as cancer treatment, the disclosed embodiments' aim and mechanism is directed to inhibiting, stabilizing, or reducing tumor growth (including metastases), or partially or completely eliminating tumors, or extending overall or disease-free survival; effects on other cancer symptoms are secondary. Direct treatment of such other symptoms (for example, pain, nausea, loss of appetite, etc.) is not within the scope of treating cancer as used herein. That is, treating a symptom, for example, cachexia in a cancer patient is not treating cancer. However, an agent that treats cancer (e.g., has an impact on the growth and/or spread of cancer) may also ameliorate a symptom, such as cachexia, either indirectly, through its effect on the cancer, or directly, through a pleiotropic effect. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of a composition disclosed herein to elicit a desired response in the individual.

However, the dose administered to a mammal, particularly a human, in the context of the present methods, should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

To benefit from the combined effect of targeted peptide-drug conjugates disclosed herein, embodiments include methods of treatment comprising or consisting of administering a targeted peptide-drug conjugates to a patient having cancer.

In various embodiments the herein disclosed treatments may be applied as a primary therapy, as a debulking therapy prior to surgical removal of tumor, or as an adjuvant therapy subsequent to any mode of primary therapy (especially surgery) to address residual disease and/or lower the risk of recurrent cancer.

In some embodiments the patient having cancer has not been previously treated with the conjugated pharmaceutical agent. In some embodiments the patient has been previously treated with the conjugated pharmaceutical agent and has achieved stable disease or a partial response (in some embodiments, as defined by RECIST or iRECIST criteria)—that is, the cancer is sensitive to the conjugated pharmaceutical agent.

Therapeutic efficacy can be monitored by periodic assessment of treated patients. For repeated administrations over several days or longer, the treatment can be repeated until a desired suppression of disease or disease symptoms occurs. However, other dosage regimens may be useful and are within the scope of the present disclosure.

The effectiveness of cancer therapy is typically measured in terms of "response." The techniques to monitor responses can be similar to the tests used to diagnose cancer such as, but not limited to:
  A lump or tumor involving some lymph nodes can be felt and measured externally by physical examination.
  Some internal cancer tumors will show up on an x-ray or CT scan and can be measured with a ruler.
  Blood tests, including those that measure organ function can be performed.

A tumor marker test can be done for certain cancers.

Regardless of the test used, whether blood test, cell count, or tumor marker test, it is repeated at specific intervals so that the results can be compared to earlier tests of the same type.

Response to cancer treatment is defined several ways:

Complete response—all of the cancer or tumor disappears; there is no evidence of disease. Expression level of tumor marker (if applicable) may fall within the normal range.

Partial response—the cancer has shrunk by a percentage but disease remains. Levels of a tumor marker (if applicable) may have fallen (or increased, based on the tumor marker, as an indication of decreased tumor burden) but evidence of disease remains.

Stable disease—the cancer has neither grown nor shrunk; the amount of disease has not changed. A tumor marker (if applicable) has not changed significantly.

Disease progression—the cancer has grown; there is more disease now than before treatment. A tumor marker test (if applicable) shows that a tumor marker has risen.

Other measures of the efficacy of cancer treatment include intervals of overall survival (that is time to death from any cause, measured from diagnosis or from initiation of the treatment being evaluated)), cancer-free survival (that is, the length of time after a complete response cancer remains undetectable), and progression-free survival (that is, the length of time after disease stabilization or partial response that resumed tumor growth is not detectable).

There are two standard methods for the evaluation of solid cancer treatment response with regard to tumor size (tumor burden), the WHO and RECIST standards. These methods measure a solid tumor to compare a current tumor with past measurements or to compare changes with future measurements and to make changes in a treatment regimen. In the WHO method, the solid tumor's long and short axes are measured with the product of these two measurements is then calculated; if there are multiple solid tumors, the sum of all the products is calculated. In the RECIST method, only the long axis is measured. If there are multiple solid tumors, the sum of all the long axes measurements is calculated. However, with lymph nodes, the short axis is measured instead of the long axis. There is a variation of the RECIST method for immunotherapies (iRECIST) which takes into account distinctive behaviors linked to these types of therapeutics, such as delayed responses after pseudoprogression. Both the RECIST 1.1 guidelines and the iRecist guidelines are incorporated by reference herein in their entirety.

In some embodiments of the herein disclosed methods, the tumor burden of a treated patient is reduced by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 1-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 5-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 10-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In yet other embodiments, the subject has a sustained remission of at least 6 months, at least 7 months, at least 8 months, at least 9 months, at least 10 months, at least 11 months, at least 12 months, at least 14 months, at least 16 months, at least 18 months, at least 20 months, at least 22 months, at least 24 months, at least 27 months, at least 30 months, at least 33 months, at least 36 months, at least 42 months, at least 48 months, at least 54 months, or at least 60 months or more.

While a cancer treatment may reduce or treat associated symptoms, treating symptoms associated with cancer, is not treating cancer if there is no expectation that tumor will be reduced or eliminated or their growth or spread will be inhibited.

Toxicities and adverse events are sometimes graded according to a 5 point scale. A grade 1 or mild toxicity is asymptomatic or induces only mild symptoms; may be characterized by clinical or diagnostic observations only; and intervention is not indicated. A grade 2 or moderate toxicity may impair activities of daily living (such as preparing meals, shopping, managing money, using the telephone, etc.) but only minimal, local, or non-invasive interventions are indicated. Grade 3 toxicities are medically significant but not immediately life-threatening; hospitalization or prolongation of hospitalization is indicated; activities of daily living related to self-care (such as bathing, dressing and undressing, feeding oneself, using the toilet, taking medications, and not being bedridden) may be impaired. Grade 4 toxicities are life-threatening and urgent intervention is indicated. Grade 5 toxicity produces an adverse event-related death.

EXAMPLES

Example 1. Design and Application of Hybrid Cyclic-Linear Peptide-Drug Conjugates Materials All protected amino acids and resins were purchased from AAPPTEC. Doxorubicin was purchased from LC Laboratories. All the other chemicals reagents were purchased from MilliporeSigma. Medium (RPMI-1640), fetal bovine serum, and all other cell biology reagents were purchased from Wilkem Scientific and Fisher Scientific. 4',6'-Diamidino-2-phenylindole (DAPI) was purchased from Vector Laboratories. The final products were characterized by high-resolution matrix-assisted laser desorption/ionization time-of-flight (MALDI-TOF, GT 0264) from Bruker Inc. with α-cyano-4-hydroxycinnamic acid as a matrix. The final crude products were purified by a reversed-phase HPLC from Shimadzu (LC-20AP) by using a gradient system of water and acetonitrile and a reversed-phase preparative column (XBridge BEH130 Prep $C_{18}$ from Waters Human leukemia cell line (CCRF-CEM, ATCC No. CCL-119), human ovarian adenocarcinoma cells (SKOV-3, ATCC No. HTB-77) cells, kidney cell line (LLC-PK1, ATCC No. CRL-101), gastric adenocarcinoma cells (AGS, ATCC No. CRL-1739), uterine sarcoma cells (MES-SA/MX2, ATCC No. CRL-2274), and heart/myocardium cells (H9C2, ATCC No. CRL 1446) were purchased from American Type Culture Collection (ATCC). Cell Counting 8 (CCK8) KIT was purchased from Biotool (also known as WST-8). VECTASHIELD VIBRANCE with DAPI (used to stain the cell nuclei) was obtained from Vector Laboratories. CellTiter 96® AQueous MTS Reagent Powder was obtained from Promega. The MTS reagent is composed of a tetrazolium derivative (3-(4,5-dimethylthiazol-2-yl)-5-(3-carboxymethoxyphenyl)-2-(4-sulfophenyl)-2H-tetrazolium (named MTS) and phenazine ethosulfate (PES) and was used for the cell-based proliferation studies. All the materials for cell culture studies were purchased from Fischer Scientific.

Peptide Synthesis.

Synthesis of Linear $R_5KW_7A$ Peptide (1). Fmoc-Arg (Pbf)-OH, Fmoc-Trp(Boc)-OH, Boc-β-Ala-OH, and Fmoc-Lys(Dde)-OH were used as building block amino acids in the peptide synthesis. The preloaded resin, H-Arg(Pbf)-2-chlorotrityl (0.44 meq/g, 0.4 mmol, 905 mg), was swelled in N,N-dimethylformamide (DMF) under dry nitrogen gas (3×15 min). After filtration of the solvent, the next Fmoc-protected amino acid (3 equiv.) was conjugated to the free N-terminal in the presence of 2-(1H-benzotriazol-1-yl)-1,1,3,3-tetramethyluronium hexafluorophosphate (HBTU) (3 equiv.) as the coupling reagent and N,N-diisopropylethylamine (DIPEA) (6 equiv.) as the base in DMF by agitating under dry nitrogen gas for 1.5 h. After the completion of the coupling, the reaction solution was filtered off. The resin was washed subsequently with DMF (15 mL, 2×5 min). Fmoc deprotection was conducted in the presence of piperidine in DMF (10 mL, 2×15 min, 20% v/v). The reaction solution was filtered off, and the resin was washed with DMF (15 mL, 2×5 min). The subsequent amino acids were coupled and deprotected in a similar manner. After the final coupling with Boc-β-Ala-OH, the resin was washed with DMF (3×25 mL, each time 5 min). Then, the Dde group at the N-terminal of lysine was deprotected by using hydrazine monohydrate (2% v/v) solution in DMF (3×20 mL, each time 10 min), and the amino group of lysine was capped using acetic anhydride (3 equiv., 300 µL) and DIPEA (6 equiv.) for 1 h. After the formation of the linear peptides was confirmed by MALDI mass spectroscopy, the freshly prepared cleavage cocktail (Reagent R, trifluoroacetic acid (TFA), anisole, thioanisole, 9:1:2 (v/v/v); and 50 mg of DTT, 20 mL) was added to the mixture that was stirred at room temperature for 4 h. Cold diethyl ether was added to the crude peptide product to precipitate. After centrifugation, the crude peptide was purified using reversed-phase HPLC, and lyophilized.

$R_5KW_7A$ (1): MALDI-TOF (m/z): $C_{117}H_{149}N_{37}O_{16}$, calculated: 2328.1983. found: 2350.1995 $[M+Na]^+$.

Synthesis of cyclic-linear $[R_5K]W_7A$ (2) and $[R_5K]W_7C$ (3) Peptides. Fmoc-Arg(Pbf)-OH, Fmoc-Trp(Boc)-OH, and Dde-Lys(Fmoc)-OH were used as building block amino acids in the synthesis of these peptides. H-Arg (Pbf)-2-chlorotrityl (0.44 meq/g, 905 mg) resin was first swelled in DMF under dry nitrogen (15 min×3). After filtering the solvent, the next Fmoc protected amino acid (3 equiv.) was coupled to the free N-terminal in the presence of HBTU (3 equiv.) as the coupling reagent and DIPEA (6 equiv.) as the base in DMF by agitating under dry nitrogen gas for 1.5 h. After the completion of the coupling, the reaction mixture was filtered off. The resin was washed subsequently with DMF (15 mL, 2×5 min). Fmoc deprotection was conducted by using piperidine in DMF (10 mL, 2×15 min, 20% v/v). After the reaction mixture was filtered off, the resin was washed subsequently with DMF (15 mL, 2×5 min). The next amino acids were coupled and deprotected using a similar procedure. After conjugation of lysine residue containing the protected amino group with Dde, the Fmoc of the side chain protecting group of lysine was removed in the presence of piperidine in DMF (20% v/v). Coupling of Fmoc-Trp(Boc)-OH on the side chain of lysine was continued. After coupling of Boc-(β-Ala)-OH in case of $[R_5K]W_7A$ and Fmoc-Cys (Trt)-OH in case of $[R_5K]W_7C$ followed by capping the amino group of cysteine with acetic anhydride and DIPEA, the Dde group of lysine residue was removed in the presence of hydrazine in DMF (2% v/v). The resin was washed with DMF (15 mL, 2×5 min) and then methanol (15 mL, 5 min). Next, the resin was dried under low pressure for 4 h. The freshly prepared resin cleavage cocktail, dichloromethane:trifluoroethanol:acetic acid (DCM:TFE:AcOH; 35 mL:10 mL:5 mL) was added to the resin. The mixing was continued for 3 h. The filtrate was evaporated under vacuum. To remove the remaining acetic acid from the mixture, hexane (2×20 mL) and DCM (2×15 mL) were added to the residue. The crude material was solidified as a white solid. The crude peptide was dried under vacuum overnight.

After the formation of the linear peptides was confirmed by MALDI mass spectroscopy, the crude protected peptides were used directly for the cyclization reaction. The cyclization occurred between the free $NH_2$ side of the lysine and the free COOH side of arginine. A mixture of anhydrous DMF (100 mL), anhydrous DCM (50 mL), N,N'-diisopropylcarbodiimide (DIC, 1.20 mmol, 188 µL), and 1-hydroxy-7-azabenzotriazole (HOAt, 0.90 mmol, 122.5 mg) were added to the crude unprotected peptide for the cyclization. The solution was stirred under dry nitrogen gas overnight. After the formation of a cyclic-linear peptide, the chemical structure was confirmed by MALDI analysis. Then the solvents were removed under low pressure, and the crude product was dried overnight. The freshly prepared cleavage cocktail (TFA, anisole, thioanisole, 9:1:2 v/v/v and 50 mg of DTT, 20 mL) was then added to the crude products. The reaction mixture was continued to stir at room temperature for 4 h. The precipitation of the peptides was conducted in cold diethyl ether. After centrifugation, the crude peptides were purified by using reversed-phase HPLC and lyophilized.

$[R_5K]W_7A$ (2): MALDI-TOF (m/z): $C_{115}H_{149}N_3O_{14}$, calculated: 2282.1928. found: 2283.4850 $[M+H]^+$, $[R_5K]W_7C$ (3): MALDI-TOF (m/z): $C_{118}H_{149}N_{37}O_{15}S$, calculated: 2356.1755. found: 2358.3765 $[M+2H]^+$.

General Procedure for Coupling of the Peptides to Dox. The synthesis of this N-Fmoc-Dox-14-O-hemiglutarate, Dox-SH, and Dox-S—S-Pyr derivative was carried out according to the previously reported procedure (Lee, J. Y.; et al. *Int. J. Cancer* 128:2470-2480, 2011, which is incorporated herein by reference). N-Fmoc-Dox-14-O-hemiglutarate (1 equiv.), cyclic-linear ($[R_5K]W_7A$, 1 equiv.) or linear peptide ($R_5KW_7A$, 1 equiv.), benzotriazol-1-yloxytripyrrolidinophosphonium hexafluorophosphate (PyBOP, 1.35 equiv), and 1-hydroxybenzotriazole (HOBt, 2.70 equiv) were added to the glass vial under nitrogen atmosphere. The mixture was stirred to dissolve the compounds, followed by the addition of DIPEA (8 equiv.) in anhydrous DMF (1-2 mL). The mixture was stirred for 1.5 h in the absence of light. The solvent was then removed, and cold diethyl ether was added to the residue. The crude peptide was precipitated and centrifuged to obtain the crude solid peptide conjugate. A solution of piperidine in DMF was used (20% v/v, 2 mL for 5 min) to remove the Fmoc protecting group. The solution color turned blue, and the reaction was terminated by adding drops of TFA solution in DMF (20% v/v) until the solution color turned red. The solvent was removed under reduced pressure. The products were then dissolved in acetonitrile/water (50% v/v). The final products were purified using HPLC and characterized by using MALDI-TOF.

$R_5KW_7A$-Dox (4): MALDI-TOF (m/z): $C_{149}H_{182}N_{38}O_{29}$, calculated: 2967.3935. found: 2970.6516 [M+3H]$^+$.

[$R_5K$]$W_7A$-Dox (5): MALDI-TOF (m/z): $C_{148}H_{180}N_{38}O_{27}$, calculated: 2921.3880. found: 2922.95 [M+H]$^+$, 2397.83 [$R_5K$]$W_7A$-Glutarate]$^+$.

The activated Dox (Dox-S—S-Pyr, 1 equiv.) and [$R_5K$]$W_7C$ were dissolved in a methanol/water mixture (1:4, v/v, 4 mL). The mixture was stirred under nitrogen gas overnight at room temperature. After completion of the reaction as monitored by MALDI mass, the peptide-Dox conjugate was purified using HPLC.

[$R_5K$]$W_7C$—S—S-Dox (6): MALDI-TOF (m/z): $C_{149}H_{183}N_{39}O_{25}S_2$, calculated: 2982.3689. found: 2985.9900 [M+3H]$^+$ and 3001.7700 [M+Na]$^+$.

Dox-resistant Cell Lines. Acquired resistance to Dox was induced in wild-type triple-negative breast cancer cell line MDA-MB-231 (MDA-231WT) as described before (Aliabadi, H. M.; et al. *J. Control. Release* 172:219-228, 2013, which is incorporated herein by reference). Briefly, MDA-231WT cells were exposed to Dox at an initial concentration of 0.05 µg/mL for one week or three consecutive expansions (whichever came later). The exposure concentration was gradually increased to 2 µg/mL, and the cell viability was controlled at the end of each concentration exposure. Resistance induction was confirmed via calculation of $LC_{50}$ following a sigmoidal effect model explained elsewhere (Bousoik, E.; et al. *Front. Oncol.* 9:1070, 2019, which is incorporated herein by reference) and determination of P-glycoprotein (P-gp) expression. Uterine sarcoma cell line MES-SA/MX2 was selected as a cell line that overexpresses P-gp and demonstrates altered topoisomerase II catalytic activity as mechanisms for multi-drug resistance.

In Vitro Cytotoxicity Assay of Peptide-Drug Conjugates. The cytotoxicity of the compounds was determined by using human leukemia cell line (CCRF-CEM), human ovarian adenocarcinoma cells (SKOV-3) cells, kidney cell line (LLC-PK1), gastric adenocarcinoma cells (AGS), and heart/myocardium cells (H9C2) to evaluate the toxicity of the generated peptides according to a previously reported procedure (Rahman, A.; et al. *Proc. Am. Assoc. Cancer Res.* 26:2295-2299, 1985, which is incorporated herein by reference). In brief, CCRF-CEM cells were seeded at 50,000 cells in 0.1 mL per well in 98-well plates. In the case of other cell lines, the cells were seeded at 5,000 cells (0.1 mL per well in 96-well plates). The cells were seeded in medium (RPMI-1640 containing FBS (10%)), 24 h prior to the experiment. The compounds at different concentrations (10-50 µM) were added to each well in triplicate and incubated for 24 and 72 h at 37° C. in a humidified atmosphere of 5% $CO_2$. Dox (5 µM) was used as a positive control, while water and cell culture medium were used as negative controls. The compounds were dissolved in water; water was used as a negative control to normalize the data. After the incubation period, MTS reagent (20 µL) was added to each well. The incubation was continued for 2 h. Cell viability was then determined by determination of the fluorescence intensity at 490 nm using a SpectraMax M2 microplate spectrophotometer. The percentage of cell viability was then calculated using the following equation: [(OD value of cells treated with the compound)−(OD value of culture medium)]/[(OD value of control cells)−(OD value of culture medium)]× 100% (FIGS. 6-9).

The cytotoxicity of the peptide-Dox conjugate in resistant triple-negative breast cancer and uterine sarcoma cell lines (MDA-231R, MDA-231WT, and MES-SA/MX2) was evaluated by a Cell Counting 8 (CCK8) KIT. The peptide-Dox conjugate was added to the cells in triplicate with different concentrations (0-40 µM). Cells were incubated at 37° C. and 5% $CO_2$ for 24 h. After this incubation period, 10 µL of CCK8 reagent was added to each well, and plates were incubated at the same conditions for 2 h. The absorbance of each well was determined at 450 nm using the SpectraMAX M5 microplate reader. After subtracting the signal from blank wells that contain medium without cells in the plate with CCK-8 solution added, the results were normalized to cells treated with normal saline (considered as 100%)

Efficiency in Dox-Resistant Cells. In order to compare the cytotoxic effect of free and peptide-conjugated Dox in Dox-resistant cells, MDA-231WT (as a Dox-sensitive cell line as control) and MDA-231R and MES-SA/MX2 cells as Dox-resistant cells were exposed to a wide range of Dox (or Dox-equivalent for the peptide-conjugated drug) concentrations (0.05-40 µM). Cells were seeded in 96-well plates with approximately 50% confluency and were incubated for 24 h in 37° C. and 5% $CO_2$. Study groups received normal saline (as control) or different concentrations of free or Peptide-conjugated Dox (in triplicates) and were then incubated again for 48 h. The cell viability was determined after this incubation period using the CCK-8 assay, as explained above. The $LC_{50}$ values were estimated using sigmoidal effect (% cell death) model according to the following equation:

$$\% \text{ Cell Death} = \frac{\% \text{ Maximum Cell Death} \times C^\gamma}{LC50^\gamma + C^\gamma}$$

where C represents the concentration of the drug and $LC_{50}$ is the concentration that produces half of the maximum cell death. $\gamma$ is the Hill coefficient (steepness factor). The experimental values of percentage (%) cell death and concentration were fitted to the above equation using non-linear regression analysis. The values of percentage (%) maximum cell death, $LC_{50}$, and $\gamma$ were estimated.

Fluorescence and Confocal Microscopy. CCRF-CEM, SKOV-3, and H9C2 cells were seeded with EMEM media overnight on coverslips in six-well plates. Then the medium was removed and washed with opti-MEM. The cells were treated with Dox and the peptide-Dox conjugate (5 µM) in opti-MEM for different time intervals (3, 24, and 72 h) at 37° C. After 3 h incubation, the media containing the compound were removed, followed by washing with PBS three times. Then coverslips were placed on a drop of mounting medium on a microscope slide with the cell-attached side facing down. Fluorescence microscopy and laser scanning confocal microscopy were carried out using a Keyence Microscope System and Nikon AIR system, respectively. The cells were imaged using rhodamine and phase contrast channels.

In a separate experiment, confocal microscopy was used as follows. (i) Internalization of [$R_5K$]$W_7A$-Dox conjugate vs. free Dox was determined in Dox-resistant MDA-MB-231 and ME5-SA/MX2 cells as compared to the wild-type MDA-MB-231 cells. The cellular internalization was evaluated in Dox-sensitive and -resistant cells to study the effect of overexpression of the MDR efflux proteins on the Dox internalization by the peptide conjugates. The cells were seeded in 6-well plates as described above, and they were fixed and stained similarly after 24 h exposure to free Dox or peptide-Dox conjugates. (ii) Internalization of Dox and [$R_5K$]$W_7A$-Dox was determined into normal heart muscle cells. In order to further study the extent of cellular internalization of peptide-dox conjugates in healthy heart muscle cells as an indication for potential cardiotoxicity, the uptake studies were repeated using H9C2 myocardium cells. The cells were seeded and exposed to free Dox and peptide-Dox conjugates, and were stained 24 h after exposure according to the method disclosed above. (iii) [R$_5$K]W$_7$-Dox uptake was determined in wild-type MDA-MB-231 cells in the presence of different inhibitors of clathrin- and caveolae-dependent endocytosis mechanisms. The cellular internalization was evaluated at 4° C. and after exposure to the following uptake inhibitors on internalization of peptide-dox conjugates into MDA-MB-231 cells: chlorpromazine (a well-known inhibitor of clathrin-mediated endocytosis, genistein (an inhibitor of caveolae-mediated uptake), chloroquine (a lysosomal inhibitor) and an antimalaria medication that reduces the expression of phosphatidylinositol binding clathrin assembly protein, or PICALM, an abundant protein in clathrin-coated pits, and inhibitor of endocytosis, and nystatin (a caveolae/lipid raft dependent endocytosis inhibitor. Cells were seeded as disclosed above, and were exposed to one of the uptake inhibitors at final concentrations of 20 μg/mL, 6 μg/mL, 50 μg/mL, and 50 μg/mL for chlorpromazine, chloroquine, nystatin, and genistein, respectively, for 30 min, or were kept at 4° C. for 30 min. After the 30 min incubation time, cells were exposed to free Dox or peptide-Dox conjugates for the cellular internalization experiment as described above.

Fluorescence-Activated Cell Sorter (FACS) Analysis of Cellular Uptake Experiment in the Presence of Endocytosis Inhibitors. A flow cytometry study was conducted in the presence of endocytosis inhibitors, such as nystatin, chlorpromazine, chloroquine, and methyl β-cyclodextrin, to determine whether the cellular uptake for the peptide [R$_5$K]W$_7$A-Dox is endocytosis-dependent. CCRF-CEM cells (1×10$^6$ cells/well) were incubated in six-well plates in serum-free RPMI media. Then conjugate [R$_5$K]W$_7$A-Dox (5 μM) alone as the control and in the presence of various inhibitors including nystatin (50 μg/mL), chloroquine (100 μM), chlorpromazine (30 μM), and methyl-s-cyclodextrin (2.5 mM) were added in serum-free RPMI to the cells. The mixture was preincubated for 30 min at 37° C. before addition to the cells. The cells were incubated (37° C. in a humidified atmosphere of 5% CO$_2$) for 3 h in 2 mL of serum-free RPMI media. After the 3 h incubation, the media containing drugs and cells were removed. Following centrifuging 2500 RPM for 5 min with and washing with phosphate buffer saline, the cells were resuspended in the flow cytometry buffer (Nerd Blood Bank Saline pH 7-7.2) and analyzed by the flow cytometry (FACSVerse: Becton Dickinson) using propidium iodide channel and BD FACSuite software. The presented data are based on the percentage of 10,000 cells collected. All assays were performed in triplicates.

Stability Studies. The stability of [R$_5$K]W$_7$A-Dox conjugate was evaluated using phosphate-buffered saline (PBS) and fetal bovine serum (FBS). FBS was purchased from Invitrogen and ATCC. FBS (20%) was incubated with [R$_5$K]W$_7$A-Dox (75 μL, 1 mM in water) at 37° C. followed by intermediate mixing. An aliquot of 75 μL of the mixture was taken out at different time intervals (5 min to 24 h) and diluted with water (75 μL). The mixture was analyzed by using analytical HPLC, detecting the wavelength of 490 nm. The area under the curve (AUC) was calculated and used to determine the percentage of released Dox and the remaining prodrug at a given time.

Cellular Hydrolysis. Intracellular hydrolysis of [R$_5$K]W$_7$A-Dox and accumulation of Dox and the peptide-Dox conjugate were determined in CCRF-CEM cells by HPLC analysis. CCRF-CEM cells were grown in 75 cm$^2$ culture flasks with serum-free RPMI medium to approximately 70-80% confluence (1.37×10$^7$ cells/mL). The medium was first replaced with fresh RPMI medium having [R$_5$K]W$_7$A-Dox conjugate (5 μM). Then the cells were incubated for 4 h at 37° C. The medium containing the conjugate was replaced with a fresh RPMI serum-free medium. The cells were partitioned/transferred to culture plates (six well), having 1.37×10$^7$ cells per well in 5 mL of medium, and incubated for the indicated time. After incubation, the cells were collected by centrifugation. The medium was removed carefully by decantation, and cell pellets were washed with ice-cold PBS to remove any medium. The cell pellets were thoroughly extracted with an equal volume of methanol, chloroform, and isopropanol mixture (4:3:1, v/v/v) and filtered through 0.2 μm filters. The relative Dox and [R$_5$K]W$_7$A-Dox concentrations in cell lysates were quantified by analytical HPLC using the water/acetonitrile solvent method.

Results

Linear and hybrid cyclic-linear peptides were synthesized by Fmoc/tBu solid-phase peptide synthesis. The linear peptide R$_5$KW$_7$A was assembled on the H-Arg(Pbf)-2-chlorotrityl chloride resin. The resin was dried, washed, and cleaved by a cleavage cocktail (reagent R) to yield the linear R$_5$KW$_7$A (1) (FIG. 1), which was purified by reversed-phase HPLC. For the synthesis of the hybrid cyclic-linear peptides [R$_5$K]W$_7$A (2) and [R$_5$K]W$_7$C (3) (FIG. 1), the linear protected peptides, R$_5$K(Dde)W$_7$A and R$_5$K(Dde)W$_7$C were assembled on the H-Arg(Pbf)-2-chlorotrityl chloride resin first. The Dde group of N-terminal lysine was removed in the presence of hydrazine (2% v/v in DMF). The side chain-protected peptide was cleaved from the resin using AcOH/TFE/DCM (1:2:7 v/v/v) cocktail. The cyclization of the side-chain protected peptide was performed under very dilute conditions in the presence of HOAt and DIC. The hybrid peptide was cleaved in the presence of reagent R, purified using reversed-phase HPLC (FIG. 3), and used for the conjugation with Dox.

N-Fmoc-Dox-14-O-hemiglutarate was prepared as described previously (Darwish, S. et al. Eur. J. Med. Chem. 161:594-606, 2019). In brief, the reaction of glutaric anhydride with Fmoc-protected Dox was carried out to produce the Dox hemiglutarate ester with a free COOH, which after HPLC purification and lyophilization, was used for coupling with linear and cyclic-linear peptides. The conjugation of the peptides with N-Fmoc-Dox-14-O-hemiglutarate was achieved in a similar pattern. The equimolar amounts of the fully deprotected peptide and Dox were coupled through the reaction of the free amino group of peptides and carboxylic acid in the Fmoc-protected Dox. The carboxylic group in Fmoc-protected Dox was pre-activated in the presence of HOAt/PyBOP/DIPEA in DMF for 15 min before reaction with the peptides. After conjugation, the Fmoc protecting group of Dox was removed using piperidine and was then acidified to yield [R$_5$K]W$_7$A-Dox conjugate (5) (FIG. 4) that was purified using HPLC and lyophilized.

To produce [R$_5$K]W$_7$C—S—S-Dox (6), Dox was modified by reacting with a bifunctional cross linking agent. The amine group of Dox was reacted with 2-iminothiolane hydrochloride (Traut's reagent) under optimal conditions of basic medium to generate Dox-SH, containing an amidine with a free sulfhydryl group, which was activated by reacting with pyridyl disulfide (Pyr-S—S-Pyr) in acidic medium, yielding the corresponding more reactive Dox-S—S-Pyr containing a disulfide bridge that was used for the reaction with [R$_5$K]W$_7$C to yield [R$_5$K]W$_7$C—S—S-Dox (FIG. 5). This type of chemical modification for Dox permitted the conjugation with the thiol group of the cysteine in the cyclic peptide. The structures of all the final compounds were confirmed by a high-resolution MALDI-TOF mass spectrometer. The purity of the final product was confirmed to be ≥95% by reversed-phase analytical HPLC using a gradient system with water (0.1% TFA) and acetonitrile (0.1% TFA) as eluting solvents.

Cytotoxicity of Peptide-Dox Derivatives. The cytotoxicity of Dox was compared with peptide-Dox conjugates in CCRF-CEM, AGS, SK-OV-3, MDA-MB-231 triple-negative breast cancer (TNBC), and MES-SA/MX2 cells, which is a Dox-resistant cell line to determine the effect of the conjugation of the peptide with Dox. These cancer cell lines were selected to compare the antiproliferative activities of Dox versus the conjugates in Dox-sensitive and Dox-resistant cells. Normal H9C2 cardiac myoblasts were used to test the cardiotoxicity of the conjugates.

Figure 6:
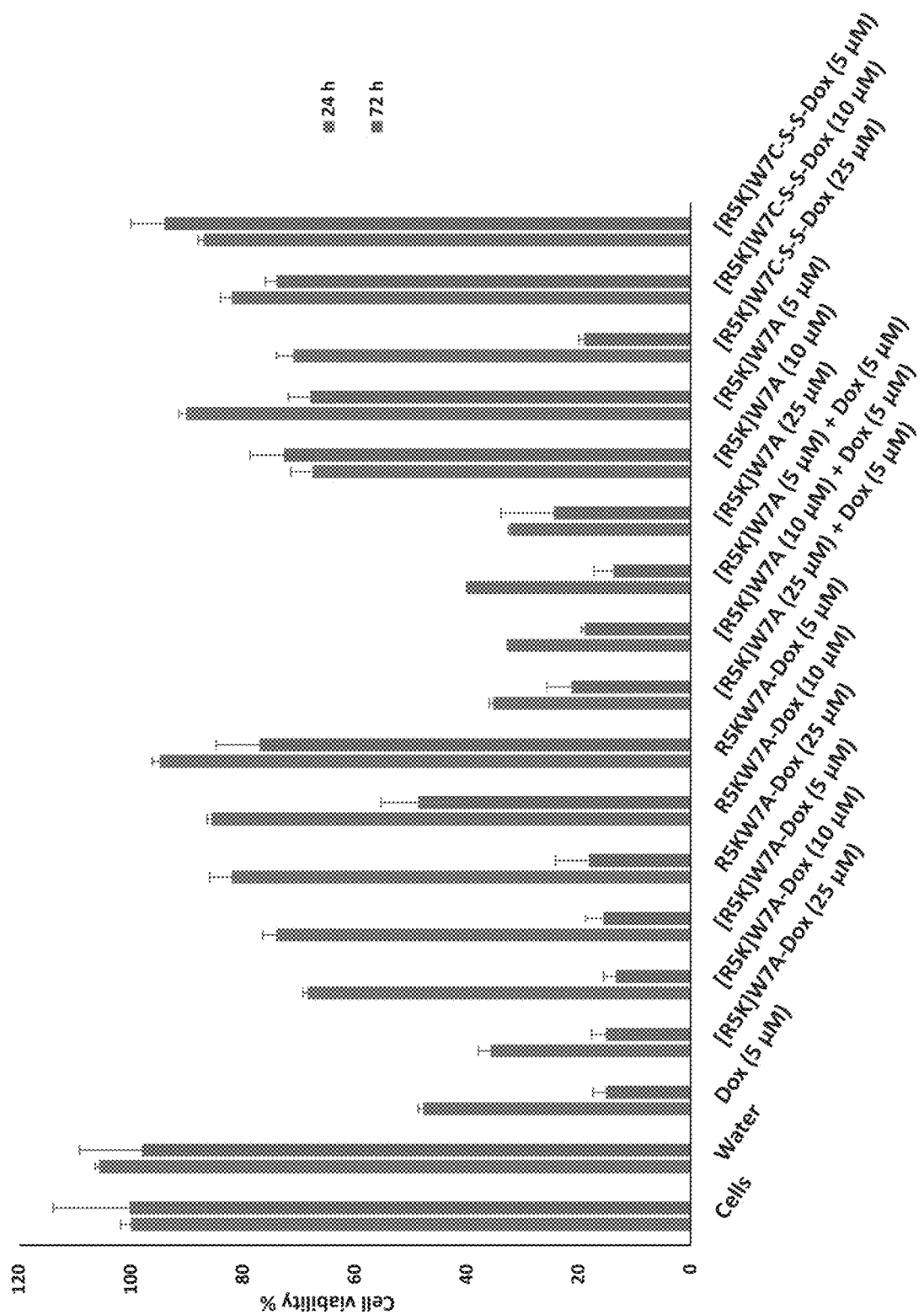
FIG. 6 depicts the cytotoxicity of linear R$_5$KW$_7$A-Dox and cyclic-linear [R$_5$K]W$_7$A-Dox and [R$_5$K]W$_7$C—S—S-Dox conjugates in CCRF-CEM cells.

To evaluate the cytotoxicity of synthesized peptides and conjugates, a cell viability assay was first conducted in CCRF-CEM cells with linear R$_5$KW$_7$A-Dox, [R$_5$K]W$_7$A-Dox, and [R$_5$K]W$_7$C—S—S-Dox conjugates in different concentrations, as shown in FIG. 6. Dox (5 µM) reduced cell survival by 52% and 85% at 5 µM after 24 and 72 h, respectively. [R$_5$K]W$_7$A-Dox conjugate was significantly more efficient in reducing the viability in the CCRF-CEM cell line than linear R$_5$KW$_7$A-Dox conjugate at experimental concentrations of 5, 10, and 25 µM after 24 and 72 h incubation. The conjugate (25 µM) was significantly more cytotoxic (reduced the viability by 64%) than Dox (5 µM) (reduced the viability by 52%) after 24 h incubation while it was less active at 5 µM and 10 µM. However, conjugate [R$_5$K]W$_7$A-Dox exhibited comparable cytotoxicity (84-87%) at 5, 10, and 25 µM after 72 h incubation when compared with Dox (5 µM) (85%), suggesting the slow hydrolysis of the conjugate to Dox and peptide. Peptide [R$_5$K]W$_7$ alone generated a significant amount of toxicity at 25 µM concentration even after 24 h, reducing the cell viability by 68%, which was even more than Dox alone; however, the peptide alone showed minimal cytotoxicity (10-22%) at other concentrations even after 72 h. The physical mixture of [R$_5$K]W$_7$ (5 µM)+Dox (5 µM) showed slightly higher antiproliferative activity (reduced viability by 60-67%) than that of Dox (52%) after 24 h incubation.

[R$_5$K]W$_7$C—S—S-Dox was able to reduce the cell viability by 79% after 72 h of incubation at 25 µM concentration. However, when compared with [R$_5$K]W$_7$A-Dox, which was significantly cytotoxic after 72 h even at 5 µM, [R$_5$K]W$_7$C—S—S-Dox was significantly less cytotoxic. Thus, further studies were conducted using [R$_5$K]W$_7$A-Dox conjugate. Because of the efficiency of [R$_5$K]W$_7$A-Dox conjugate, all the remaining cytotoxicity assays were conducted using this conjugate.

Figure 7:
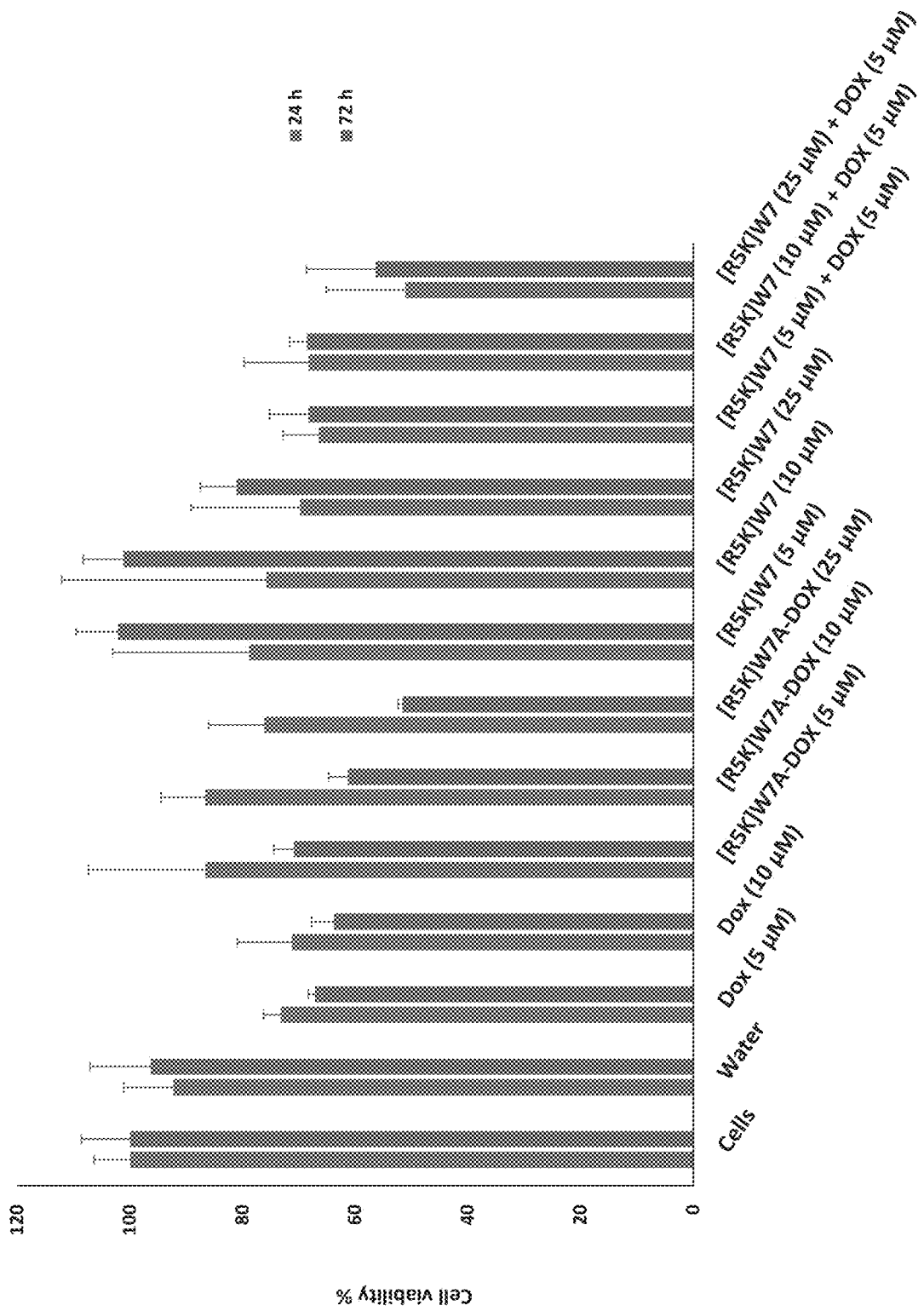
FIG. 7 depicts the cytotoxicity of [R$_5$K]W$_7$A-Dox conjugate in AGS cells.

Cell viability assay was conducted in AGS cells with different concentrations of [R$_5$K]W$_7$A, [R$_5$K]W$_7$A-Dox, and a physical mixture of [R$_5$K]W$_7$A at 5, 10, 25, and 50 µM with Dox at 5 µM as shown in FIG. 7. [R$_5$K]W$_7$A alone did not generate any significant cytotoxicity after 24 and 72 h at 5 and 10 µM. However, [R$_5$K]W$_7$A reduced cell survival by 24% and 87% at 25 and 50 µM, respectively, after 72 h. Dox reduced cell survival by 46% and 87% at 5 µM after 24 and 72 h, respectively. While conjugate [R$_5$K]W$_7$A-Dox was not significantly cytotoxic to this cell line at 5 and 10 µM after 24 h, peptide-Dox conjugate reduced the cell viability by almost 73-90% at different concentrations after 72 h, presumably due to the hydrolysis of the conjugate to Dox at this time. The physical mixture of Dox at 5 µM with different concentrations of peptide similar to concentrations used in the conjugates reduced the cell survival significantly by 55-69% and 88-89% after 24 and 72 h, respectively, which was slightly higher when compared with Dox alone (46%) after 24 h.

Figure 8:
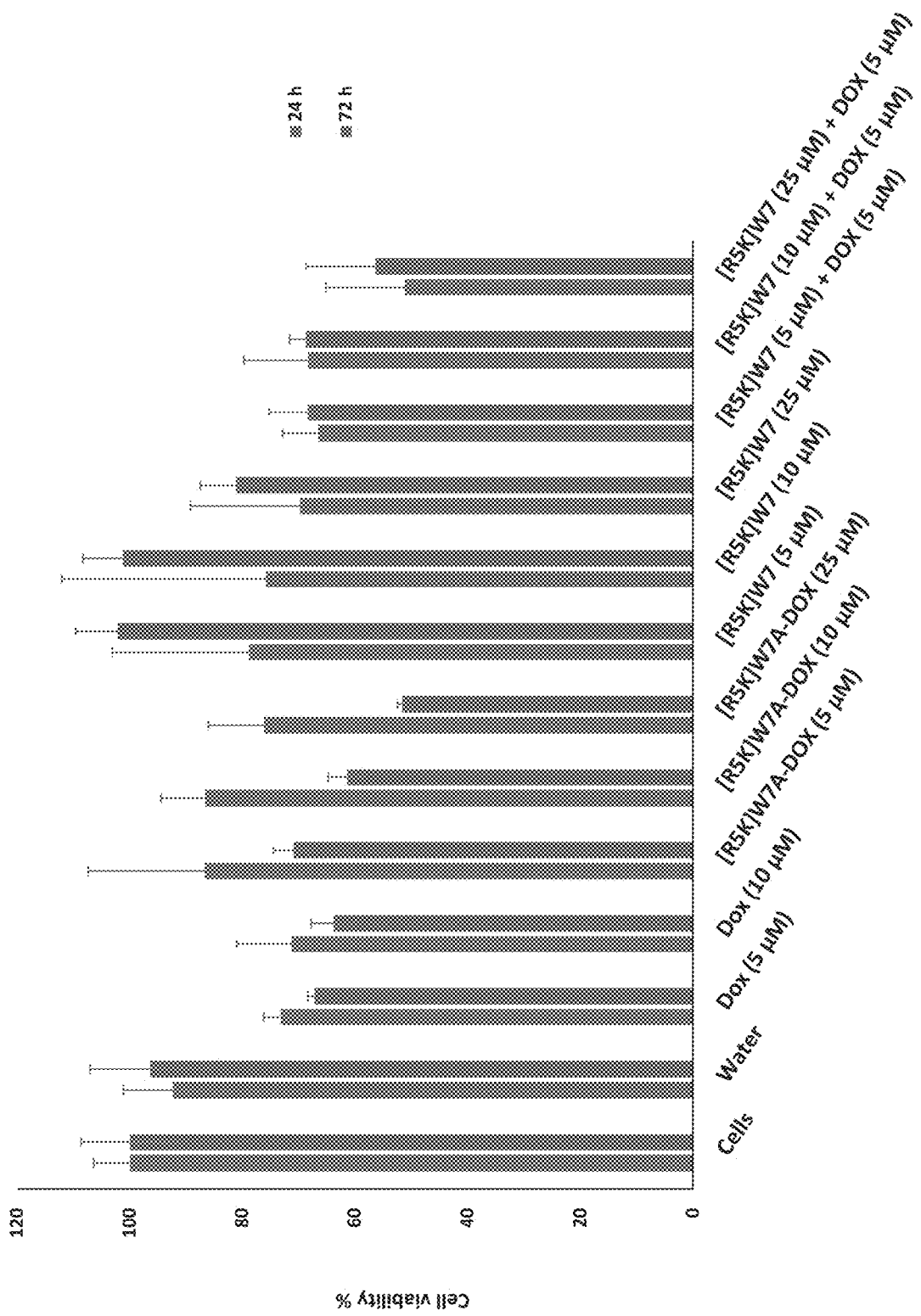
FIG. 8 depicts the cytotoxicity of [R$_5$K]W$_7$A-Dox conjugate in SK-OV-3 cells.

Cell viability assay was also conducted in SK-OV-3 with different concentrations of [R$_5$K]W$_7$A, [R$_5$K]W$_7$A-Dox, and physical mixture of [R$_5$K]W$_7$A at 5, 10, and 25 µM with Dox at 5 µM as shown in FIG. 8. Dox (5 and 10 µM) was used as a control. In general, peptide, Dox, the conjugate, and the physical mixture exhibited less cytotoxicity in SK-OV-3 cells than CCRF-CEM and AGS cells, possibly due to the presence of efflux mechanism in ovarian cancer cells. The peptide alone exhibited minimal cytotoxicity (21-30%) after 24 at 5, 10, and 25 µM and 19% at 25 µM after 72 h incubation. Dox reduced the cell survival by 27 and 33% at 5 µM after 24 and 72 h, respectively, while conjugate [R$_5$K]W$_7$A-Dox was able to reduce the cell viability by 29, 39, and 48% at 5, 10, and 25 µM, respectively, after 72 h incubation. The physical mixture of Dox at 5 µM with different peptide concentrations reduced cell survival by around 31-45% at different time intervals. The physical mixture of the peptide (25 µM) and Dox (5 µM) was slightly more cytotoxic (44-49%) than Dox alone (5 and 10 µM) (27-36%).

Figure 9:
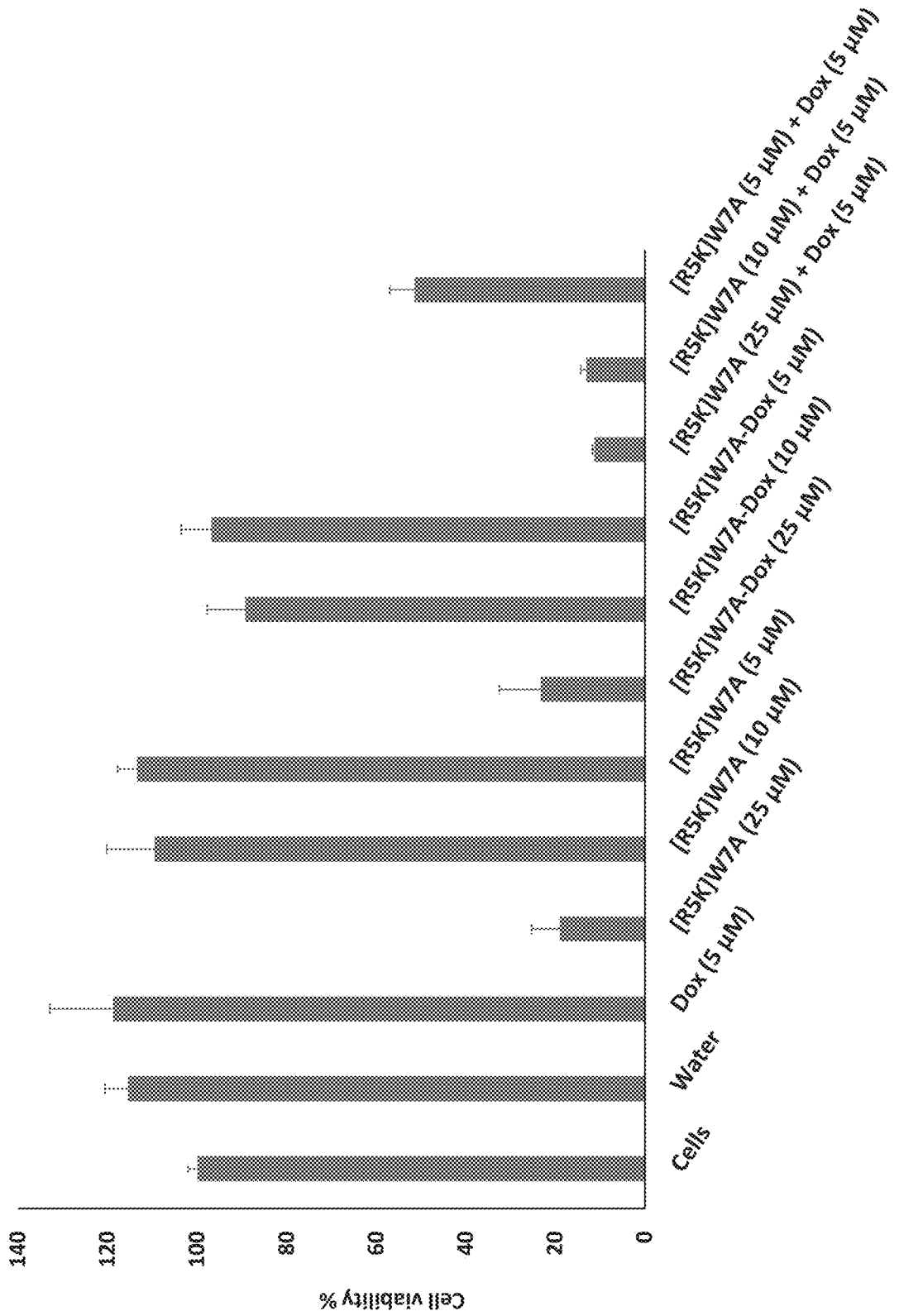
FIG. 9 depicts the cytotoxicity of [R$_5$K]W$_7$A-Dox conjugate in MES-SA/MX2 cells.

The cellular uptake and efficacy of [R$_5$K]W$_7$A-Dox in naïve and resistant cancer cells and non-tumorigenic cells were evaluated. First, the cell viability assay was conducted in uterine sarcoma cells (MES-SA/MX2, which is a Dox-resistant cell line) with different concentrations of [R$_5$K]W$_7$A, [R$_5$K]W$_7$A-Dox, and a physical mixture of [R$_5$K]W$_7$A at 5, 10 and 25 µM with Dox at 5 µM as shown in FIG. 9 after 72 h incubation. The cell line overexpresses P-gp and efflux small molecules drugs such as Dox. Dox at 5 µM did not show any toxicity to the cells as expected; however, the peptide alone and [R$_5$K]W$_7$A-Dox conjugate at 25 µM significantly reduced the cell viability by almost 80%. The physical mixture also exhibited significantly more cytotoxicity in this cell line when compared with Dox alone, reducing the cell viability by almost 87-89% at 10 µM and 25 µM peptide physically mixed with 5 µM of Dox, and 49% at 5 µM or peptide with 5 µM of Dox. These data suggest that the combination of [R$_5$K]W$_7$A (10 µM) and Dox (5 µM) showed a synergistic effect. The peptide alone ([R$_5$K]W$_7$A) and [R$_5$K]W$_7$A-Dox conjugate exhibited minimal cytotoxicity (0-10%) after 72 h at 5 and 10 µM.

Figure 10:
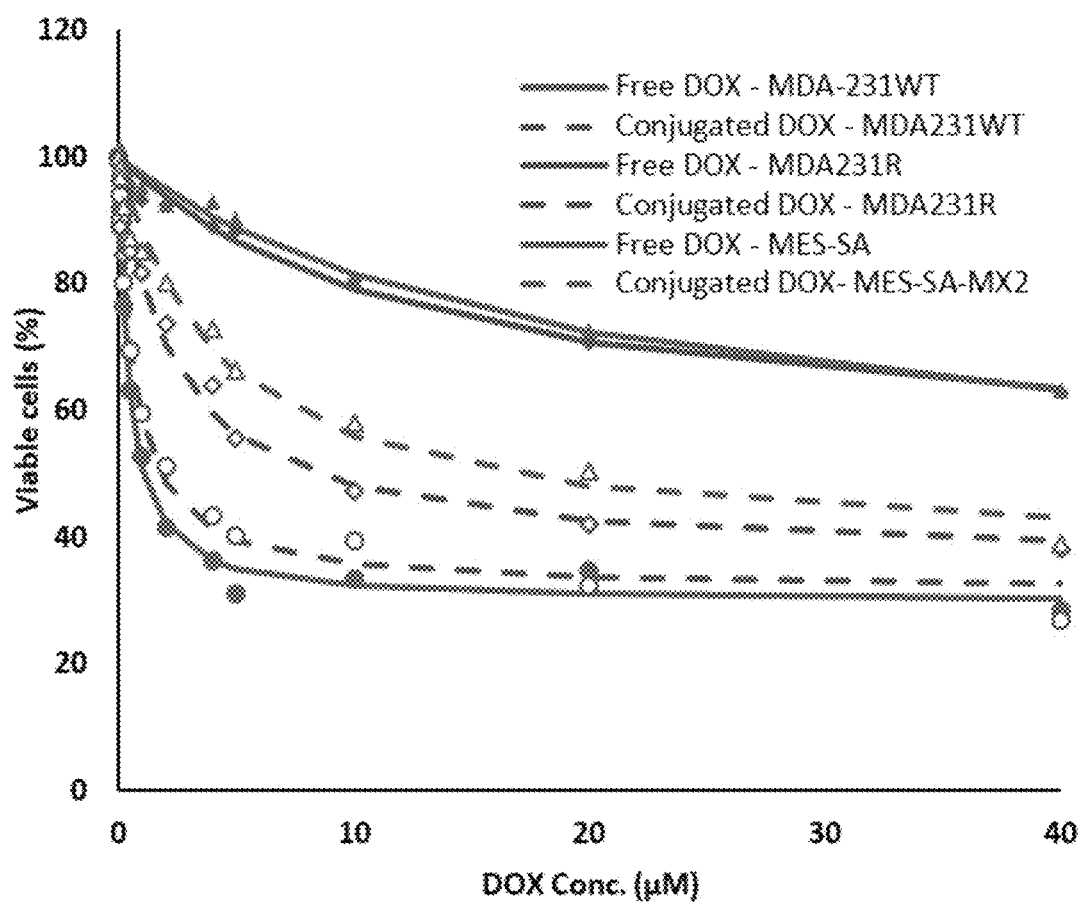
FIG. 10 depicts the cytotoxicity (LC$_{50}$ values) of [R$_5$K]W$_7$A-Dox conjugate and Dox in MDA-MB-231R and MES-SA/MX2 compared to wild type MDA-MB-231WT after 72 h.
Figure 11:
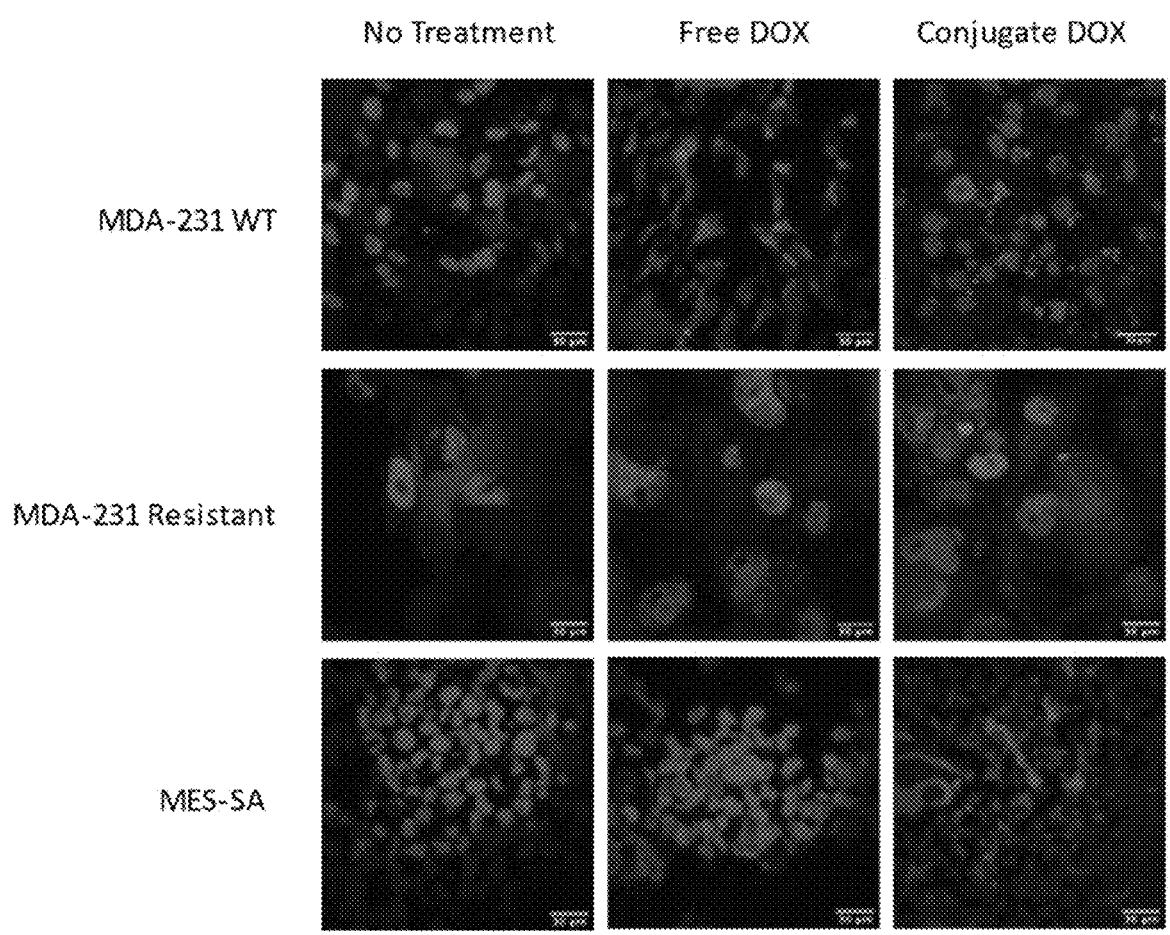
FIG. 11 depicts confocal microscopy of the hybrid peptide conjugate [R$_5$K]W$_7$A-Dox or free Dox in resistant MDA231 and ME5-SA/MX2 cells vs. wild-type MDA231WT cells. Red and blue channels represent Dox and DAPI (nuclei), respectively.

In addition to resistant uterine sarcoma cells (MES-SA/MX2) with confirmed MDR and overexpression of P-gp, Dox resistance was induced in triple-negative breast cancer cells (TNBC; MDA-MB-231) according to the previously reported methods (Aliabadi, H. M.; et al., 2013). While the LC$_{50}$ values of free Dox and [R$_5$K]W$_7$A-Dox conjugate were comparable in wild-type MDA-MB-231 cells (0.45 vs. 0.56 µM, respectively), [R$_5$K]W$_7$A-Dox conjugate was significantly more effective in both Dox-resistant MDA-MB-231R cells (LC$_{50}$ of 2.3 vs. 36 µM, respectively) and MES-SA/MX2 cells (LC$_{50}$ of 4.3 vs. 41 µM, respectively; FIG. 10 and Table 1). These data were consistent with confocal microscopy findings showing significant uptake of conjugated Dox in all cell lines studied (FIG. 11), clearly demonstrating that this approach can potentially overcome MDR.

TABLE 1

| Cells | Drug | LC$_{50}$ (µM) |
| --- | --- | --- |
| MDA-231WT | Free Dox | 0.45 |
|  | Conjugated Dox | 0.66 |
| MDA-231R | Free Dox | 36 |
|  | Conjugated Dox | 2.3 |
| ME5-5A-MX2 | Free Dox | 41 |
|  | Conjugated Dox | 4.3 |

The approach of inducing resistance in MDA-MB-231 cells was previously reported (Aliabadi et al, 2013). In that study, the Dox LC$_{50}$ was reported as 0.3 and 52 µg/mL in naïve and resistant MDA231 cells, respectively. The LC$_{50}$ of Dox in MDA-MB-231 cells is reported with a wide range of variety in the literature (from 73 nM or approximately 0.04 µg/mL to 3.16 µM or 1.8 µg/mL and 10 µM or 5.8 µM). Therefore, our observation for LC$_{50}$ in naïve cells is within the LC$_{50}$ reported in the literature. While the LC$_{50}$ of Dox in naïve cells in the present study is comparable to our previous observation, the LC$_{50}$ in MDA231R cells is significantly lower (36 vs. 52 µg/mL). This is possibly due to a shorter period of exposure time to Dox in the present study. However, the LC$_{50}$ in the MDA-MB-231R cells was still more than 50 times higher than the naïve cells, which indicates the proper resistance induction. The LC$_{50}$ of Dox in MES-SA/MX2 cells in the literature is varied as well, where different manuscripts have reported different LC$_{50}$ values from 2.4 µM (or approximately 1.4 µg/mL) to 20 µM (approximately 11.6 µg/mL) and approximately 84 µg/mL. In the present study, the LC$_{50}$ of Dox in this cell line is within this range. The [R$_5$K]W$_7$A-Dox conjugate showed significantly higher efficacy in both resistant cells compared to the free Dox. This indicates the ability of the peptide to internalize Dox into resistant cells despite the overexpression of MDR efflux proteins in these cell lines.

Figure 12:
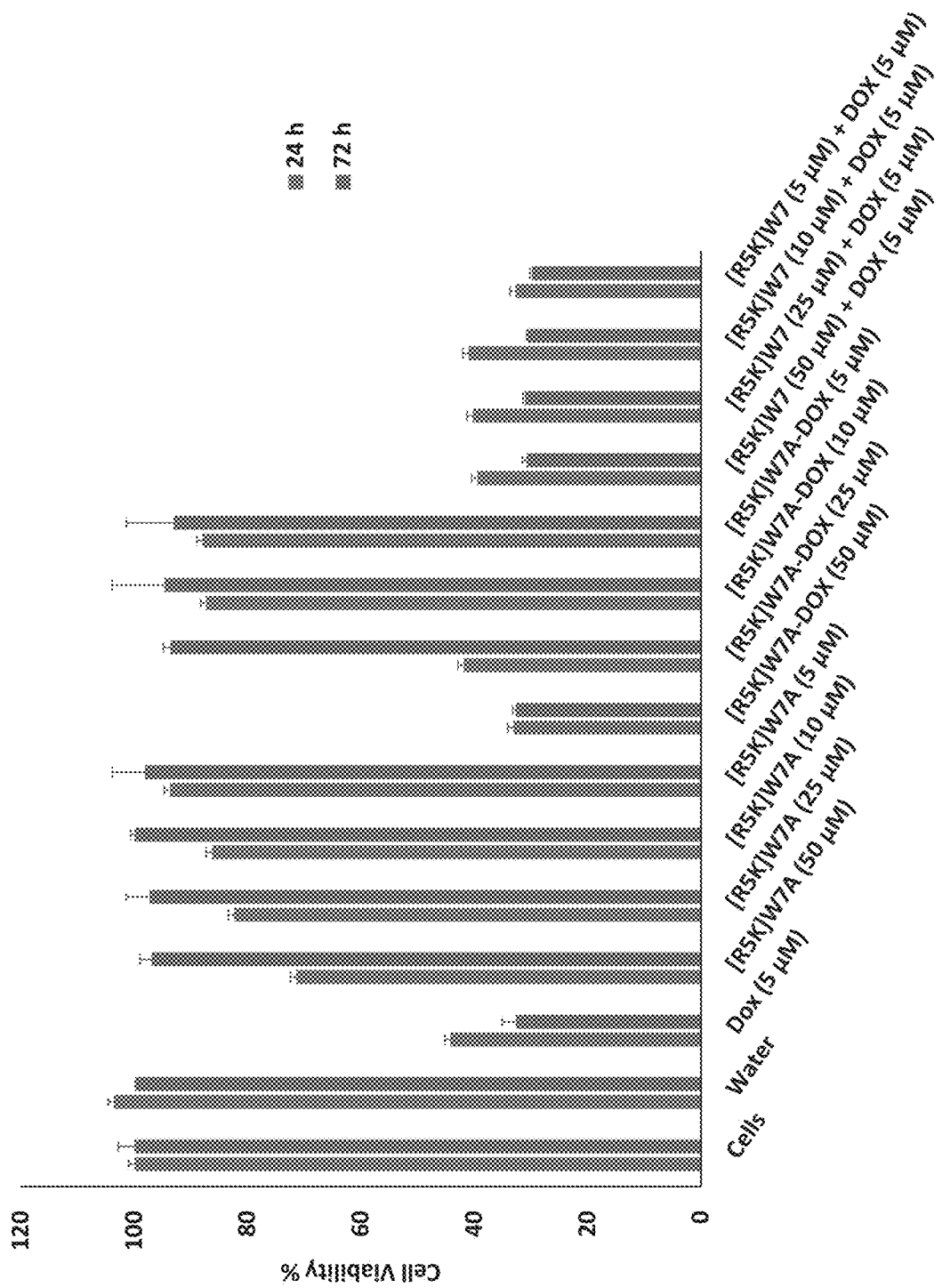
FIG. 12 depicts the cytotoxicity of [R$_5$K]W$_7$A-Dox conjugate in normal kidney cells.

Cell viability assays were also conducted in LLC-PK1 kidney cells with different concentrations of [R$_5$K]W$_7$A, [R$_5$K]W$_7$A-Dox, and physical mixture of [R$_5$K]W$_7$A at 5, 10, 25, and 50 µM with Dox at 5 µM as shown in FIG. 12. [R$_5$K]W$_7$A alone (5-50 µM) did not generate any significant cytotoxicity after 72 h incubation in the cells. Dox reduced cell survival by 64% and 77% at 5 µM after 24 h and 72 h, respectively, while [R$_5$K]W$_7$A-Dox conjugate was not cytotoxic to kidney cells at as high as 10 µM concentration after 24 h and 72 h incubation with the cells. However, [R$_5$K]W$_7$A-Dox conjugate exhibited significant toxicity (cell viability 33%) in this cell line at 50 µM, which was similar to Dox (5 µM). The physical mixture of Dox at 5 µM with different concentrations of peptide reduced the cell survival significantly by 60-70%, possibly due to the Dox cytotoxicity. [R$_5$K]W$_7$A-Dox conjugate was significantly less toxic in LLC-PK1 cells versus CCRF-CEM cells (FIG. 6) when compared at a concentration of 5-25 µM after 24 h and 72 h incubation.

Figure 13:
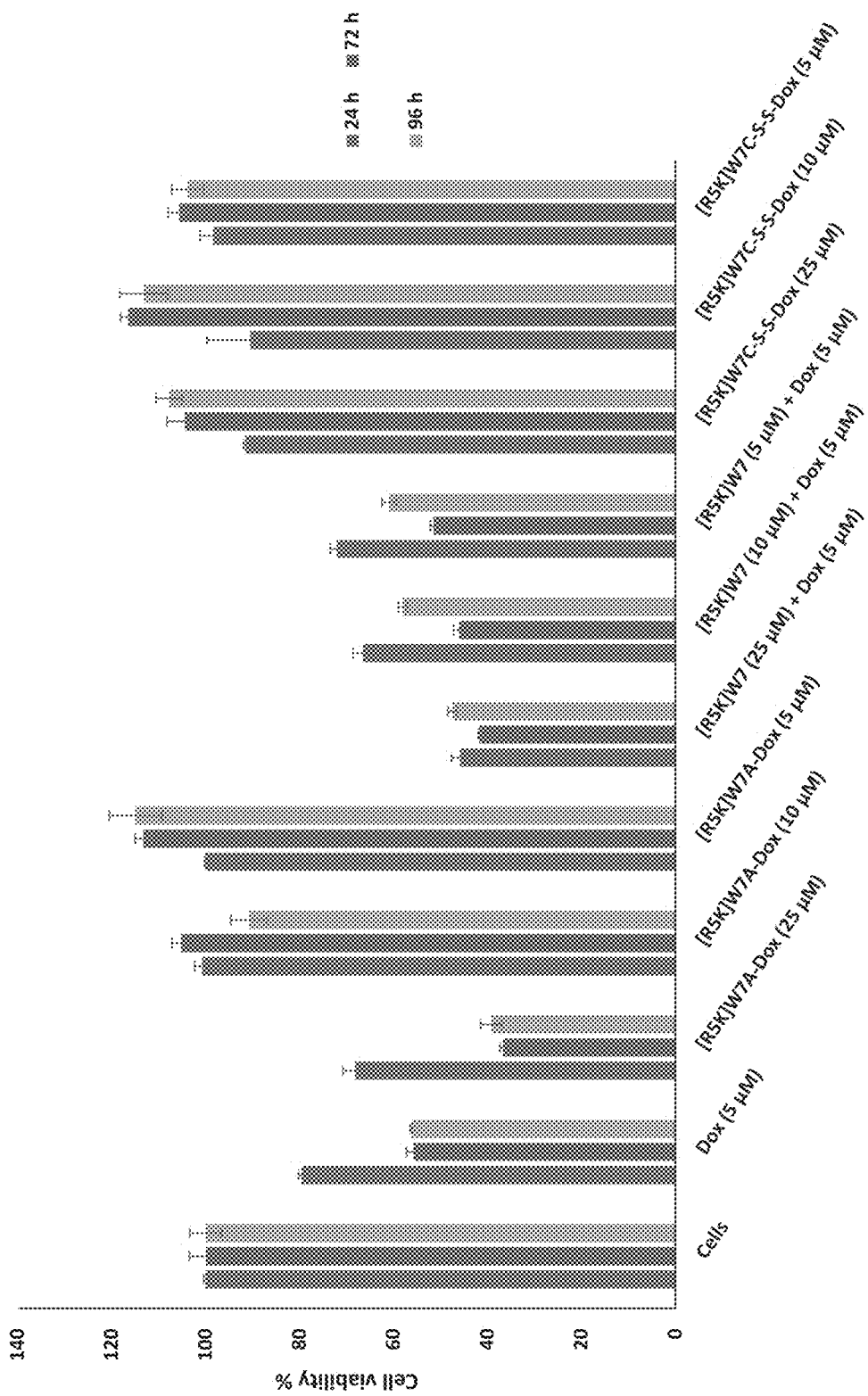
FIG. 13 depicts the cytotoxicity of [R₅K]W₇A-Dox conjugate and [R₅K]W₇C—S—S-Dox conjugate in normal heart H9C2 cells.

Cell viability assays were also conducted in rat heart H9C2 cells with different concentrations of [R$_5$K]W$_7$A-Dox and physical mixture of [R$_5$K]W$_7$A at 5, 10, and 25 µM with Dox at 5 µM as shown in FIG. 13. Dox reduced the cell survival by 20, 44, and 44% at 5 µM after 24 h, 72 h, and 96 h, respectively, while [R$_5$K]W$_7$A-Dox conjugate (5-10 µM) did not show any significant toxicity in this cell line after 24 h, 72 h, and 96 h incubation time. Moreover, [R$_5$K]W$_7$C—S—S-Dox (5-10 and 25 µM) did not show any cytotoxicity at any incubation time. The physical mixture of Dox at 5 µM with the peptide (5 µM) reduced the cell survival by 28%, 48%, and 39% in different time intervals, which was comparable to Dox activity at 5 µM. These data indicate that the cytotoxicity of the peptide-Dox conjugate is significantly less than Dox and the physical mixture at concentrations of 5-10 µM in the heart H9C2 cells while the conjugate was cytotoxic after 24 h and 72 h against CCRF-CEM cells.

Figure 14:
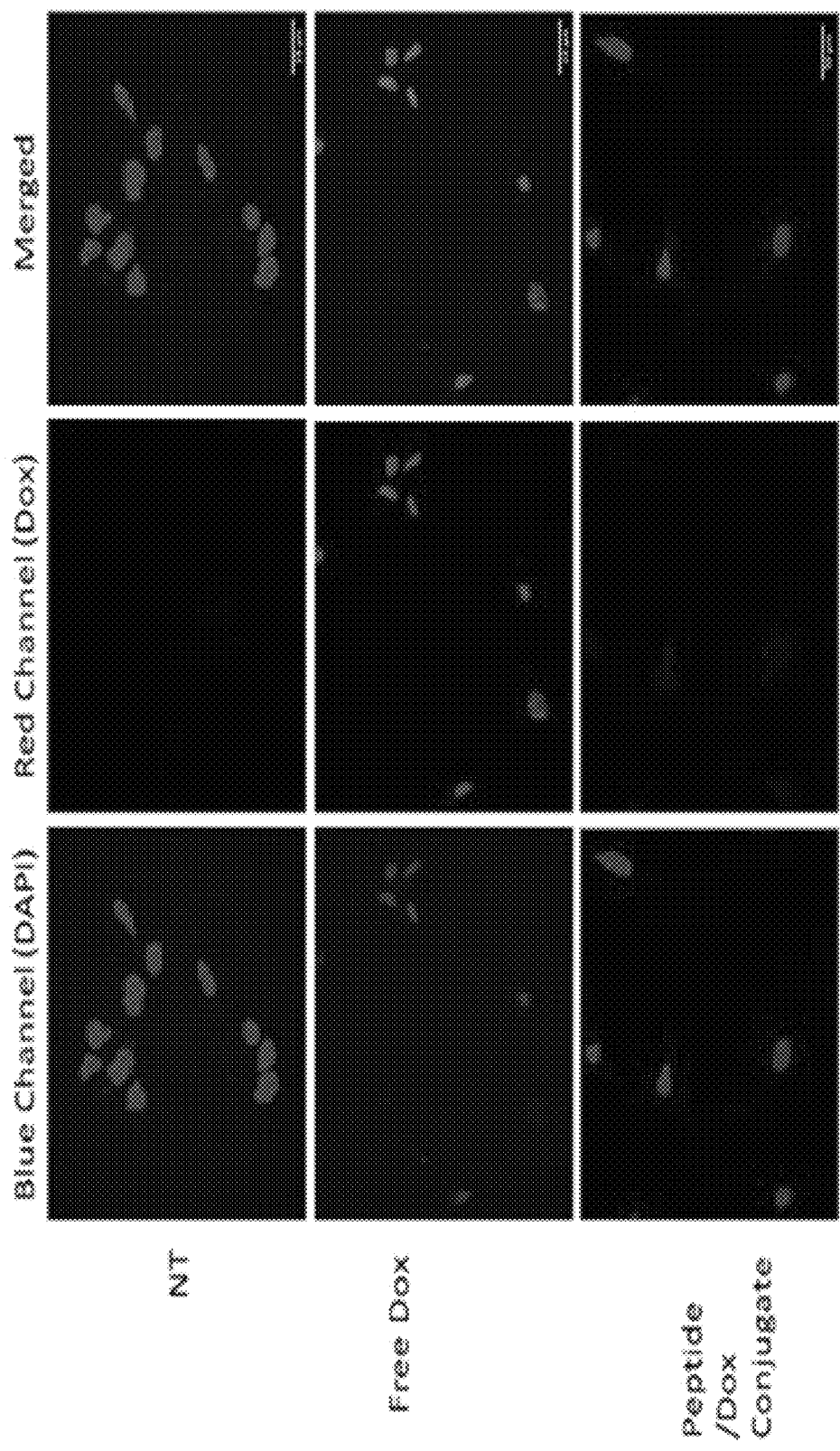
FIG. 14 depicts confocal microscopy images of Dox and [R₅K]W₇A-Dox conjugate after 24 h exposure of heart muscle cells. Red signal represents Dox autofluorescence.

Fluorescence micrographs were consistent with our cytotoxicity studies, indicating minimal uptake of [R$_5$K]W$_7$A-Dox in heart cells (FIG. 14).

All these data are suggesting that [R$_5$K]W$_7$-Dox conjugate can be used as an efficient prodrug, generating the same cytotoxicity for cancer cells as Dox, with minimal reduction in cell viability for normal cells in the body, such as kidney and heart cells.

Figure 19A:
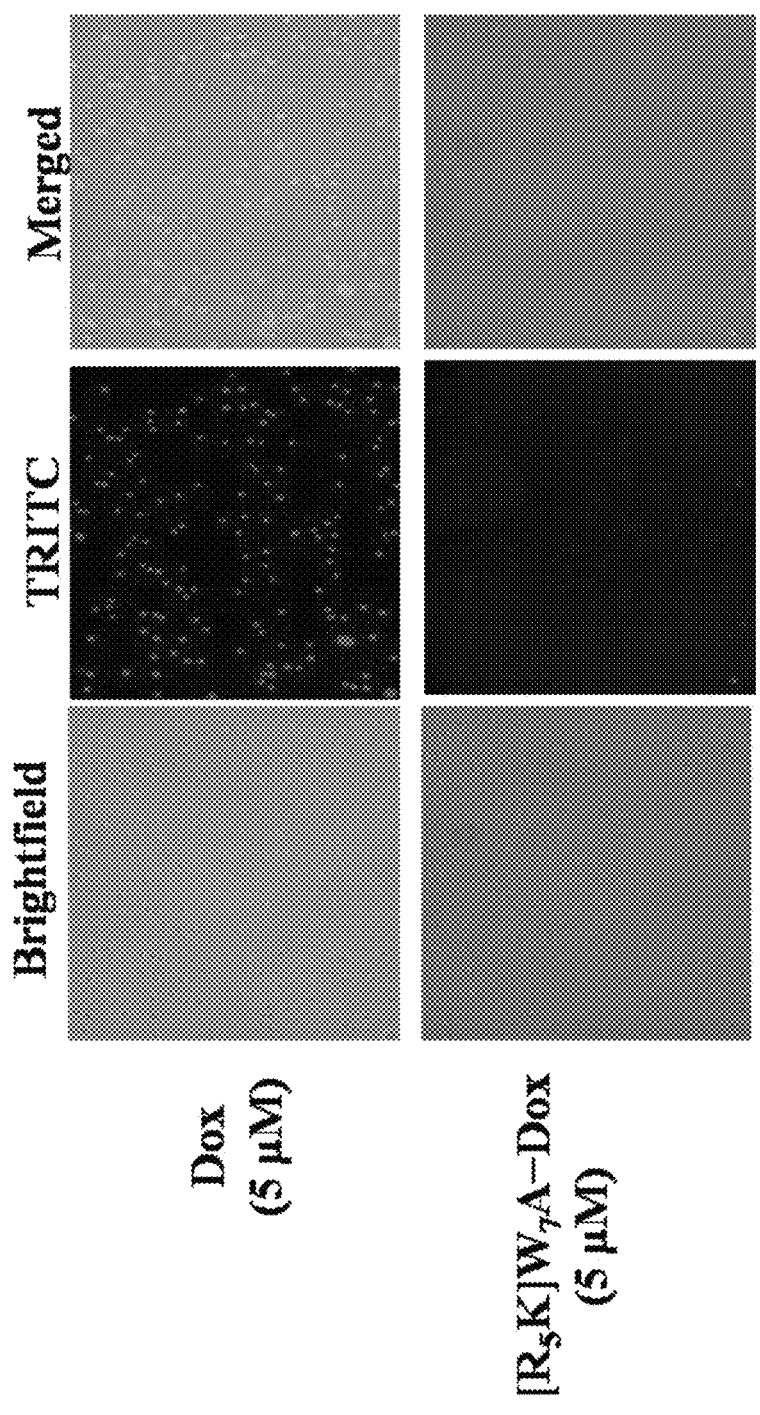
FIGS. 19A-B depict fluorescence microscopy images of Dox and [R₅K]W₇A-Dox (5 µM) uptake in CCRF-CEM cells after 3 h (FIG. 19A) and Dox, [R₅K]W₇A-Dox (5 µM), and [R₅K]W₇A (25 µM)+Dox (5 µM) in SK-OV-3 cells after 3 h (FIG. 19B). Red represents the fluorescence of Dox and blue represents the nucleus of the cells.
Figure 19B:
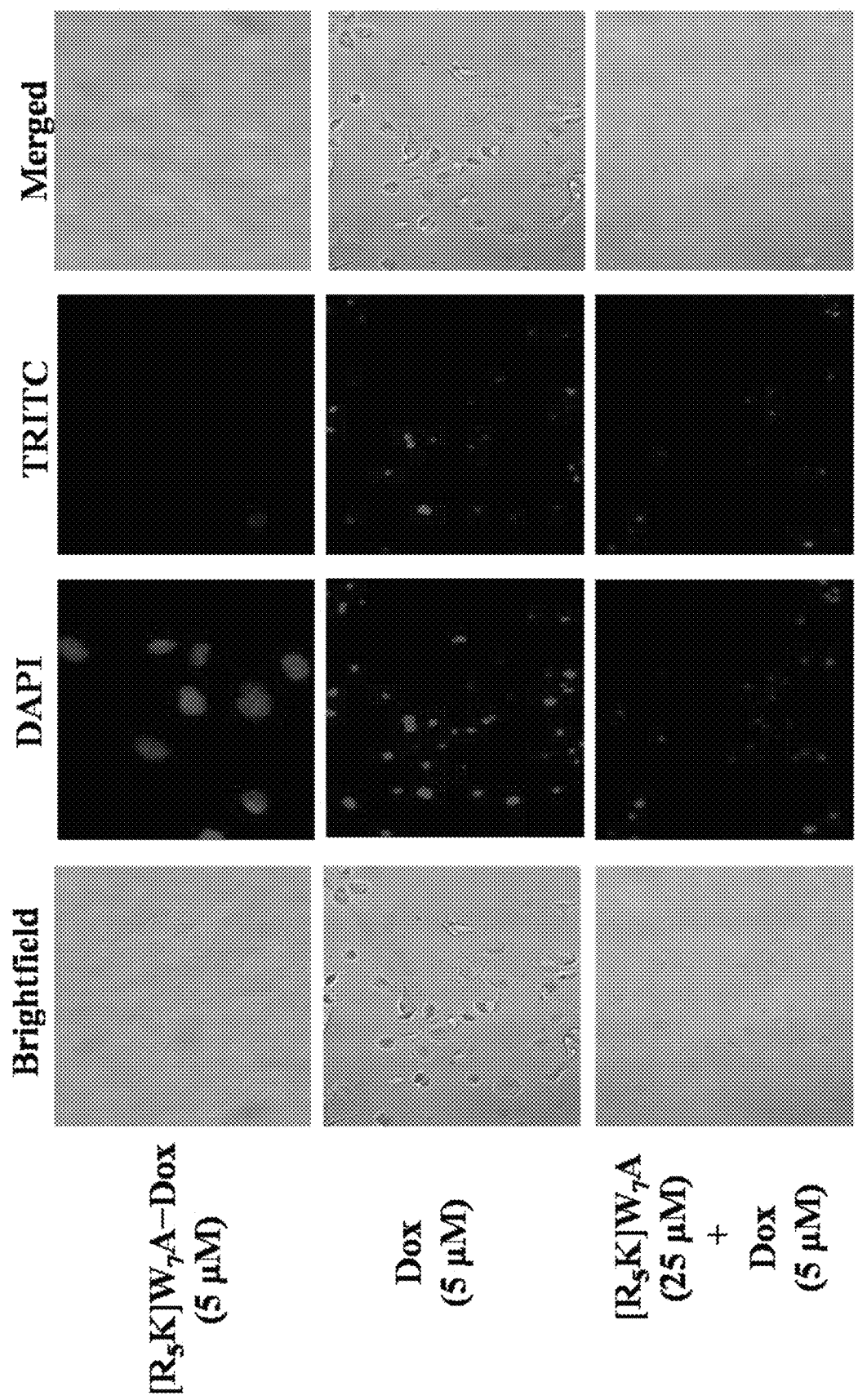

Confocal and Fluorescence Microscopy. FIGS. 19A and 19B show fluorescence microscopy images of CCRF-CEM and SK-OV-3 cells, respectively, after 3 h incubation with Dox and Dox-peptide conjugates. The results showed that the covalent conjugation of Dox with [R$_5$K]W$_7$A reduced the cellular uptake of the drug as compared with Dox alone. The fluorescence intensity of Dox in cells treated with [R$_5$K]W$_7$A-Dox was found to be significantly lower than that in cells treated with Dox alone (FIGS. 19A and 19B), indicating that the uptake of [R$_5$K]W$_7$A-Dox could take longer than 3 h. These data are consistent with cytotoxicity studies, suggesting that cytotoxicity of the conjugate was time-dependent in cancer cells, possibly due to the requirement for the adequate uptake in cells for generating antiproliferative activity. Although [R$_5$K]W$_7$A-Dox was not significantly uptaken by the cells after 3 h, the physical mixture of peptide [R$_5$K]W$_7$A (25 µM) with Dox (5 µM) significantly increased the cellular uptake of Dox. Free Dox and the physical mixture showed Dox localization mainly in the nucleus in SK-OV-3 cells (FIG. 19B). However, limited cellular localization of [R$_5$K]W$_7$A-Dox was observed.

Figure 15:
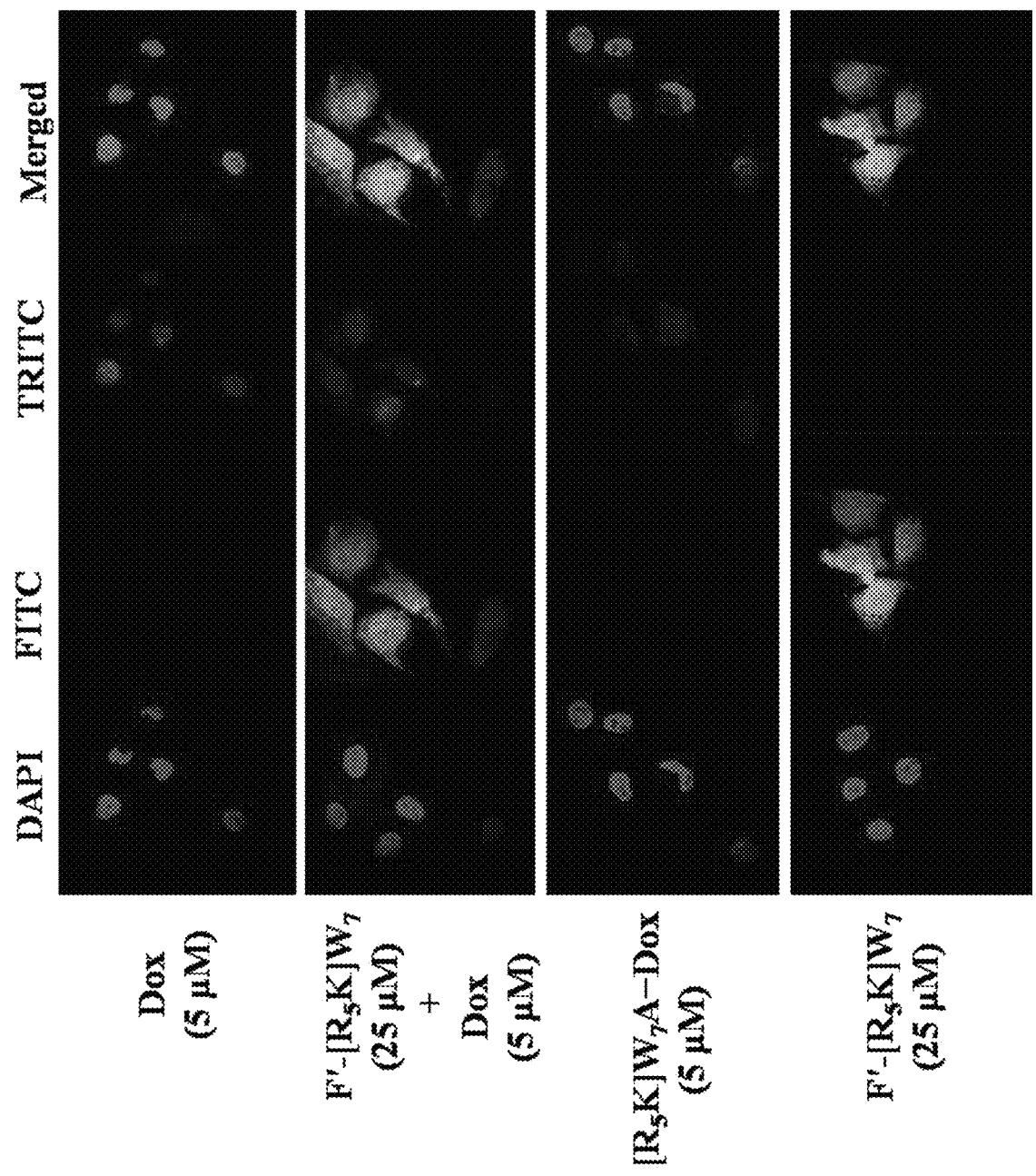
FIG. 15 depicts confocal microscopy images of Dox, [R₅K]W₇A-Dox (5 µM), F'-[R₅K]W₇ (25 µM)+Dox (5 µM) and F'-[R₅K]W₇ (25 µM) in SKOV-3 cells after 3 h. Red, blue, and green represent the fluorescence of Dox, the nucleus of the cells, and the fluorescent-labeled peptide, respectively.

To better understand the localization of the peptide and Dox in SK-OV-3 cells after 3 hours of incubation, the fluorescent-labeled peptide, F'-[R$_5$K]W$_7$ was used in the presence and absence of Dox. The images confirmed the localization of the peptide alone, mostly in the cytoplasm of the cells. The physical mixture of the peptide with Dox significantly increased the uptake of Dox in the cell nucleus (FIG. 15).

Figure 16:
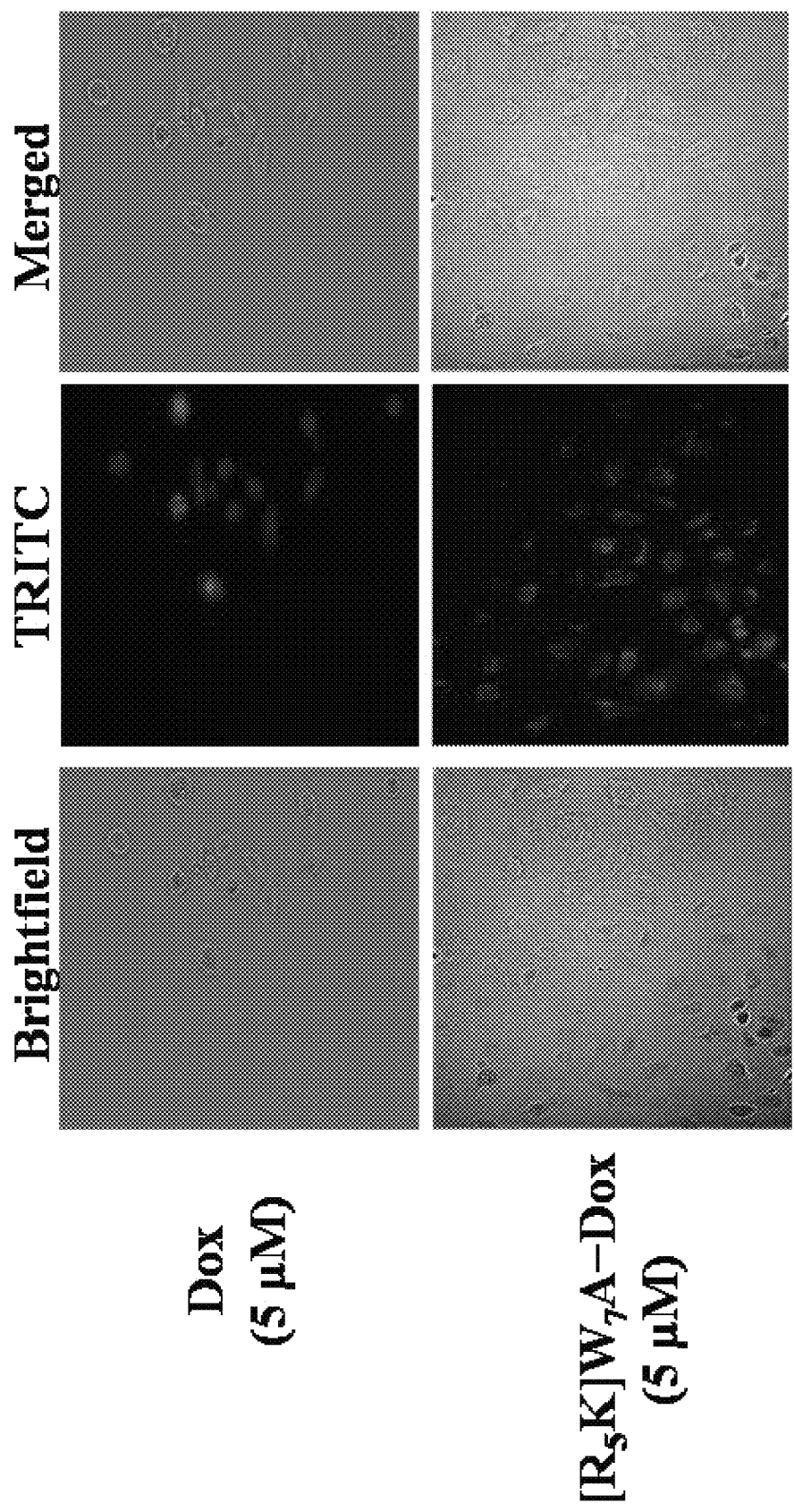
FIG. 16 depicts Fluorescence microscopy images of Dox and [R₅K]W₇A-Dox (5 µM) in SK-OV-3 cells after 24 h. Red represents the fluorescence of Dox.

Although [R$_5$K]W$_7$A-Dox was not significantly taken up by the cells after 3 h, fluorescence microscopy confirmed the internalization of [R$_5$K]W$_7$A-Dox (5 µM) in SK-OV-3 cells after 24 h of incubation (FIG. 16). Cells incubated with Dox at (5 µM) were also monitored as control after 24 h of incubation. Dox (5 µM) reduced the cell viability by 30% after 24 h (FIG. 8), which is also consistent with the images obtained by fluorescence microscopy, confirming the change in cells morphology as well as a reduction in cell viability in the presence of this anticancer agent; however, the cytotoxicity induced by [R$_5$K]W$_7$A-Dox (5 µM) was less than Dox alone after 24 h. The cell viability was only reduced by 19%; however, the images confirmed internalization of the peptide-Dox conjugate in SK-OV-3 cells after 24 h. The results are consistent with the results described above for the cytotoxicity studies, suggesting that the cytotoxicity of the peptide-Dox conjugate is time-dependent and is significantly increased after longer incubation times.

Figure 17:
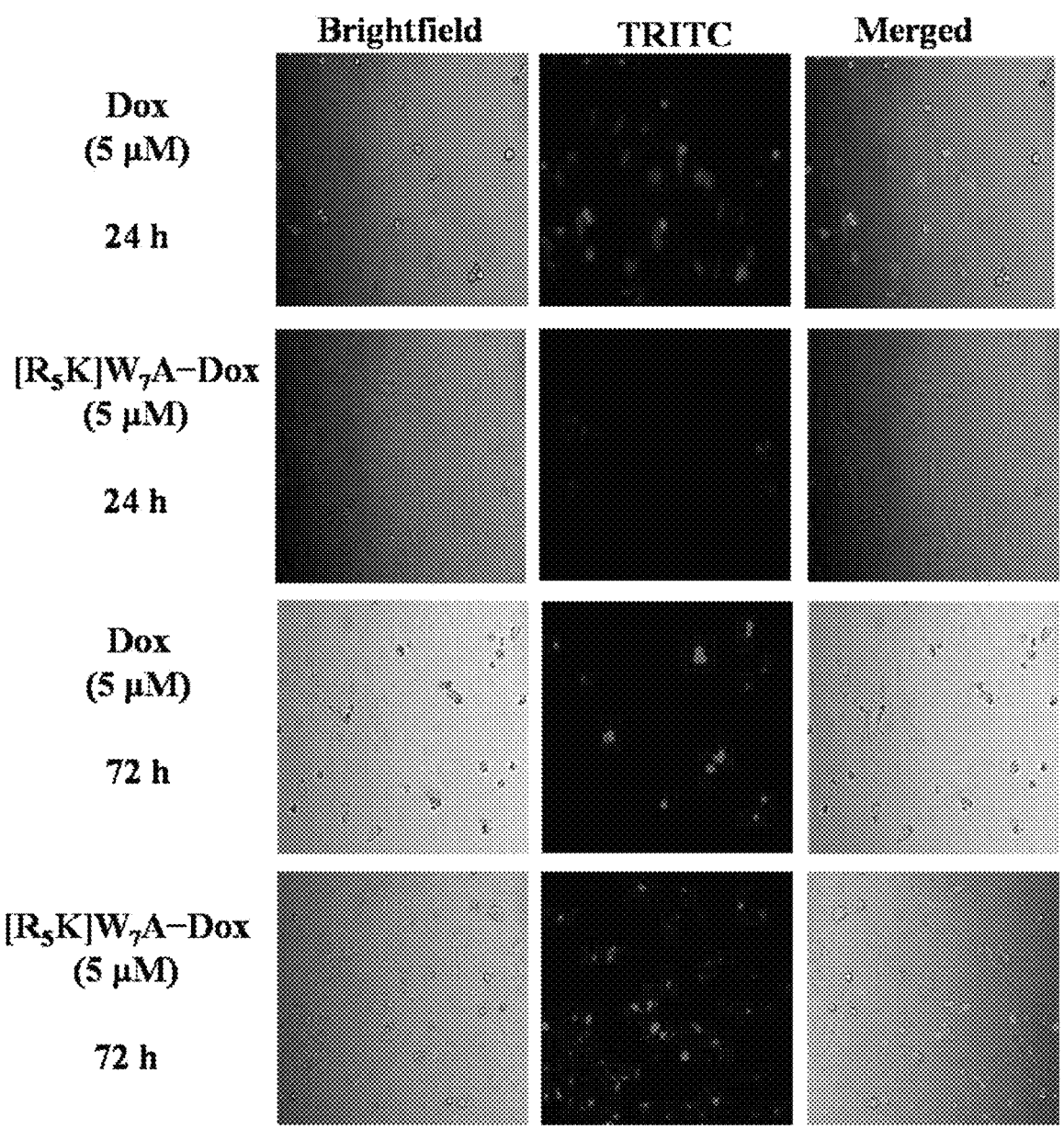
FIG. 17 depicts fluorescence microscopy images of Dox and [R₅K]W₇A-Dox (5 µM) cells after 24 and 72 h in normal heart cells. Red represents the fluorescence of Dox.

Microscopy of normal heart muscle cells are shown after 24 h and 72 h incubation of the cells in the presence of [R$_5$K]W$_7$A-Dox and free Dox at 5 µM concentration (FIG. 17). The fluorescence intensity of Dox in cells treated with [R$_5$K]W$_7$A-Dox was found to be significantly less than that in cells treated with Dox alone after 24 h and 72 h indicating that the peptide-Dox conjugate was not significantly uptaken by normal heart muscle cells. These data are consistent with the low cytotoxicity of the conjugate in heart cells as described above. The microscopy images along with the results obtained from the cell viability tests performed in normal heart muscle cells show promising results, indicating that [$R_5K$]$W_7$A-Dox (5 µM) does not significantly reduce the cell viability even after 72 h of incubation with the heart cells, compared with Dox (5 µM) that significantly reduces the cell viability and changes the cells morphology after 72 h; while [$R_5K$]$W_7$A-Dox conjugate (5 µM) is very cytotoxic to other cancer cell lines, such as leukemia and gastric cancer cells after 72 h.

Figure 18A:
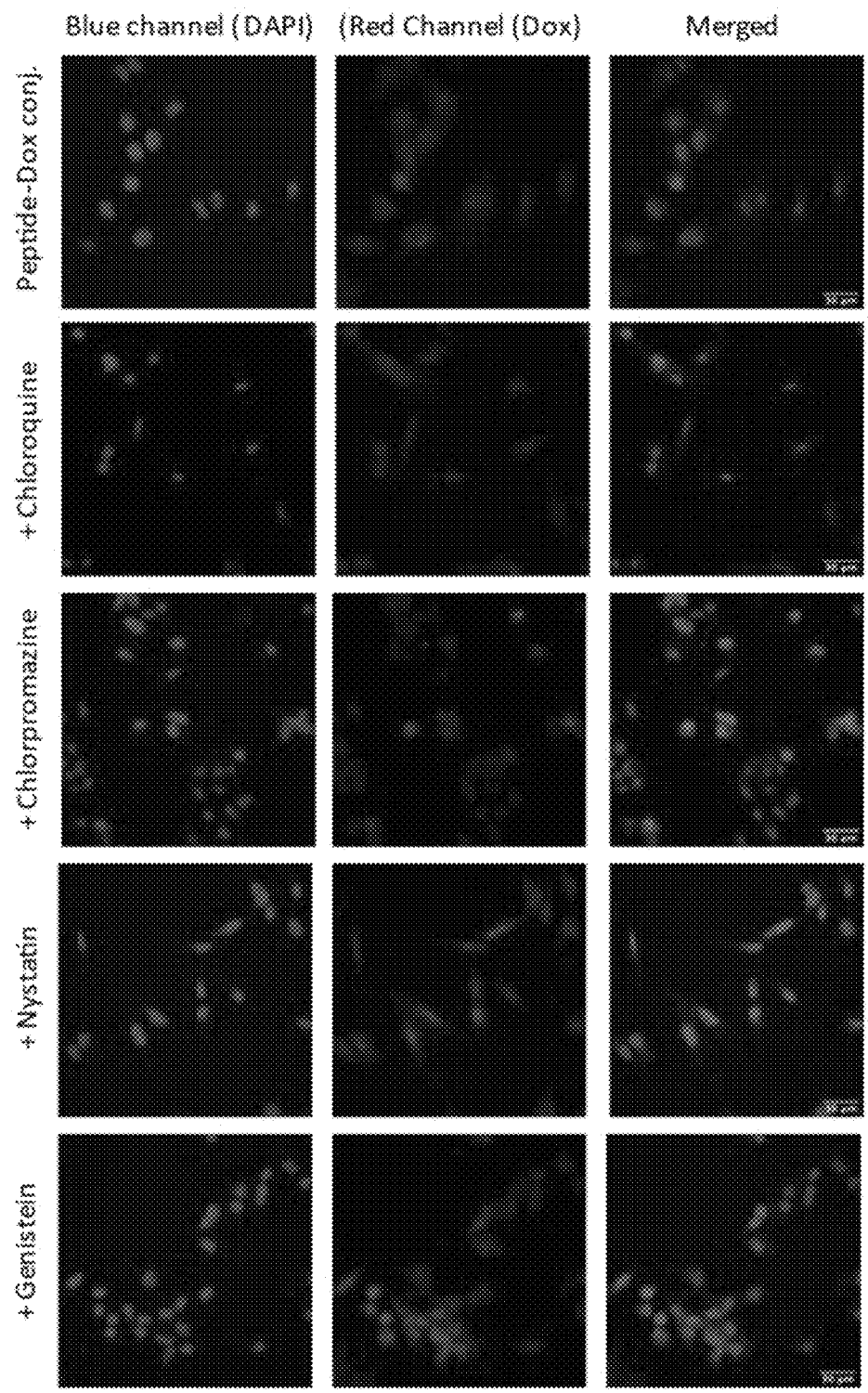
FIGS. 18A-B depict [R₅K]W₇-Dox uptake in MDA-MB-231 cells in the presence of different inhibitors of clathrin- and caveolae-dependent endocytosis by confocal microscopy (FIG. 18A) and flow cytometry (FIG. 18B).
Figure 18B:
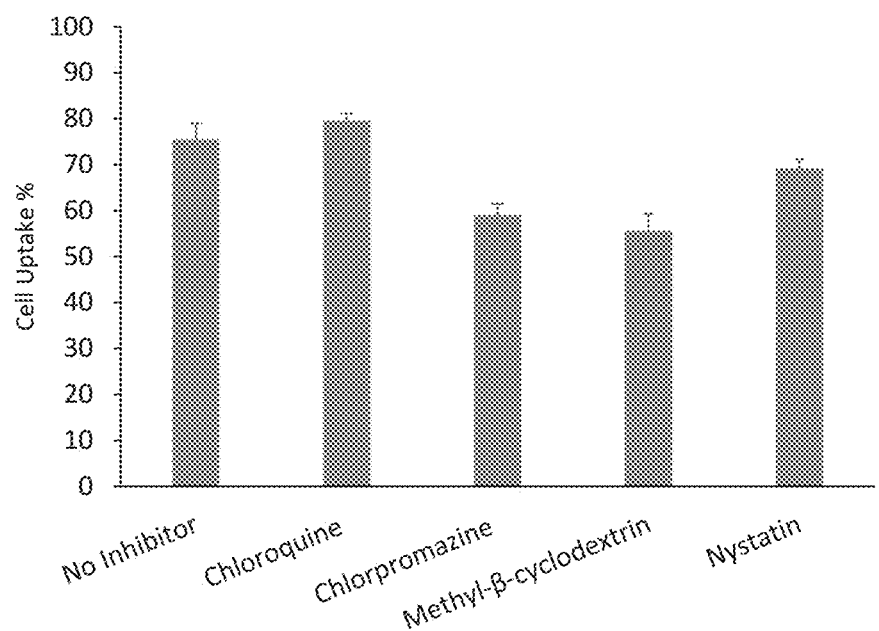

To determine whether the uptake of [$R_5K$]$W_7$A-Dox was endocytosis-dependent, the cellular uptake was examined in the presence and absence of a number of endocytosis inhibitors, nystatin, chloroquine, chlorpromazine, and genistein in MDA-MB-231 cells. The confocal microscopy demonstrated the localization of the conjugate in the nucleus with no change in the uptake in the presence of chloroquine, chlorpromazine, nystatin, and genistein. Flow cytometry showed a slight uptake reduction in the presence of chlorpromazine and methyl-β-cyclodextrin but no significant change in the presence of nystatin and chloroquine (FIG. 18). These data rule out clathrin-mediated and caveolae-mediated endocytosis as the main mechanism of uptake.

Stability of Conjugate [$R_5K$]$W_7$A-Dox

Conjugate [$R_5K$]$W_7$A-Dox was incubated with fetal bovine serum (FBS) solution at 37° C. at different time intervals. The stability results in the presence of 10% FBS suggested that after only 4 h of incubation, 55% of Dox is released. After 24 h of incubation, only 25% of the peptide-Dox conjugate remained intact.

Discussion

Dox is a widely used potent chemotherapeutic agent; however, its clinical application is limited because of its dose-dependent cardiotoxicity. Dox is one of the effective chemotherapeutic agents used for breast cancer, leukemia, and lymphoma treatment. However, the use of these drugs is restricted due to an 8-fold increase in the risk of potentially fatal cardiotoxicity. The mechanism of Dox's cardiotoxicity is complex and may involve oxidative, nitrosative, and nitrative stress, mitochondrial dysfunction/toxicity, dysregulation of various metabolic and lipid signaling pathways, activation of various stress kinases and cell death mechanisms, triggering of secondary inflammation and remodeling, eventually culminating in cardiac dysfunction and heart failure. Furthermore, Dox use for treating ovarian carcinoma, liver cancer, and stomach cancer has become challenging due to the development of resistance associated with it.

The comparative cytotoxicity studies of Dox (5 µM), [$R_5K$]$W_7$A-Dox (10 µM), physical mixture (peptide (10 µM)+Dox (5 µM)), and peptide alone (10 µM) are shown in Tables 2-7. Tables 8 and 9 summarize the antiproliferative activities for Dox (5 µM), physical mixture ([$R_5K$]$W_7$A (5 µM)+Dox (5 µM)), and [$R_5K$]$W_7$A-Dox alone (5 µM). The conjugate was shown to be less cytotoxic in heart and kidney cells even after 72 h. Dox and the physical mixture were found to maintain cytotoxicity in healthy heart and kidney cells. Peptide alone showed only minimal cytotoxicity in all cells. The conjugate and Dox were also more cytotoxic in AGS and CCR-CEM cells than SK-OV-3 cells. However, Dox and the physical mixture were more cytotoxic to heart and kidney cells after 72 h when compared with ovarian cancer cells.

In general, the cytotoxicity of [$R_5K$]$W_7$-Dox, Dox, and the physical mixture in cancer cells was time-dependent and was significantly higher after 72 h versus 24 h. The cytotoxicity of the peptide alone was concentration-dependent but not necessarily time-dependent.

As described above, the results confirmed minimal risk for cardiotoxicity of peptide-Dox conjugates. In contrast, free Dox reduced the viability of kidney (LLC-PK1) and heart muscle (H9C2) cells by 85% and 44%, respectively. [$R_5K$]$W_7$A-Dox exhibited minimal cytotoxicity to LLC-PK1 (5-7%) and H9C2 (<9%) cells at similar or higher concentrations.

Furthermore, the physical mixture of Dox 5 µM with peptide 5 µM generated a significant amount of toxicity in a Dox-resistant cell line, uterine sarcoma cells; however, Dox and the conjugate were not highly effective at 5 µM. On the other hand, the peptide alone (25 µM), the conjugate (25 µM), and the physical mixture of the peptide (25 µM) with Dox (5 µM) were all effective against Dox-Resistant cells.

TABLE 2

Cytotoxicity of linear $R_5KW_7$A-Dox, cyclic-linear [$R_5K$]$_7$A-Dox, and [$R_5K$]$W_7$C-S-S-Dox conjugates in CCRF-CEM cells determined by MTS assay.

| Compound | Cell Viability (%) after 24 h | Cell Viability (%) after 72 h |
|---|---|---|
| Cells | 100 ± 1 | 100 ± 3 |
| Water | 106 ± 1 | 98 ± 1 |
| Dox (5 µM) | 48 ± 2 | 15 ± 3 |
| [$R_5K$]$W_7$A-Dox (25 µM) | 36 ± 0 | 15 ± 1 |
| [$R_5K$]$W_7$A-Dox (10 µM) | 68 ± 0 | 13 ± 3 |
| [$R_5K$]$W_7$A-Dox (5 µM) | 74 ± 0 | 16 ± 6 |
| $R_5KW_7$A-Dox (25 µM) | 82 ± 1 | 18 ± 3 |
| $R_5KW_7$A-Dox (10 µM) | 86 ± 1 | 49 ± 8 |
| $R_5KW_7$A-Dox (5 µM) | 95 ± 0 | 77 ± 1 |
| [$R_5K$]$W_7$ (25 µM) + Dox (5 µM) | 35 ± 1 | 21 ± 4 |
| [$R_5K$]$W_7$ (10 µM) + Dox (5 µM) | 33 ± 0 | 19 ± 1 |
| [$R_5K$]$W_7$ (5 µM) + Dox (5 µM) | 40 ± 0 | 14 ± 4 |
| [$R_5K$]$W_7$ (25 µM) | 32 ± 0 | 24 ± 9 |
| [$R_5K$]$W_7$ (10 µM) | 68 ± 4 | 73 ± 6 |
| [$R_5K$]$W_7$ (5 µM) | 90 ± 1 | 68 ± 4 |
| [$R_5K$]$W_7$C-S-S-Dox (25 µM) | 71 ± 1 | 19 ± 1 |
| [$R_5K$]$W_7$C-S-S-Dox (10 µM) | 82 ± 2 | 74 ± 1 |
| [$R_5K$]$W_7$C-S-S-Dox (5 µM) | 87 ± 1 | 94 ± 3 |

TABLE 3

Cytotoxicity of cyclic-linear conjugate [$R_5K$]$W_7$A and [$R_5K$]$W_7$A-Dox in gastric adenocarcinoma cells using MTS assay.

| Compound | Cell Viability (%) after 24 h | Cell Viability (%) after 72 h |
|---|---|---|
| Cells | 100 ± 1 | 100 ± 3 |
| Water | 102 ± 1 | 95 ± 1 |
| Dox (5 µM) | 54 ± 2 | 13 ± 3 |
| [$R_5K$]$W_7$ (50 µM) | 79 ± 1 | 21 ± 1 |
| [$R_5K$]$W_7$ (25 µM) | 105 ± 2 | 76 ± 1 |
| [$R_5K$]$W_7$ (10 µM) | 104 ± 1 | 94 ± 2 |
| [$R_5K$]$W_7$ (5 µM) | 103 ± 3 | 108 ± 1 |
| [$R_5K$]$W_7$-Dox (50 µM) | 32 ± 1 | 11 ± 1 |
| [$R_5K$]$W_7$-Dox (25 µM) | 71 ± 0 | 10 ± 1 |
| [$R_5K$]$W_7$-Dox (10 µM) | 104 ± 5 | 13 ± 3 |
| [$R_5K$]$W_7$-Dox (5 µM) | 95 ± 0 | 27 ± 6 |
| [$R_5K$]$W_7$ (50 µM) + Dox (5 µM) | 31 ± 1 | 12 ± 3 |
| [$R_5K$]$W_7$ (25 µM) + Dox (5 µM) | 43 ± 5 | 12 ± 3 |
| [$R_5K$]$W_7$ (10 µM) + Dox (5 µM) | 41 ± 1 | 12 ± 4 |
| [$R_5K$]$W_7$ (5 µM) + Dox (5 µM) | 44 ± 0 | 11 ± 1 |

TABLE 4

Cytotoxicity of cyclic-linear conjugate [R$_5$K]W$_7$A and [R$_5$K]W$_7$A-Dox in ovarian cancer cells using MTS assay.

| Compound | Cell Viability (%) after 24 h | Cell Viability (%) after 72 h |
|---|---|---|
| Cells | 100 ± 1 | 100 ± 3 |
| Water | 92 ± 1 | 96 ± 1 |
| Dox (5 μM) | 73 ± 2 | 67 ± 3 |
| Dox (10 μM) | 71 ± 3 | 64 ± 1 |
| [R$_5$K]W$_7$-Dox (5 μM) | 87 ± 6 | 71 ± 3 |
| [R$_5$K]W$_7$-Dox (10 μM) | 87 ± 0 | 61 ± 6 |
| [R$_5$K]W$_7$-Dox (25 μM) | 76 ± 1 | 52 ± 3 |
| [R$_5$K]W$_7$ (5 μM) | 79 ± 1 | 102 ± 8 |
| [R$_5$K]W$_7$ (10 μM) | 76 ± 0 | 101 ± 1 |
| [R$_5$K]W$_7$ (25 μM) | 70 ± 6 | 81 ± 3 |
| [R$_5$K]W$_7$ (5 μM) + Dox (5 μM) | 67 ± 5 | 68 ± 3 |
| [R$_5$K]W$_7$ (10 μM) + Dox (5 μM) | 68 ± 5 | 69 ± 4 |
| [R$_5$K]W$_7$ (25 μM) + Dox (5 μM) | 51 ± 6 | 56 ± 3 |

TABLE 5

Cytotoxicity of cyclic-linear conjugate [R$_5$K]W$_7$A and [R$_5$K]W$_7$A-Dox in uterine sarcoma cells using MTS assay.

| Compound | Cell Viability (%) after 72 h |
|---|---|
| Cells | 100 ± 1 |
| Water | 116 ± 2 |
| Dox (5 uM) | 119 ± 5 |
| [R$_5$K]W$_7$ (25 μM) | 19 ± 2 |
| [R$_5$K]W$_7$ (10 μM) | 110 ± 4 |
| [R$_5$K]W$_7$Dox (5 μM) | 113 ± 1 |
| [R$_5$K]W$_7$-Dox (25 μM) | 23 ± 4 |
| [R$_5$K]W$_7$-Dox (10 μM) | 89 ± 2 |
| [R$_5$K]W$_7$-Dox (5 μM) | 97 ± 2 |
| [R$_5$K]W$_7$ (25 μM) + Dox (5 μM) | 11 ± 0 |
| [R$_5$K]W$_7$ (10 μM) + Dox (5 μM) | 13 ± 1 |
| [R$_5$K]W$_7$ (5 μM) + Dox (5 μM) | 51 ± 2 |

TABLE 6

Cytotoxicity of cyclic-linear conjugate [R$_5$K]W$_7$A-Dox in normal kidney cells determined by MTS assay in kidney cells.

| Compound | Cell Viability (%) after 24 h | Cell Viability (%) after 72 h |
|---|---|---|
| Cells | 100 ± 1 | 100 ± 3 |
| Water | 106 ± 1 | 98 ± 1 |
| Dox (5 μM) | 44 ± 0 | 33 ± 2 |
| [R$_5$K]W$_7$ (50 μM) | 71 ± 1 | 97 ± 3 |
| [R$_5$K]W$_7$ (25 μM) | 82 ± 1 | 97 ± 1 |
| [R$_5$K]W$_7$ (10 μM) | 86 ± 1 | 100 ± 1 |
| [R$_5$K]W$_7$ (5 μM) | 94 ± 1 | 98 ± 3 |
| [R$_5$K]W$_7$-Dox (50 μM) | 33 ± 1 | 33 ± 1 |
| [R$_5$K]W$_7$-Dox (25 μM) | 42 ± 0 | 94 ± 1 |
| [R$_5$K]W$_7$-Dox (10 μM) | 87 ± 0 | 95 ± 3 |
| [R$_5$K]W$_7$-Dox (5 μM) | 88 ± 0 | 93 ± 6 |
| [R$_5$K]W$_7$ (50 μM) + Dox (5 μM) | 39 ± 0 | 31 ± 3 |
| [R$_5$K]W$_7$ (25 μM) + Dox (5 μM) | 40 ± 1 | 31 ± 3 |
| [R$_5$K]W$_7$ (10 μM) + Dox (5 μM) | 41 ± 1 | 31 ± 8 |
| [R$_5$K]W$_7$ (5 μM) + Dox (5 μM) | 33 ± 0 | 30 ± 1 |

TABLE 7

Cytotoxicity of cyclic-linear conjugate [R$_5$K]W$_7$A-Dox and [R$_5$K]W$_7$C-S-S-Dox in normal heart muscle cells.

| Compound | Cell Viability (%) after 24 h | Cell Viability (%) after 72 h | Cell Viability (%) after 96 h |
|---|---|---|---|
| Cells | 100 ± 1 | 100 ± 3 | 100 ± 1 |
| Dox (5 μM) | 80 ± 2 | 56 ± 3 | 56 ± 1 |
| [R$_5$K]W$_7$-Dox (25 μM) | 68 ± 0 | 37 ± 1 | 39 ± 0 |
| [R$_5$K]W$_7$-Dox (10 μM) | 101 ± 0 | 105 ± 3 | 91 ± 0 |
| [R$_5$K]W$_7$-Dox (5 μM) | 100 ± 2 | 113 ± 6 | 115 ± 1 |
| [R$_5$K]W$_7$ (25 μM) + Dox (5 μM) | 46 ± 1 | 42 ± 3 | 48 ± 3 |
| [R$_5$K]W$_7$ (10 μM) + Dox (5 μM) | 67 ± 1 | 46 ± 3 | 58 ± 3 |
| [R$_5$K]W$_7$ (5 μM) + Dox (5 μM) | 72 ± 0 | 52 ± 1 | 61 ± 1 |
| [R$_5$K]W$_7$C-S-S-Dox (25 μM) | 92 ± 1 | 105 ± 2 | 108 ± 1 |
| [R$_5$K]W$_7$C-S-S-Dox (10 μM) | 91 ± 1 | 117 ± 1 | 113 ± 3 |
| [R$_5$K]W$_7$C-S-S-Dox (5 μM) | 98 ± 1 | 106 ± 1 | 104 ± 1 |

TABLE 8

Comparative cytotoxicity of Dox (5 μM), [R$_5$K]W$_7$A-Dox (10 μM), physical mixture (Peptide (10 μM) + Dox (5 μM), and peptide alone (10 μM).

| | Cell Viability (%) | | | | | | | | | |
|---|---|---|---|---|---|---|---|---|---|---|
| | CCRF-CEM (24 h) | CCRF-CEM (72 h) | AGS (24 h) | AGS (72 h) | SK-OV-3 (24 h) | SK-OV-3 (72 h) | H9C2 (24 h) | H9C2 (72 h) | LLCPK (24 h) | LLCPK (72 h) |
| Dox (5 μM) | 48 ± 2 | 15 ± 3 | 54 ± 2 | 13 ± 3 | 73 ± 2 | 67 ± 3 | 80 ± 2 | 56 ± 3 | 48 ± 2 | 15 ± 3 |
| [R$_5$K]W$_7$A-Dox (10 μM) | 68 ± 0 | 13 ± 3 | 104 ± 5 | 13 ± 3 | 87 ± 0 | 61 ± 6 | 101 ± 0 | 105 ± 3 | 87 ± 0 | 95 ± 3 |
| Physical Mixture ([R$_5$K]W$_7$A (10 μM) + Dox (5 μM)) | 33 ± 0 | 19 ± 1 | 41 ± 1 | 12 ± 4 | 68 ± 5 | 69 ± 4 | 67 ± 1 | 46 ± 3 | 41 ± 1 | 31 ± 8 |
| [R$_5$K]W$_7$A Alone (10 μM)) | 68 ± 4 | 73 ± 6 | 104 ± 1 | 94 ± 2 | 76 ± 0 | 101 ± 1 | 101 ± 0 | 105 ± 3 | 86 ± 1 | 100 ± 1 |

TABLE 9

Comparative cytotoxicity of Dox (5 μM), [R$_5$K]W$_7$A-Dox (5 μM), physical mixture (Peptide (5 μM) + Dox (5 μM), and peptide alone (5 μM) after 72 h incubation.

| | Cell Viability (%) | | | | | | | | | |
|---|---|---|---|---|---|---|---|---|---|---|
| | CCRF-CEM (24 h) | CCRF-CEM (72 h) | AGS (24 h) | AGS (72 h) | SK-OV-3 (24 h) | SK-OV-3 (72 h) | H9C2 (24 h) | H9C2 (72 h) | LLCPK (24 h) | LLCPK (72 h) |
| Dox (5 μM) | 48 ± 2 | 15 ± 3 | 54 ± 2 | 13 ± 3 | 73 ± 2 | 67 ± 3 | 80 ± 2 | 56 ± 3 | 44 ± 0 | 33 ± 2 |
| [R$_5$K]W$_7$A-Dox (5 μM) | 74 ± 0 | 16 ± 6 | 95 ± 0 | 27 ± 6 | 87 ± 6 | 71 ± 3 | 100 ± 2 | 113 ± 6 | 88 ± 0 | 93 ± 6 |

TABLE 9-continued

Comparative cytotoxicity of Dox (5 μM), [R₅K]W₇A-Dox (5 μM), physical
mixture (Peptide (5 μM) + Dox (5 μM), and peptide alone (5 μM) after 72 h incubation.

| | Cell Viability (%) | | | | | | | | | |
|---|---|---|---|---|---|---|---|---|---|---|
| | CCRF-CEM (24 h) | CCRF-CEM (72 h) | AGS (24 h) | AGS (72 h) | SK-OV-3 (24 h) | SK-OV-3 (72 h) | H9C2 (24 h) | H9C2 (72 h) | LLCPK (24 h) | LLCPK (72 h) |
| Physical Mixture ([R₅K]W₇A (5 μM) + Dox (5 μM)) | 40 ± 0 | 14 ± 4 | 44 ± 0 | 11 ± 1 | 67 ± 5 | 68 ± 3 | 72 ± 0 | 52 ± 1 | 33 ± 0 | 30 ± 1 |
| [R₅K]W₇A Alone (5 μM)) | 90 ± 1 | 68 ± 4 | 103 ± 3 | 108 ± 1 | 79 ± 1 | 102 ± 8 | — | — | 94 ± 1 | 98 ± 3 |

Conclusions

In summary, linear and cyclic-linear peptide-Dox conjugates were synthesized as prodrugs were evaluated for their activities against various cancer cell lines and were compared with the corresponding physical mixtures. [R₅K]W₇A-Dox conjugate demonstrated better antiproliferative activity when compared with [R₅K]W₇C—S—S-Dox and linear R₅KW₇A-Dox in CCRF-CEM cells. [R₅K]W₇A-Dox, exhibited comparable antiproliferative activity compared to Dox alone after 72 h incubation time in all cancer cell lines (CCRF-CEM, SK-OV-3, and AGS).

[R₅K]W₇A-Dox conjugate showed 16-fold and 9.5-fold higher activity against Dox-resistant cells MDA231R and MES-SA/MX2 when compared to free Dox, while the activities in MDA-MB-231WT was slightly lower (1.5 fold). These data indicate that the conjugate has the potential to be used as an alternative for Dox-resistant cells. The physical mixture of Dox with [R₅K]W₇A showed significant cytotoxicity in a Dox resistant cell line, uterine sarcoma, after 72 h incubation. Furthermore, [R₅K]W₇A-Dox conjugate significantly reduced the cell cytotoxicity after 72 h when compared with Dox alone in normal cell lines, such as heart muscle and kidney cells.

The microscopy images along with the results obtained from the cell viability test performed in heart muscle cells and kidney cells showed promising results indicating that cyclic [R₅K]W₇A-Dox (5 μM) does not significantly reduce the cell viability even after 72 h of incubation with the cells, compared with Dox (5 μM) that significantly reduced the cell viability and changed the cells morphology after 72 h; while conjugate [R₅K]W₇A-Dox (5 μM) is very cytotoxic to other cancer cell lines such as, leukemia and gastric cancer cells after 72 h. These data suggest that conjugate [R₅K]W₇A-Dox can be used as a potential prodrug for Dox-resistance cells and improving the side effects that are associated with Dox, such as damaging the heart muscle cells by causing cardiomyopathy.

Example 2. [(WR)₈WKβA]-Doxorubicin Conjugate

Synthesis of Cyclic Peptide [(WR)₈WKβA]. Fmoc solid-phase peptide synthesis followed by solution-phase cyclization was utilized to synthesize cyclic [(WR)₈WKβA]. Fmoc-Arg(Pbf)-OH, Fmoc-Trp(Boc)-OH, Boc-βAla-OH, and Dde-Lys(Fmoc)-OH were used as building block amino acids in the peptide synthesis. Preloaded resin, H-Trp(Boc)-2-chlorotrityl resin (0.44 meq/g, 0.4 mmol, 905 mg) was swelled in N,N-dimethylformamide (DMF) under dry nitrogen gas (3×15 min). After filtration of the solvent, the next Fmoc-protected amino acid (3 equiv.) was conjugated to the free N-terminal in the presence of 2-(1H-benzotriazol-1-yl)-1,1,3,3-tetramethyluronium hexafluorophosphate (HBTU) (3 equiv.) as a coupling reagent and N,N-diisopropylethylamine (DIPEA) (6 equiv.) as a base in DMF by agitating under dry nitrogen gas for 1 h. After the completion of the coupling, the reaction solution was filtered off. The resin was washed extensively with DMF (15 mL, 2×5 min). Fmoc deprotection was performed in the presence of piperidine in DMF (10 mL, 2×15 min, 20% v/v). The reaction solution was filtered off and the resin was washed with DMF (15 mL, 2×5 min). The subsequent amino acids were coupled and deprotected as described above. After the final coupling with Boc-βAla-OH, the resin was washed with DMF (3×25 mL, each time 5 min). Then, the Dde group at the N-terminal of lysine was deprotected by using hydrazine monohydrate (2% v/v) solution in DMF (3×20 mL, each time 10 min), and the resin was washed with DMF (5×50 mL) followed by washing with DCM (3×50 mL). The side chain-protected peptide was cleaved from trityl resin using a cleavage cocktail containing dichloromethane, trifluoroethanol, acetic acid (DCM:TFE:AcOH, 7:2:1 v/v/v, 50 mL), shaking for 2.5 h at room temperature to yield the side chain-protected linear peptide. The resin was collected by filtration and washed with TFE/DCM (2:8 v/v, 2×10 mL). The combined filtrates were evaporated under reduced pressure. Hexane (2×25 mL) and DCM (1×25 mL) were added to the residue to remove the acetic acid from the cleaved crude peptide. The crude peptide was obtained as a white solid and was dried in a vacuum overnight. The compound was directly used for the next cyclization reaction. The linear peptide was dissolved in anhydrous DMF/DCM (5:1 v/v, 250 mL). 1-Hydroxy-7-azabenzotriazole (HOAt, 223 mg, 1.64 mmol, 4 equiv) and N,N-diisopropylcarbodiimide (DIC, 290 μL, 1.86 mmol, 4.5 equiv.) were added to the mixture, and the solution was stirred at room temperature overnight. The completion of the cyclization was confirmed by MALDI-TOF. The solvent was removed by using a rotary evaporator under low pressure. The crude cyclic peptide was dried overnight, and a cleavage cocktail composed of trifluoracetic acid (TFA), anisole, thioanisole (9:1:2 v/v/v), and DTT (50 mg, dithiothreitol) (20 mL total volume) was mixed with the crude product for 6 h to remove the protecting groups on the side chains. Cold diethyl ether was added to precipitate the crude peptide, which was then centrifuged and separated. The molecular weight of the cyclic peptide was confirmed again with MALDI-TOF. The cyclic peptide was purified using RP-HPLC and lyophilized.

[(WR)₈WKβA]: MALDI-TOF (m/z): $C_{156}H_{203}N_{53}O_{19}$, calculated: 3122.6548. found: 3122.6093 [M]⁺.

Synthesis of N-Fmoc-Dox-14-O-Hemiglutarate. For the synthesis of N-Fmoc Dox derivative, Dox hydrochloride was dissolved in anhydrous DMF (5 mL) under a nitrogen atmosphere. Then Fmoc-OSu was slowly added to the reaction mixture, followed by dropwise addition of anhydrous N,N-diisopropylethylamine. After stirring the reaction overnight at room temperature and in dark conditions, the reaction was stopped and the solvent was removed. The oily liquid was triturated with TFA solution in water (0.1% v/v)

to yield a solid crystal. The solid was collected after filtration and washed with cold diethyl ether to remove traces of excess of Fmoc-OSu. The pure Fmoc-N-Dox was reacted with glutaric anhydride in the presence of anhydrous DIPEA in anhydrous DMF for 16 h under nitrogen atmosphere. The final compound was purified by HPLC to yield pure N-Fmoc-Dox-14-O-hemiglutarate.

[(WR)$_8$WKβA]-Dox Conjugate Synthesis. N-Fmoc-Dox-14-O-hemiglutarate (5 mg), cyclic peptide [(WR)$_8$WKβA] (10 mg), benzotriazole-1-yloxytripyrrolidinophosphonium hexafluorophosphate (PyBOP, 30 mg), and 1-hydroxybenzotriazole (HOBt, 30 mg) were added to the glass vial under nitrogen atmosphere. The mixture was stirred to dissolve the compounds, followed by the addition of DIPEA (80 μL) in anhydrous DMF (5 mL). The mixture was stirred for 2 h in dark conditions. The solvent was then removed, and cold diethyl ether was added to the residue. The crude cyclic peptide was precipitated and centrifuged to obtain the crude solid peptide-Dox conjugate. A solution of piperidine in DMF was used (20% v/v, 2 mL for 5 min) to remove the Fmoc protecting group. The solution color turned blue, and the reaction was terminated by adding drops of TFA solution in DMF (20% v/v) until the solution color turned red. The solvent was removed under reduced pressure. The product was then dissolved in acetonitrile/water (50% v/v). The final product was purified using HPLC and characterized by using MALDI-TOF.

[(WR)$_8$WKβA]-Dox: MALDI-TOF (m/z): $C_{187}H_{234}N_{54}O_{32}$ calculated: 3747.8343. found: 3747.8257 [M]$^+$, 3225.2231 [[(WR)$_8$WKβA]-Glutarate+3H]$^+$.

In Vitro Cytotoxicity Assay of [(WR)$_8$WKβA]-Dox Conjugate. Cytotoxic activity of the synthesized conjugate and noncovalent mixtures of cyclic [WR]$_9$+Dox was determined in SK-OV-3, MDA-MB-231, MCF-7, MES-SA/MX2, and H9C2 cells. In brief, the cells were seeded at 5000 cells (0.1 mL per well in 96-well plates). An appropriate growth medium was used for each cell line (for SK-OV-3: McCoy's SA with L-glutamine containing fetal bovine serum (FBS) (10%) and penicillin or streptomycin (1%); for MDA-MB-231 and MCF-7 cells: DMEM/F12 (1:1) (1×) with L-Glutamine and 15 mM HEPES containing FBS (10%) and penicillin or streptomycin (1%), and for MES-SA/MX2 and H9C2 cells: Minimum Essential Medium Eagle with Earle's salts and sodium bicarbonate, without L-glutamine containing FBS (10%), and penicillin or streptomycin (1%)). The cells were seeded in a complete growth medium 24 h prior to the experiment. The compounds at different concentrations (1-10 μM) were added to each well in triplicate and incubated for 24 h and 72 h at 37° C. in a humidified atmosphere of 5% $CO_2$. Dox (5 μM) was used as a positive control, while water and cell culture medium were used as negative controls. The compounds were dissolved in water; water was used as a negative control to normalize the data. After the incubation period, MTS reagent (20 μL) was added to each well. The incubation was continued for 3 h. Cell viability was then measured by the determination of the fluorescence intensity at 490 nm using a SpectraMax M2 microplate spectrophotometer. The percentage of cell viability was then calculated using the following equation:

[(OD value of cells treated with the compound)−(OD value of culture medium)]/[(OD value of control cells)−(OD value of culture medium)]×100%.

Confocal Microscopy. MDA-MB-231, SK-OV-3, MES-SA/MX2, and H9C2 cells (7×10$^4$ cells/well) were seeded with a medium on a coverslip 24 h prior to the experiment in six well plates. After 24 h, the medium was changed with opti-MEM. The cells were treated with Dox and peptide-Dox conjugate (5 μM) in opti-MEM for 24 h. After 24 h incubation, the media were removed, and cells were washed three times with PBS in each well. Then, the cells were fixed with 3.7% formaldehyde for 10 min, followed by washing three times with PBS (pH 7.6) for 5 min. DAPI (40 μL) for staining the nuclei was placed on a microscope slide, and it was covered with the coverslip with the cell-attached side facing down. The slides were left standing horizontally in a dark place with airflow to allow faster drying. The cells were photographed using Nikon Instruments A1 Confocal Laser Microscope Series and NIS-Elements software (AR 4.30.02, 64 bit). The scan mode was selected as Galvano. The magnification and resolution were set at 40× and 1024, respectively.

Differential Extraction of Dox in Nuclear and Cytoplasmic Compartments. In order to confirm nuclear delivery of peptide-conjugated Dox, in addition to confocal microscopy, a differential nuclear and cytoplasmic extraction was performed. Cells were exposed to (50 μM) free and conjugated Dox for 4 h and incubated at 37° C. in a humidified atmosphere of 5% $CO_2$. The cells were then pelleted at 2000 rpm for 5 min. After removing the supernatant, the cells were resuspended in Dounce buffer containing protease inhibitors. The cell suspension to be used was incubated on ice for 15 min before being spiked with cold 10% NP-40 and vortexed for 10 s. The suspension was centrifuged at 10,000 rpm for 10 min at 4° C. to pellet the nuclei. The supernatant was isolated for cytoplasmic extraction. The nuclear pellet was washed in cold PBS twice and centrifuged to remove the supernatant. The isolated nuclei were then lysed using RIPA buffer containing protease inhibitors. The nuclear and cytoplasmic extractions were analyzed by analytical HPLC to differentially quantify free Dox (or Dox released from the conjugates) and peptide-conjugate Dox using an Agilent Zorbax SB-C18 (4.6×150 mm) column. The column was equilibrated with 0.1% TFA-water (solvent A). The elution was performed at a flow rate of 1 mL/min using a gradient of acetonitrile from 0 to 35% in 50 min, with the absorbance measured at 490 nm.

Fluorescence-Activated Cell Sorter (FACS) Analysis of Cellular Uptake in the Presence of Endocytosis Inhibitors. A flow cytometry study was conducted in the presence of endocytosis inhibitors such as nystatin, chlorpromazine, chloroquine, and methyl β-cyclodextrin to determine whether the cellular uptake for the peptide-Dox was endocytosis-dependent. MDA-MB-231 (5×10$^5$ cells/well) were seeded in the medium 24 h prior to the experiment in six well plates, and after 24 h the medium was changed with Opti-MEM. The cells were preincubated by various endocytosis inhibitors including nystatin (50 μg/mL), chloroquine (100 μM), chlorpromazine (30 μM), and methyl-β-cyclodextrin (2.5 mM) for 30 min at 37° C. in a humidified atmosphere of 5% $CO_2$. The cells were then incubated with [(WR)$_8$WKβA]-Dox conjugate (5 μM) in the presence of inhibitors. After 3 h incubation, the media containing the compounds were removed. Next, the cells were digested with 0.05% trypsin/EDTA (0.53 mM) for 5 min to remove any artificial surface binding, centrifuged at 2500 RPM for 5 min, and then collected as the precipitant. Then the cells were washed two times with PBS, resuspended in flow cytometry buffer, and transferred to the flow cytometry tubes through the 35 μm Strainer Mesh cap. Finally, the cells were analyzed by flow cytometry (FACSCalibur Becton Dickinson) using the propidium iodide channel and CellQuest software. The data presented were based on the mean fluorescence intensity for 10,000 cells collected. All assays were performed in triplicate.

Stability Studies. Human serum (250 μL) was diluted by adding sterile water (650 μL) and conjugate stock solution (100 μL) to give a sample with 25% human serum and 5 μM conjugate. The sample was kept at 37° C. in an incubator to mimic human body temperature. At regular time intervals, aliquots (100 μL) were taken and diluted with methanol (200 μL). After centrifugation (7000 RPM) of the mixture for 10 min, the supernatant was analyzed by analytical HPLC at 495 nm, and the major HPLC peaks were analyzed by mass spectrometry. The mobile phase used was acetonitrile/water with 0.1% TFA, with a gradient of 20-45% and a flow rate of 1 mL/min in 50 min. The percentage of intact conjugate and the release of the free drug were plotted against incubation time. The AUC obtained after each run was used to confirm the conjugate's degradation, and $t_{1/2}$ (the time needed to hydrolyze half of the initial conjugate in human serum) was calculated from the graph plotted as AUC versus incubation time.

Intracellular Hydrolysis. Intracellular hydrolysis of [(WR)$_8$WKβA]-Dox and accumulation of free Dox and the peptide-Dox conjugate were determined in CCRF-CEM cells by HPLC analysis. Cells were grown with serum-free RPMI medium in 75 cm$^2$ culture flasks to approximately 70-80% confluence (1.37×10$^7$ cells/mL). The medium was first replaced with fresh RPMI medium having [(WR)$_8$WKβA]-Dox conjugate (5 μM). Then the cells were incubated at 37° C. After 4 h, the medium containing the conjugate was aspirated, and cells were washed three times with PBS before adding a fresh serum-free medium. The cells were first partitioned/transferred to culture plates (six wells) contained 1.37×10$^7$ cells per well in 5 mL of medium, then incubated for the indicated time. After incubation, the cells were collected using centrifugation. After centrifugation, the medium was removed by decantation. The cell pellets were washed with ice-cold PBS to remove any remaining medium. The cell pellets were then completely extracted with an equal volume of methanol, chloroform, and isopropanol mixture (4:3:1 v/v/v) and finally filtered through 0.2 μm filters. The relative amount of Dox and [(WR)$_8$WKβA]-Dox concentrations in cell lysates were quantified by analytical HPLC using the water/acetonitrile solvent.

Data Analysis. The data are presented as the mean standard deviation for the stated number of samples. A significant difference test was performed using student's t-test between two groups. For data over three groups, one-way ANOVA and post hoc Tukey tests were performed. The alpha threshold was set to 0.05 with a 95% confidence interval.

Results

Chemistry

Fmoc solid-phase peptide synthesis followed by solution-phase cyclization was utilized to synthesize cyclic [(WR)$_8$WKβA]. The linear protected peptide (Dde-K(Boc-βA)(W(Boc)$_9$R(Pbf)$_8$) was assembled on the H-Trp(Boc)-2-chlorotrityl resin. The Dde group of N-terminal lysine was then deprotected in the presence of hydrazine (2% in DMF). The side chain-protected peptide was cleaved from the resin using AcOH/TFE/DCM (1:2:7, v/v/v) cocktail. The cyclization of the side chain-protected peptide was performed under pseudo-dilute conditions in the presence of HOAt and DIC (FIG. 20). The cyclic peptide was cleaved in the presence of reagent R, purified using reversed-phase HPLC, and used for conjugation with Dox.

N-Fmoc-Dox-14-O-hemiglutarate was prepared as follows. In brief, the reaction of Fmoc-protected Dox with glutaric anhydride was carried out to produce the Fmoc-Dox hemiglutarate ester with a free COOH, which after HPLC purification and lyophilization was used for coupling with fully deprotected cyclic peptide [(WR)$_8$WKβA]. The conjugation of the cyclic peptide with N-Fmoc-Dox-14-O-hemiglutarate was achieved by a similar pattern. The equimolar amounts of the peptide and Dox were coupled through the reaction of the free amino group of [(WR)$_8$WKβA] and carboxylic acid in the Fmoc-Dox hemiglutarate ester. The carboxylic group in Fmoc-protected Dox was pre-activated in the presence of HOBt/PyBOP/DIPEA in DMF for 15 min before reaction with the peptides. After conjugation, the Fmoc protecting group of Dox was removed using piperidine and was then acidified to yield [(WR)$_8$WKβA]-Dox conjugate (FIG. 21) that was purified using HPLC and lyophilized. The structures of all the final compounds were confirmed using a high-resolution MALDI-TOF/TOF mass spectrometer. The purity of the final product (≤95%) was confirmed by reversed-phase analytical HPLC using a gradient system with water (0.1% TFA) and acetonitrile as eluting solvents.

Antiproliferative Activity of [(WR)$_8$WKβA]-Dox Conjugate.

The cytotoxicity of the synthesized conjugate was evaluated in SK-OV-3, triple-negative breast cancer (TNBC) wild-type MDA-MB-231 and MCF-7 cells, and multidrug resistance (MDR) MES-SA/MX2 cells to determine the effect of the peptide conjugation on antiproliferative efficacy in sensitive and resistant cell lines. The activity of synthesized conjugate (1, 5, and 10 μM) was evaluated in a comparative study with the noncovalent physical mixture of [WR]$_9$ (1, 5, and 10 μM)+Dox (5 μM) and Dox alone (5 μM). Example 1 describes the synthesis and evaluation of hybrid cyclic linear [R$_5$K]W$_7$A-Dox conjugate in different cancer cell lines. The rationale for designing [(WR)$_8$WKβA]-Dox conjugate was based on the fact that the cyclic peptide [WR]$_9$ composed of alternate R and W was found to be a more potent kinase inhibitor than [WR]$_5$ and [R$_5$K]W$_7$ against c-Src, Abl, PKCa, Braf, Cdk2/cyclin A1, and that Lck. [WR]$_9$ was a superior molecular transporter versus [WR]$_5$. A Dox conjugate of [(WR)$_8$WKβA], a derivative of [WR]$_9$, with a large cyclic ring of alternate R and W residues would have a higher antiproliferative activity than [R$_5$K]W$_7$A-Dox and [W(RW)$_4$]-Dox, as Dox conjugates of [R$_5$K]W$_7$ and [WR]$_5$, respectively.

Figure 22A:
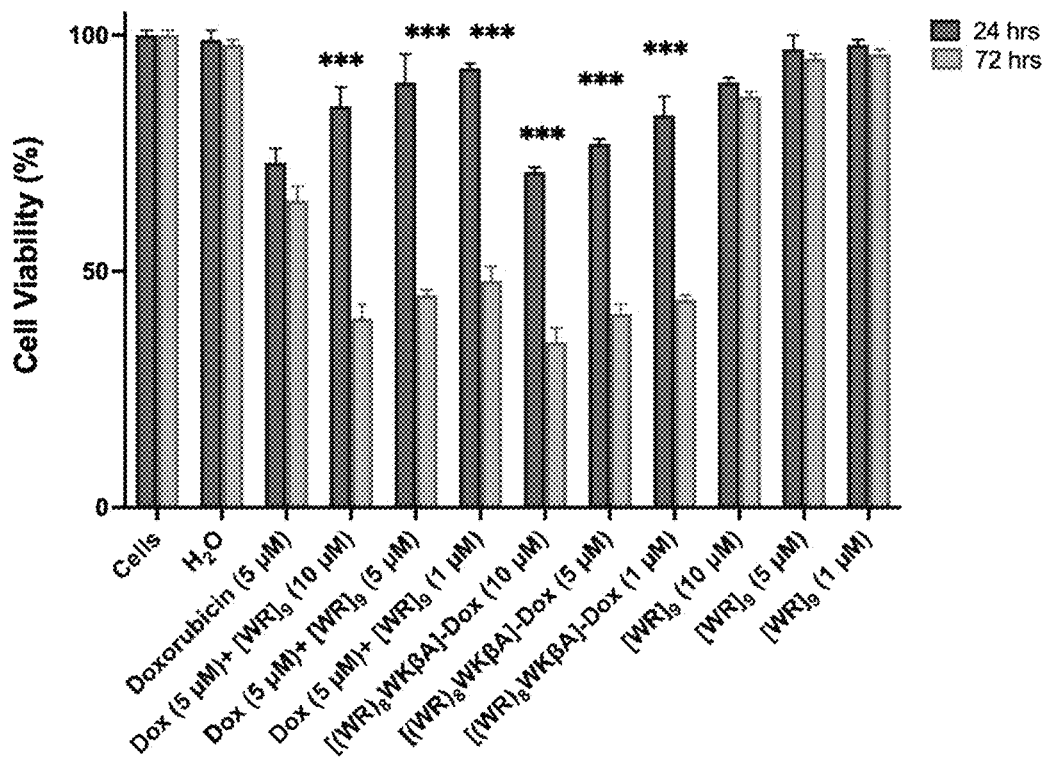
FIGS. 22A-D depict inhibition of SK-OV-3 (FIG. 22A), MDA-MB-231 (FIG. 22B), MCF-7 (FIG. 22C), and MES-SA/MX2 (FIG. 22D) cells (Dox-resistant cells) by free Dox (5 µM) or (1, 5, 10, and 20 µM), [(WR)₈WKβA]-Dox, [WR]₉+Dox, and [WR]₉ at 1, 5, and 10 mM. Results are mean±SD (n=3) (* p<0.05,  p<0.01, * p<0.001 treatment vs. Ctrl (Dox), p-value only for treatment after 72 h).

SK-OV-3 cells were exposed to [(WR)$_8$WKβA]-Dox, [WR]$_9$+Dox at 1, 5, and 10 mM and Dox alone at 5 mM, as shown in FIG. 22A. In general, the antiproliferative activities of [(WR)$_8$WKβA]-Dox and the physical mixture [WR]$_9$+Dox were found to be time-dependent. When compared to free Dox, all treatment groups showed low antiproliferative activity after 24 h. However, the cell proliferation inhibitory activity of compounds was enhanced at a longer period of incubation (72 h) of compounds with SK-OV-3 cells, presumably due to the time-dependent hydrolysis of the [(WR)$_8$WKβA]-Dox conjugate or time needed for the encapsulated Dox in the physical mixture [WR]$_9$+Dox to release free Dox. [(WR)$_8$WKβA]-Dox conjugate was able to reduce the SK-OV-3 cell viability by 65%, 59%, and 56% at 10 μM, 5 μM, and 1 μM, respectively, after 72 h compared to Dox, which reduced the viability by 35% at 5 μM after 72 h incubation. Previously in this cell line at 72 h incubation, the cyclic [W(RW)$_4$]-Dox inhibited the cell proliferation by 51% at a concentration of 1 μM, whereas [R$_5$K]W$_7$A-Dox was able to reduce the cell viability by 29%, 39%, and 48% at 5 μM, 10 μM, and 25 μM, respectively. A similar pattern was observed when the physical mixture of [WR]$_9$ and Dox was used. [WR]$_9$ showed higher antiproliferative at 10 μM, 5 μM, and 1 μM when used with Dox at 5 μM, showing 40%, 45%, and 48% viability, respectively, when compared with free Dox alone after 72 h incubation. The peptide alone exhibited minimal cytotoxicity (90-98% viability) after 24 h at 10 μM, 5 μM, and 1 μM and (87-96% viability) at 72 h.

The main option for the treatment of triple-negative breast cancer (TNBC) is chemotherapy. However, its efficacy has been seriously compromised due to the development of multidrug resistance (MDR). Therefore, to test the therapeutic efficacy of [(WR)$_8$WKβA]-Dox conjugate, cell cytotoxicity was evaluated using two TNBC cell lines (MDA-MB-231 and MCF-7).

Figure 22B:
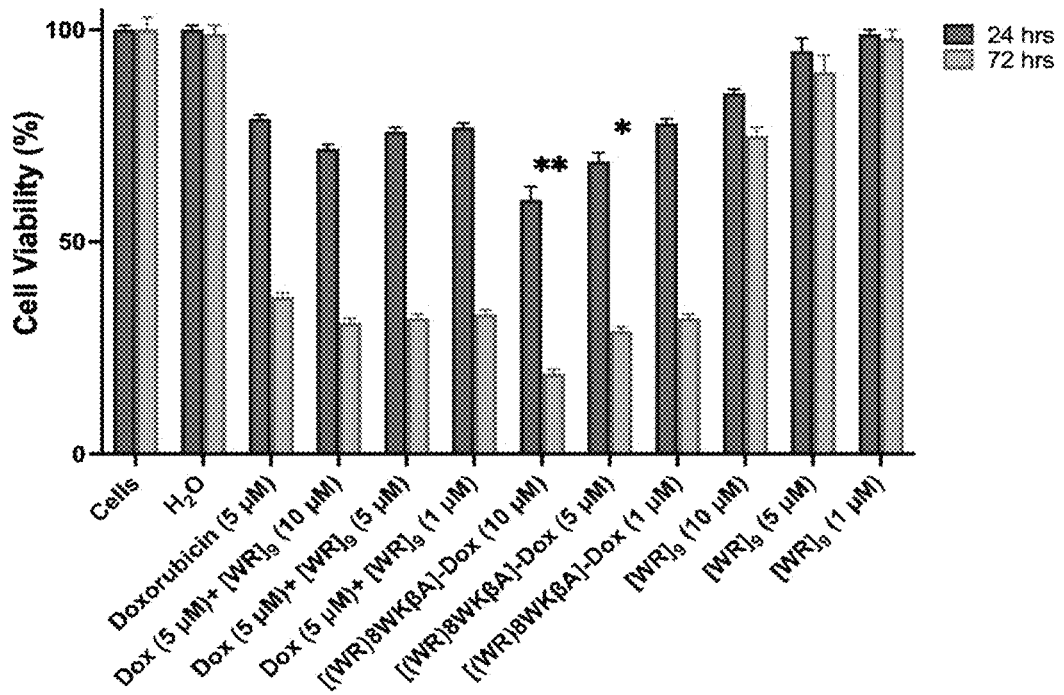

Cell viability was studied in MDA-MB-231 cells with different concentrations of [(WR)$_8$WKβA]-Dox and [WR]$_9$ (1 μM, 5 μM, and 10 μM)+Dox (5 μM), and Dox alone at 5 μM, as shown in FIG. 22B. After 24 h, [(WR)$_8$WKβA]-Dox showed lower cell viability of 60% and 69% at 10 μM and 5 μM, respectively, when compared with the conjugate showing cell viability of 79% at 1 μM. Dox alone showed 79% viability at 5 μM. The physical mixture of [WR]$_9$+Dox did not significantly reduce the viability of MDA-MB-231 cells compared to Dox after 24 h incubation. However, the antiproliferative activity of all compounds was enhanced at the 72 h incubation period. [(WR)$_8$WKβA]-Dox conjugate showed significantly high antiproliferative activity against MDA-MB-231 cells, with only 19% and 29% cell viability at 10 μM and 5 μM, respectively. Interestingly, [(WR)$_8$WKβA]-Dox conjugate showed comparable antiproliferative activity at 1 μM with 32% viability compared to control free Dox alone, which generated 37% viability. With 31-33% viability, the physical [WR]$_9$+Dox mixture did not significantly reduce cell viability compared to control Dox alone after 72 h incubation. [WR]$_9$ alone showed minimal cytotoxicity (85-98% viability) after 24 h at 10 μM, 5 μM, and 1 μM and (75-98% viability) at 72 h. These data indicate that [(WR)$_8$WKβA]-Dox conjugate has significantly higher antiproliferative activity against TNBC MDA-MB-231 than either Dox alone or the corresponding physical mixture when compared at similar concentrations and incubation times.

Figure 22C:
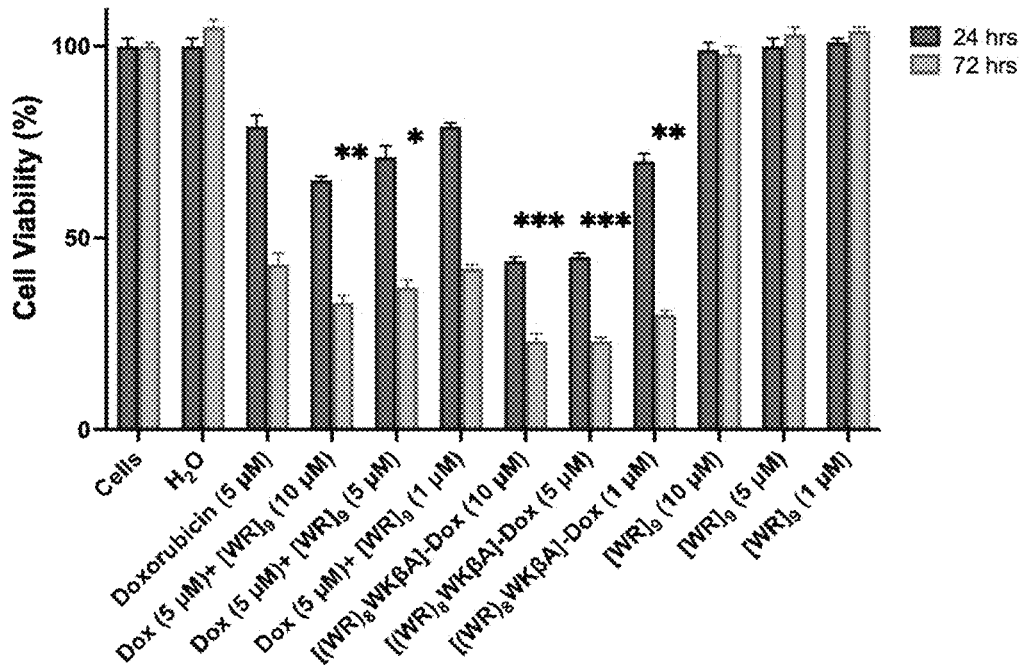

FIG. 22C depicts a cell viability study in MCF-7 cells with [(WR)$_8$WKβA]-Dox (1 μM, 5 μM, and 10 μM), physical mixture [WR]$_9$ (1 μM, 5 μM, and 10 μM)+Dox (5 μM), and Dox alone at 5 μM. The conjugate showed significant antiproliferative activity when incubated with cells for 24 h and 72 h at 10 μM and 5 μM. After 24 h, the conjugate reduced the cell proliferation by 56%, 55%, and 28% at 10 μM, 5 μM, and 1 μM, respectively, while Dox (5 μM) decreased proliferation by 21%. After 72 h, cell proliferation reduced by 77%, 77%, and 70% at 10 μM, 5 μM, and 1 μM, respectively, compared to 57% for Dox. A physical mixture of [WR]$_9$ with Dox showed a significant reduction of 67% and 63% in cell viability after 72 h at 10 μM and 5 μM, respectively, while the physical mixture of [WR]$_9$ (1 μM) with Dox (5 μM) demonstrated a comparable viability percentage to Dox alone. [WR]$_9$ at different concentrations showed no significant effect on cell survival. These data further confirm that [(WR)$_8$WKβA]-Dox is more effective against TNBC MCF-7 cells than Dox and the corresponding physical mixtures.

The overexpression of ATP-dependent efflux pump membrane proteins such as P-gp is the most frequent mechanism reported for Dox resistance. P-gp overexpression efficiently removes Dox and reduces its intracellular concentration. Thus, the efficacy of [(WR)$_8$WKβA]-Dox conjugate in MDR cancer cells was investigated to explore the possibility of overcoming resistance to Dox as a result of overexpression of efflux membrane proteins.

Figure 22D:
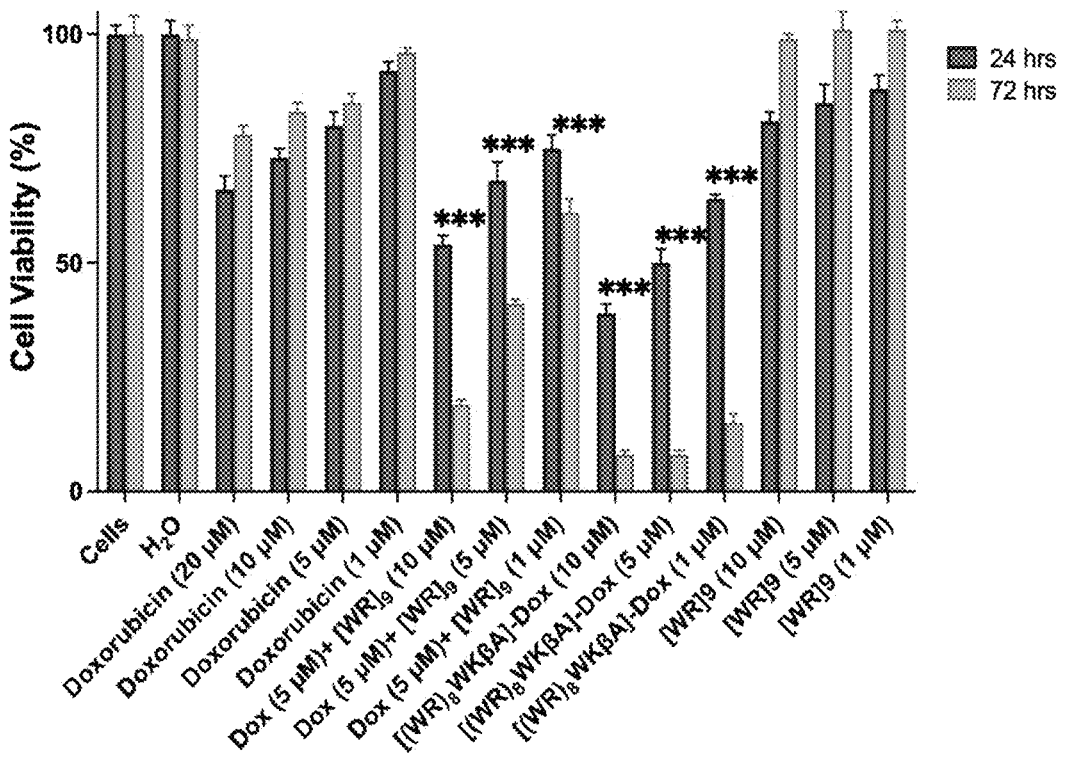

Uterine sarcoma cell line MES-SA/MX2 overexpresses P-gp and is a substrate for small molecules drugs such as Dox. [(WR)$_8$WKβA]-Dox conjugate and [WR]$_9$+Dox were significantly more effective than Dox alone (1 μM, 5 μM, 10 μM, or 20 μM) in Dox-resistant MES-SA/MX2 cells. As expected, free Dox at 1 μM, 5 μM, 10 μM, or 20 μM did not show significant efficiency against MES-SA/MX2, as shown in FIG. 22D, while the conjugate was significantly more potent. At 24 h, the conjugate showed a significant reduction in cell viability by 39%, 50%, and 64% at 10 μM, 5 μM, and 1 μM, respectively, as shown in FIG. 22D. The antiproliferative activity for [(WR)$_8$WKβA]-Dox conjugate was significantly increased after 72 h, with only 8%, 8%, and 15% Dox-resistant cell survival at 10 μM, 5 μM, and 1 μM, respectively, compared to 85% for control Dox alone. Previously, it was found that [R$_5$K]W$_7$A-Dox conjugate exhibited minimal cytotoxicity (0-10%) after 72 h at 5 μM and 10 μM, whereas it was found to significantly reduce the cell viability by almost 80% at 25 μM. In addition, [WR]$_9$+Dox mixture demonstrated significantly higher antiproliferative activity than Dox at 24 h and 72 h. However, the activities of the physical mixtures were less than [(WR)$_8$WKβA]-Dox conjugate. The maximum antiproliferative activity for the physical mixture was observed at a 1:2 ratio (5 μM:10 μM) of Dox:[WR]$_9$, which showed 46% and 71% reduction in cell survival after 24 and 72 h, respectively. The physical mixture in 1:1 ratio (5 μM:5 μM) of Dox:[WR]$_9$ showed significantly diminished cell viability, with 32% and 60% after 24 h and 72 h, respectively, while [WR]$_9$ alone had no significant antiproliferative effect after 24 h and 72 h.

Figure 29:
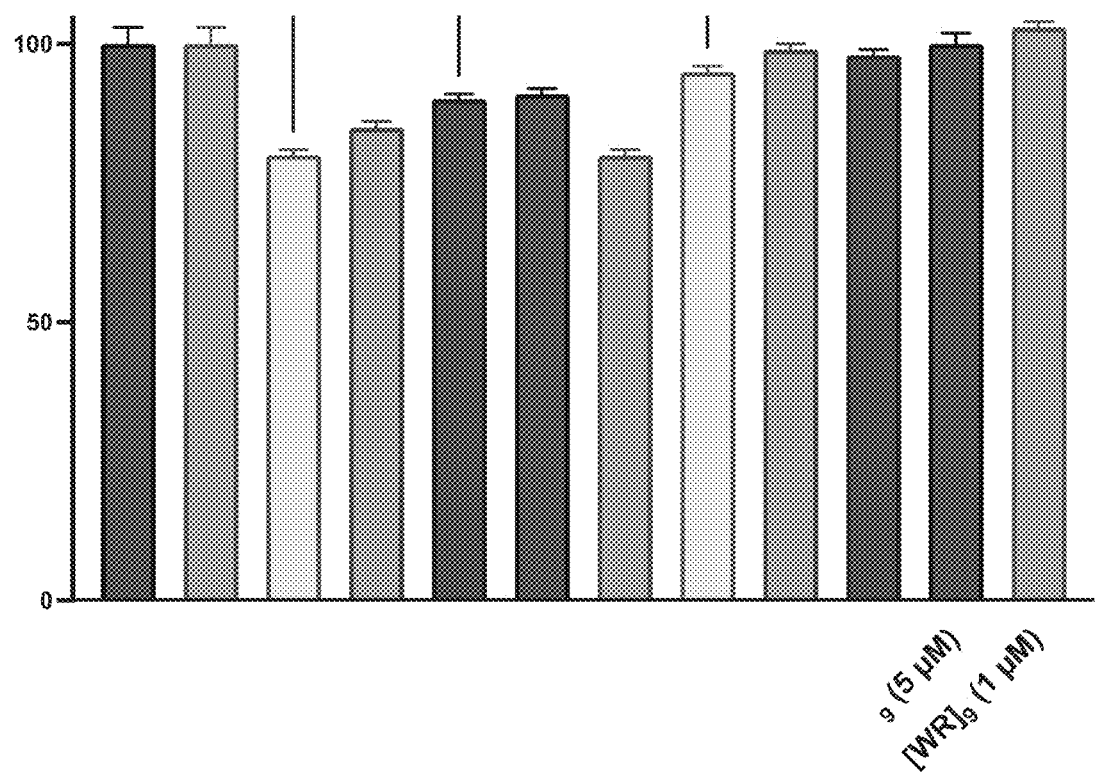
FIG. 29 depicts inhibition of heart cells (H9C2) by free Dox (5 µM), [(WR)₈WKβA]-Dox, [WR]₉+Dox, and [WR]₉ at 1, 5, and 10 µM.
Figure 30:
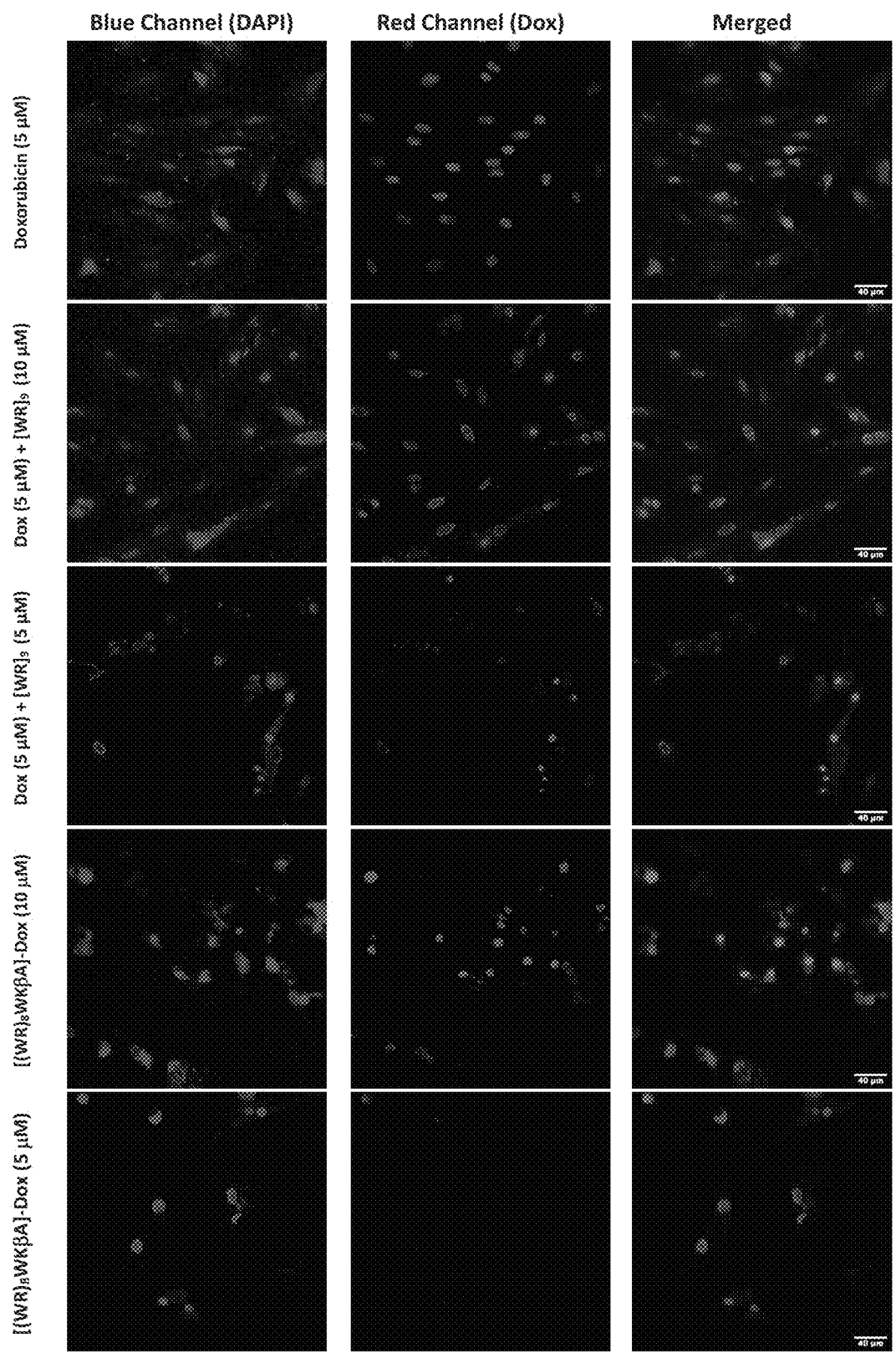
FIG. 30 depicts confocal microscopy images of free Dox (5 µM), [WR]₉+Dox (1:1 and 1:2), or [(WR)₈WKβA]-Dox conjugate (5 and 10 µM) after 24 h in H9C2 cell line.

Cardiotoxicity associated with Dox therapy is well-documented. To investigate the effect of peptide conjugation on Dox cardiotoxicity, rat H9C2 myocardium cells were exposed to [(WR)$_8$WKβA]-Dox conjugate, Dox, and the physical mixture of [WR]$_9$ with Dox for 24 h. The results indicated that no significant cytotoxicity was observed for [(WR)$_8$WKβA]-Dox conjugate at concentrations of 1 μM and 5 μM, while at 10 μM, the cytotoxicity of [(WR)$_8$WKβA]-Dox conjugate was comparable to Dox and the physical mixture of Dox (5 μM) with [WR]$_9$ (10 μM) (FIG. 29). Confocal microscopy also confirmed high uptake of Dox (5 μM) and physical mixture of Dox (5 μM) with [WR]$_9$ (5 μM) or [WR]$_9$ (10 μM) in heart cells, consistent with the cytotoxicity data, while [(WR)$_8$WKβA]-Dox conjugate at 5 μM did not show any significant uptake (FIG. 30).

Cellular Internalization

Figure 23:
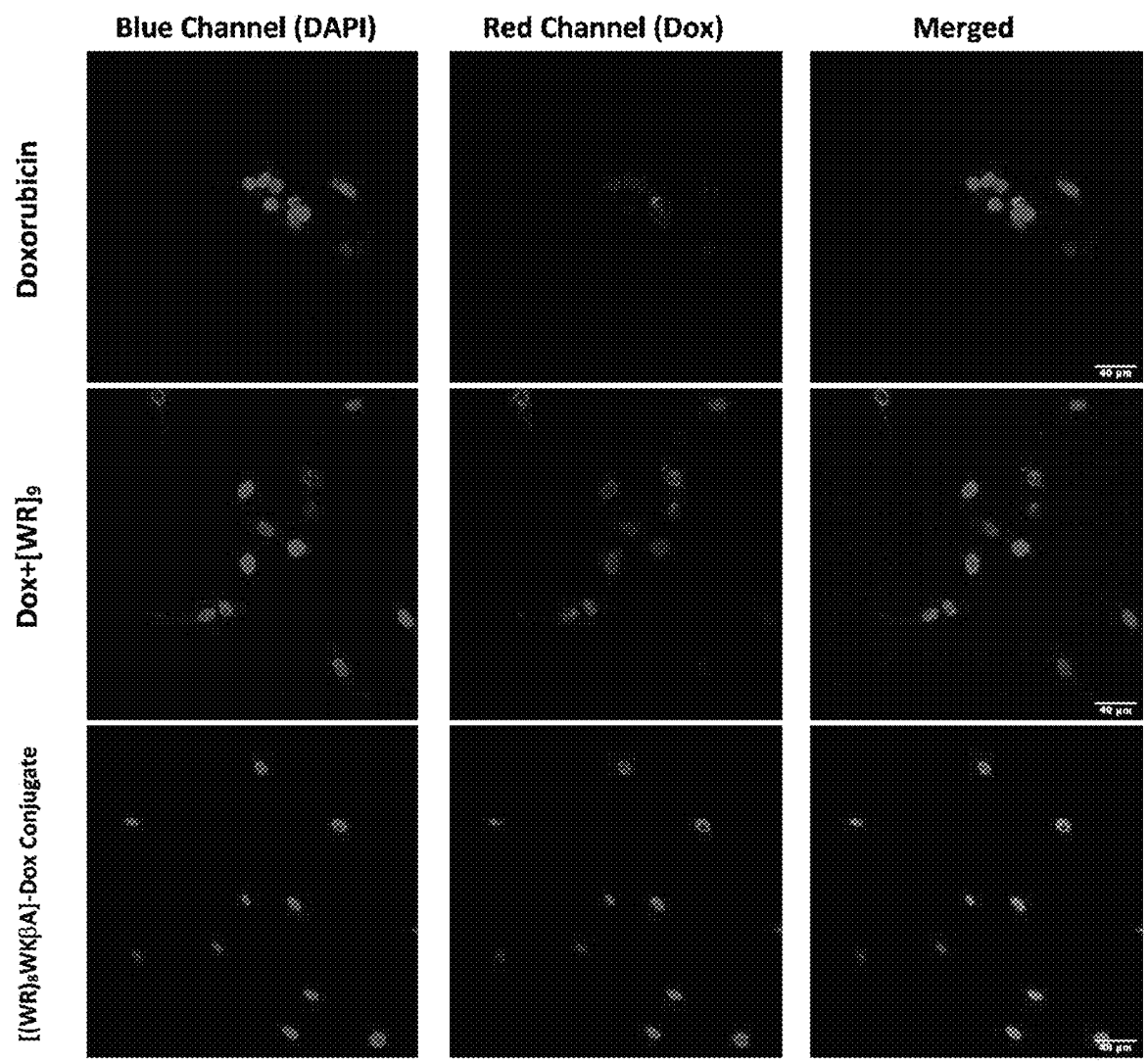
FIG. 23 depicts confocal microscopy images of free Dox (5 µM), [WR]₉+Dox (1:1, (5 µM)) [(WR)₈WKβA]-Dox conjugate (5 µM), or after 24 h in SK-OV-3 cells. Red represents the fluorescence of Dox.

Confocal microscopy was used to evaluate, visualize and confirm the internalization of [(WR)$_8$WKβA]-Dox conjugate vs. free Dox (FIG. 23). The cellular internalization was evaluated in Dox-sensitive/resistant cells to study the effect of overexpression of the MDR efflux proteins on the Dox internalization by the peptide conjugate. Cells were treated with Dox, [(WR)$_8$WKβA]-Dox conjugate, and the physical mixture [WR]$_9$+Dox (1:1) for 24 h, and the nuclei were stained with DAPI. The cellular internalization of all test compounds was examined first in SK-OV-3 cells (FIG. 23). To achieve the primary influx, the cells were incubated with Dox (5 μM), [(WR)$_8$WKβA]-Dox conjugate (5 μM), and [WR]$_9$+Dox (1:1, (5 μM)) for 3 h. This process was followed by 24 h incubation with media to allow the cells to start the efflux process through pumping the compounds out. SK-OV-3 cells have an efflux mechanism for Dox after 24 h that leads to reduced intracellular Dox levels, possibly due to the overexpression of energy-dependent drug efflux pump proteins such as P-gp. The results demonstrated that the covalent conjugation of Dox with [(WR)$_8$WKβA] increased the cellular uptake and retention of Dox as compared with Dox alone (determined by co-localization of the blue signal of the DAPI-stained nuclei and the red signal of Dox). The physical mixture of peptide and free Dox showed less Dox localization compared to the conjugate in SK-OV-3 cells, as shown in FIG. 23. Dox conjugate and the physical mixture showed localization mainly in the nucleus, the main site of action for Dox. The data suggest that [(WR)$_8$WKβA]-Dox conjugate significantly enhanced the retention of Dox in the nucleus versus Dox.

Figure 24A:
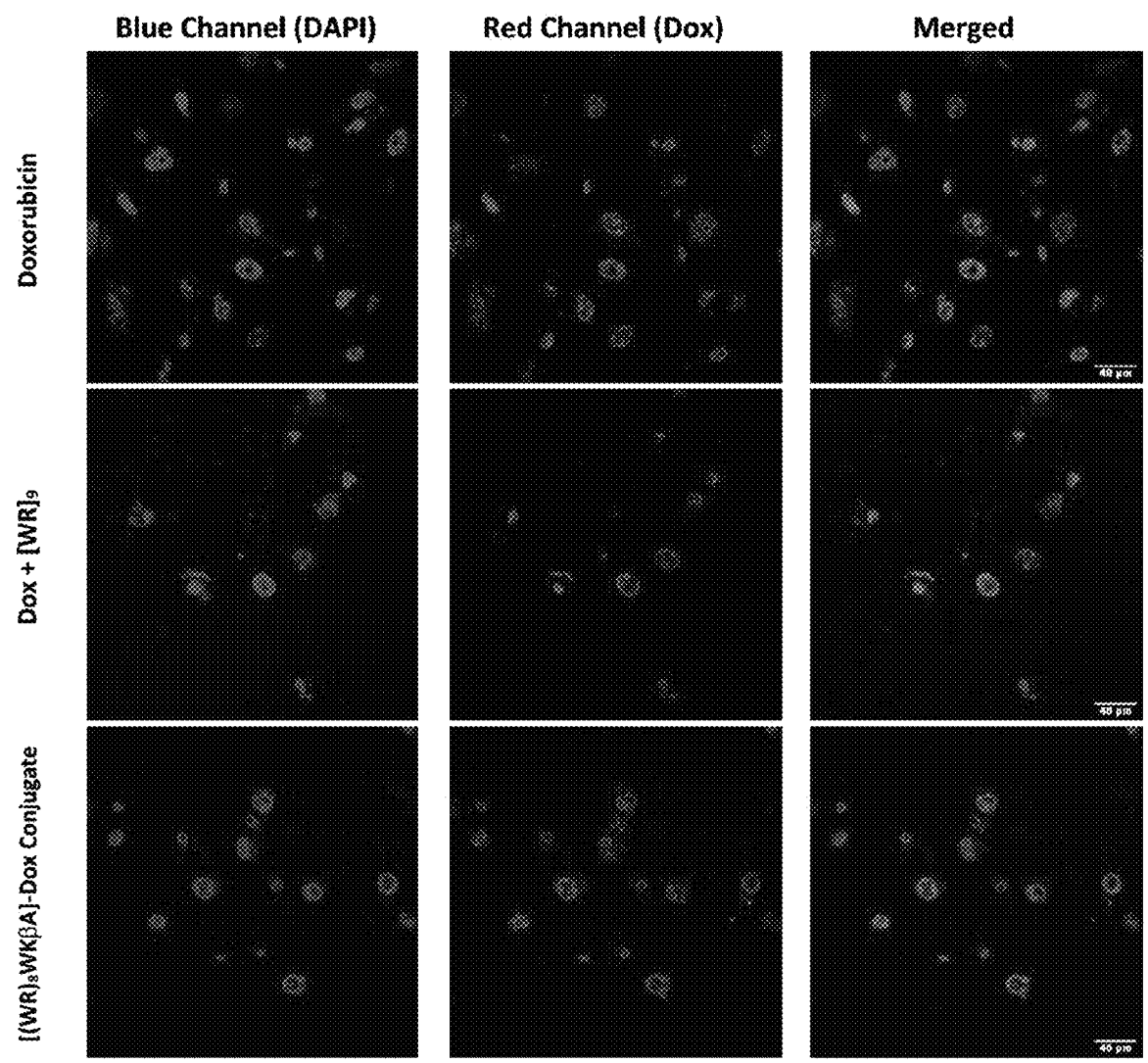
FIGS. 24A-B depict confocal microscopy images of free Dox (5 µM), [WR]₉+Dox (1:1, (5 µM)), or [(WR)₈WKβA]-Dox conjugate (5 µM) after 24 h in MDA-MB-231 (FIG. 24A) and MES-SA/MX2 (FIG. 24B) cells. Red represents the fluorescence of Dox.
Figure 24B:
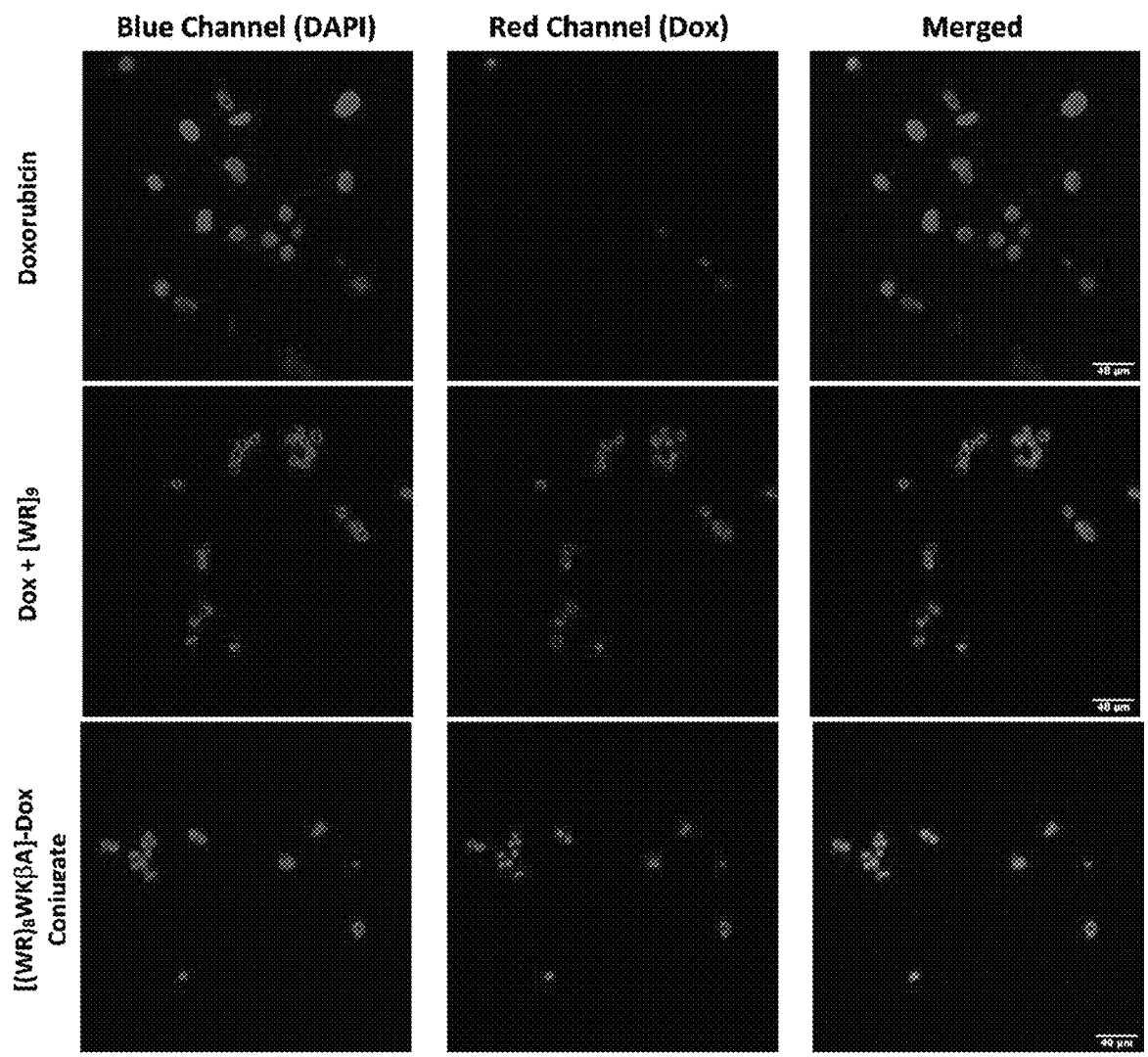

Dox internalization was explored into Dox-resistant cell lines using confocal microscopy (FIG. 24A, B). For this purpose, wild type MDA-MB-231 and MES-SA/MX2 cells were exposed to Dox (5 μM), [(WR)$_8$WKβA]-Dox conjugate (5 μM), or [WR]$_9$+Dox (1:1, (5 μM)) for 24 h, and the nuclei were stained with DAPI. Indeed, the images demonstrated the internalization of free and conjugated Dox in wild type MDA-MB-231 cells, while only [(WR)$_8$WKβA]-Dox conjugate and the physical mixture were internalized into the resistant cell lines overexpressing P-gp, which clearly indicates that this approach can potentially be used to overcome multidrug resistance mechanism in cancer cells, as shown in FIG. 24A, B. These data are consistent with antiproliferative results described above, where [(WR)$_8$WKβA]-Dox conjugate and [WR]$_9$+Dox exhibited significantly higher antiproliferative activity than Dox alone in Dox-resistant MES-SA/MX2 cells.

Figure 25A:
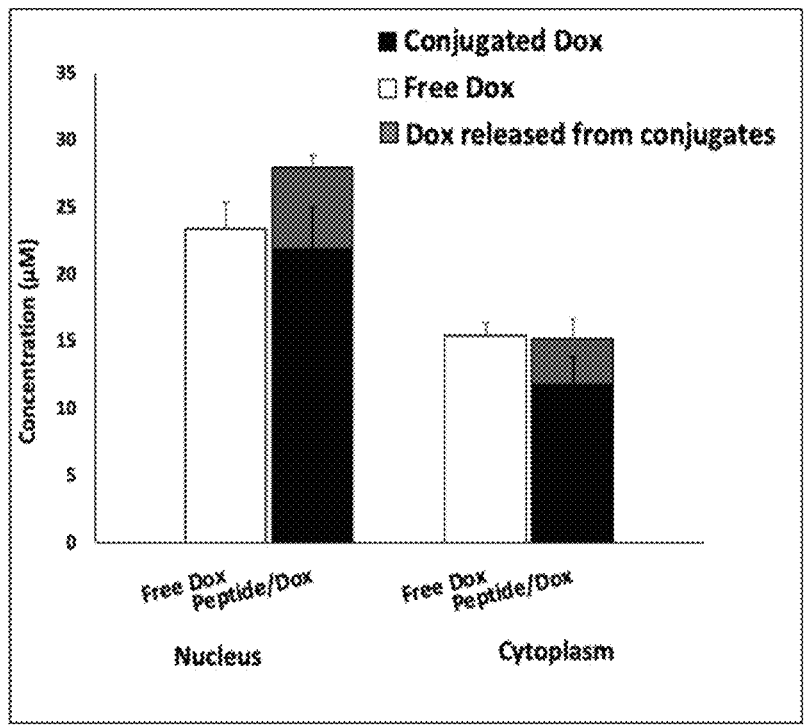
FIGS. 25A-B depict intracellular tracking of Dox in MDA-MB-231 cells revealed efficient nuclear delivery by [(WR)₈WKβA]-Dox via quantification by HPLC (FIG. 25A) in nuclear and cytoplasmic compartments and by confocal microscopy (FIG. 25B).
Figure 25B:
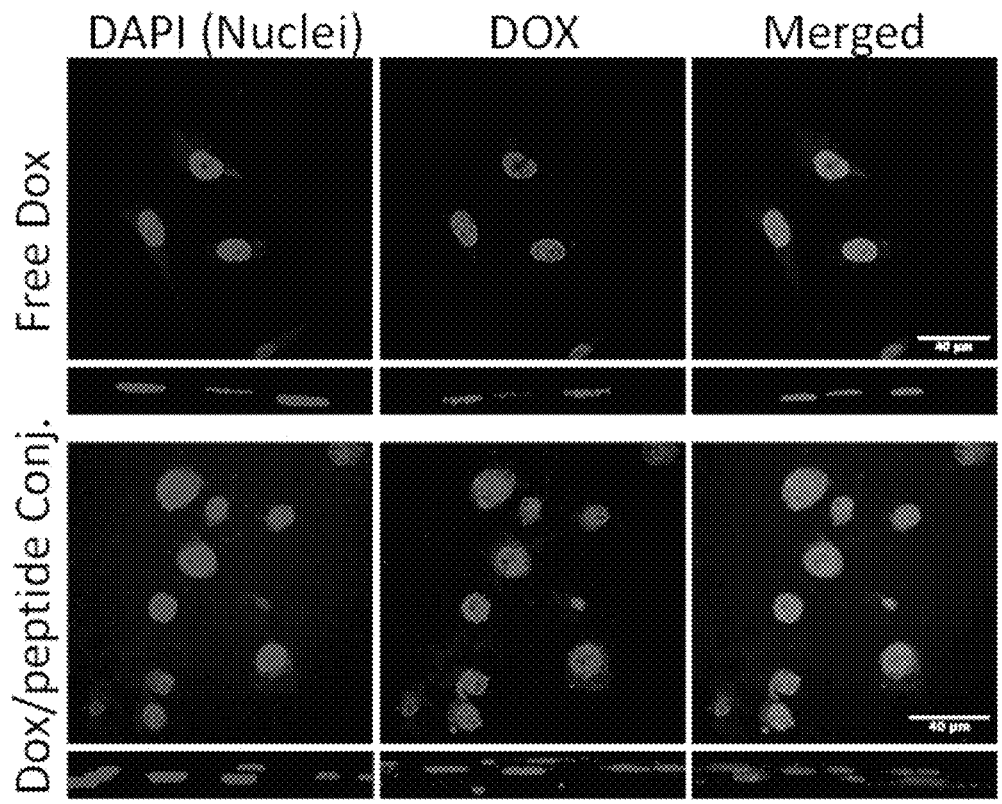

The localization of [(WR)$_8$WKβA]-Dox (50 μM) in cellular compartments was analyzed by isolation of nuclei and cytoplasm and using an HPLC method that differentially quantifies free and peptide-conjugated Dox (FIG. 25A). While free Dox easily diffuses to the nucleus, the total concentration of Dox (conjugated and released) in the nucleus after 4 h exposure to [(WR)$_8$WKβA]-Dox was higher than free Dox. The confocal microscopy images confirm the localization of peptide conjugated Dox in the nuclear compartment (FIG. 25B).

Mechanistic Studies of Cellular Internalization

Generally, cyclic cell-penetrating peptides (CPPs) have different uptake mechanisms depending on the physicochemical properties, the primary and secondary structure, concentration, membrane structure and type of cells, incubation time, and cargo type. Two main mechanisms of permeation through cell membranes have been highly proposed in the literature: direct membrane translocation via energy-independent pathways, and endocytosis pathways, which require energy consumption. Direct translocation occurs due to electrostatic interaction between positively charged residues of CPPs and negatively charged phospholipid bilayer, and is further classified into different models such as the carpet model, pore formation, and the inverted micelle model. Endocytosis, on the other hand, is an energy-dependent and active mechanism composed of various pathways, including phagocytosis and pinocytosis, which are classified into macropinocytosis, clathrin-dependent endocytosis, caveolin-dependent endocytosis, and clathrin- and/or caveolin-independent endocytosis.

Figure 26:
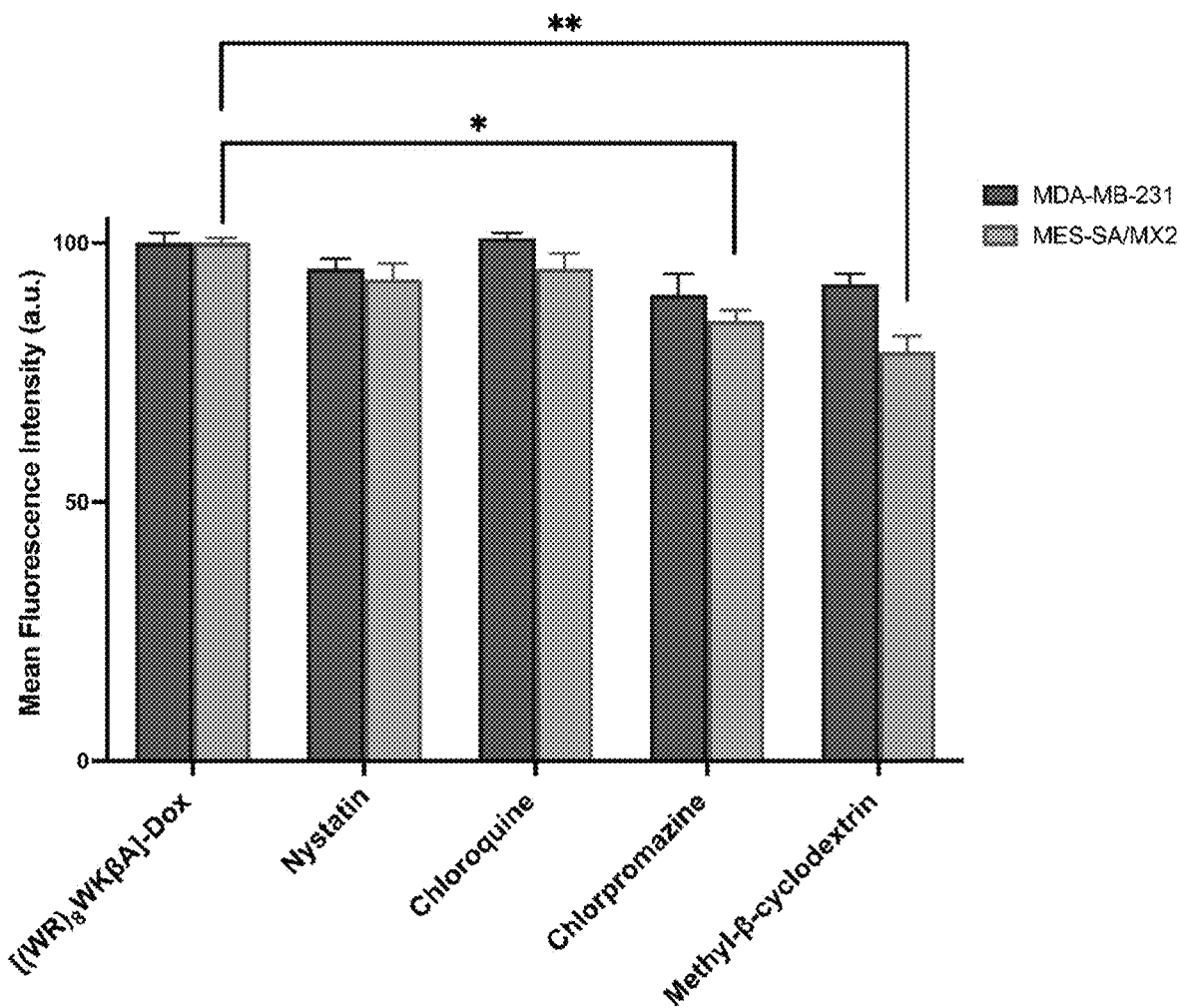
FIG. 26 depicts [(WR)₈WKβA]-Dox conjugate cellular uptake in MDA-MB-231 and MES-SA/MX2 cells in the presence of different inhibitors of clathrin- and caveolae-dependent endocytosis, as studied by flow cytometry. Results are mean±SD (n=3) (* p<0.05, * p<0.01, treatment vs. Ctrl ([(WR)₈WKβA]-Dox conjugate alone).

Thus, flow cytometry and confocal microscopy studies were performed to further explore the mechanism of cellular internalization for [(WR)$_8$WKβA]-Dox conjugate in Dox-sensitive/resistance cells. The cellular internalization of [(WR)$_8$WKβA]-Dox conjugate in MDA-MB-231 and MES-SA/MX2 cells was studied in the presence of endocytosis inhibitors (FIG. 26). Chlorpromazine is a well-known inhibitor of clathrin-mediated endocytosis; methyl-β-cyclodextrin acts as an inhibitor of caveolae-mediated uptake; chloroquine is an antimalaria medication that reduces the expression of phosphatidylinositol binding clathrin assembly protein, and is an inhibitor of endocytosis; and nystatin is a caveolae/lipid raft-dependent endocytosis inhibitor. Cells were incubated with nystatin (50 μg/mL), chloroquine (100 μM), chlorpromazine (30 μM), and methyl-s-cyclodextrin (2.5 mM) for 30 min. The cells were then exposed to free Dox or peptide-Dox conjugate at 5 μM for 3 h.

The cellular uptake of [(WR)$_8$WKβAβ-Dox conjugate (5 μM) in the presence and absence of endocytosis inhibitors was not reduced significantly by nystatin and chloroquine, which inhibit caveolae-mediated endocytosis and clathrin-dependent endocytosis, respectively, in both MDA-MB-231 and Dox-resistant MES-SA/MX2 cell lines. However, a slight uptake reduction was observed in the presence of chlorpromazine and methyl-β-cyclodextrin in Dox sensitive MDA-MB-231 cells, and was statistically significant in Dox resistant MES-SA/MX2, as shown in the flow cytometry data (FIG. 26). None of the endocytosis inhibitors were able to completely stop the cellular uptake of [(WR)$_8$WKβA]-Dox conjugate. As a result, clathrin- and caveolae-mediated endocytosis were excluded as the main mechanism of uptake. These data suggest direct penetration is the main mechanism involved in the internalization of [(WR)$_8$WKβA]-Dox conjugate across the cell membrane, and that most of the uptake occurs through an endocytosis-independent manner.

Figure 27A:
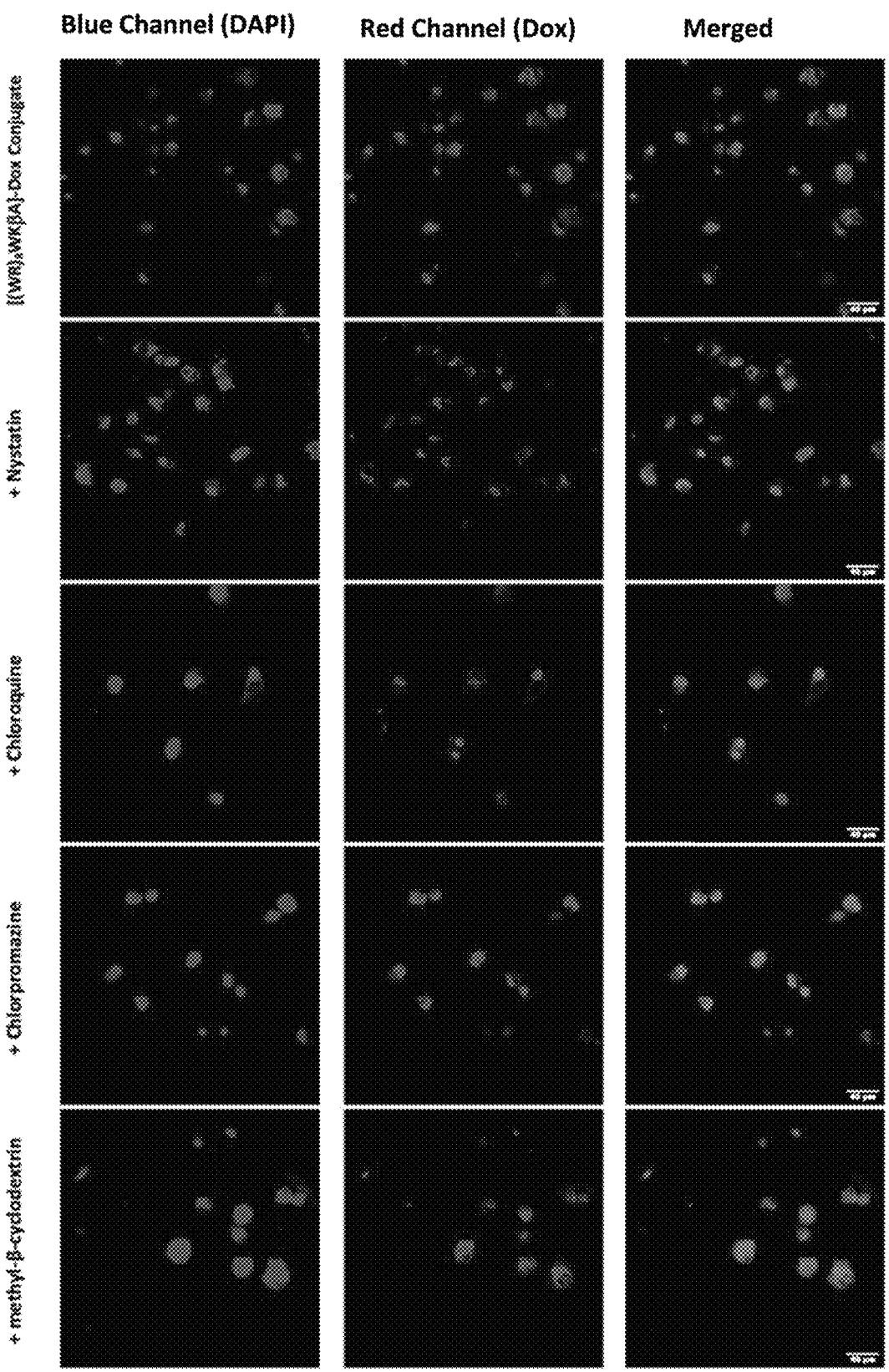
FIGS. 27A-B depict [(WR)₈WKβA]-Dox conjugate (10 µM) cellular uptake in MDA-MB-231 (FIG. 27A) cells and MES-SA/MX2 (FIG. 27B) cells in the presence of different inhibitors of clathrin- and caveolae-dependent endocytosis, as studied by confocal microscopy.
Figure 27B:
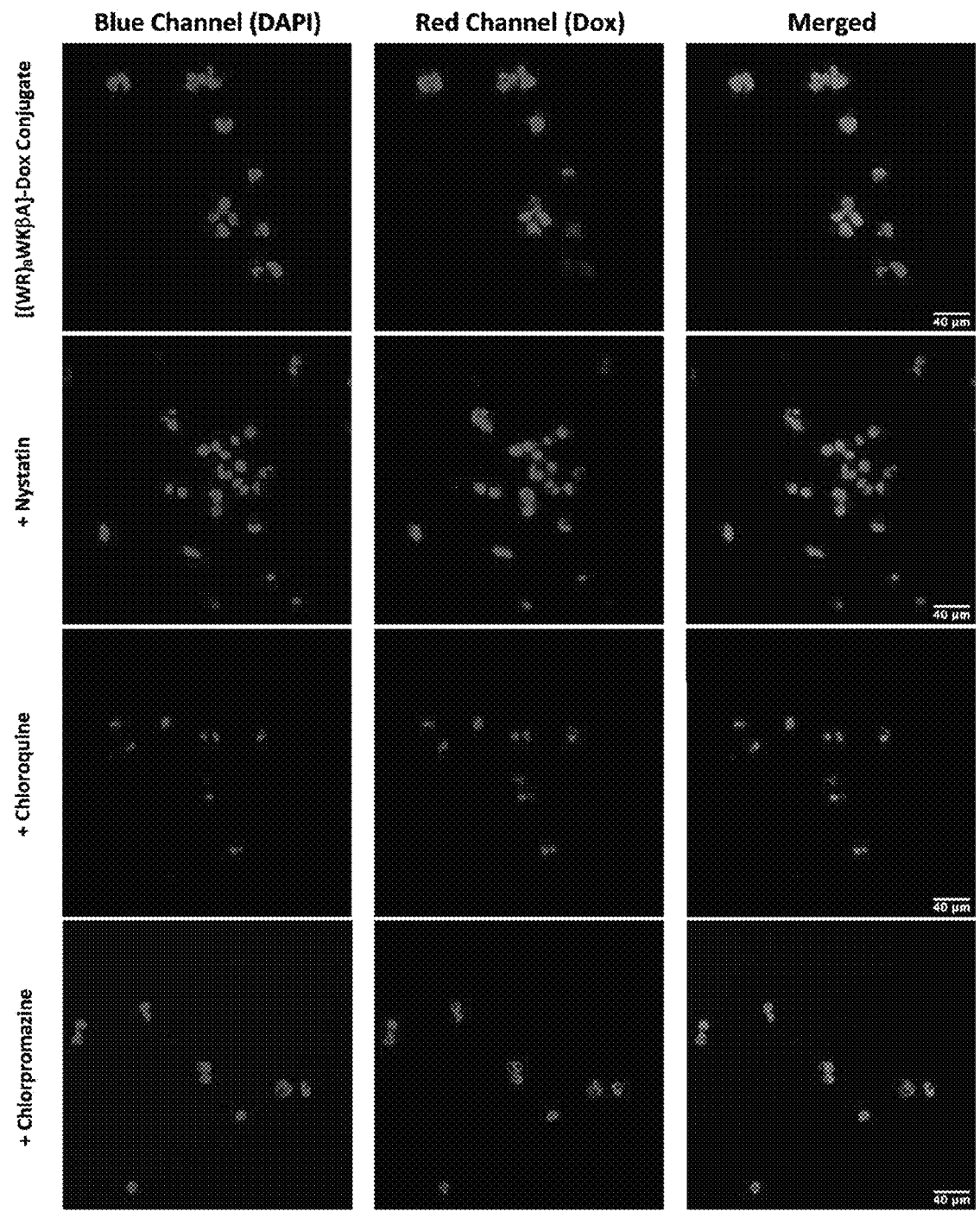

Dox internalization was explored in MDA-MB-231 and MES-SA/MX2 cells in the presence and absence of endocytosis inhibitors using confocal microscopy. The confocal microscopy (FIGS. 27A and B) images demonstrate the localization of the conjugate in the nucleus, with no change in the uptake in the presence of chloroquine, chlorpromazine, nystatin, and methyl-s-cyclodextrin. These data are consistent with the flow cytometry findings.

Drug Release and Plasma Stability of [(WR)$_8$WKβA]-Dox Conjugate

Figure 28A:
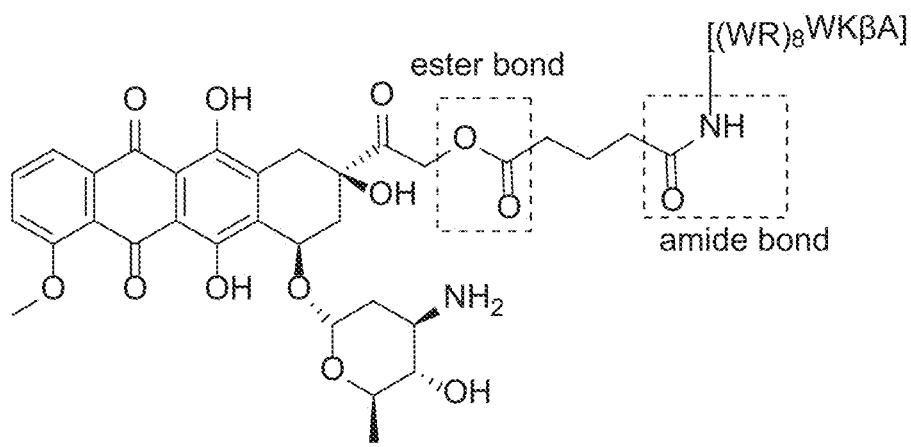
FIGS. 28A-C.

In addition to enhanced efficacy, the designing peptide-drug conjugate should be adequately stable to reach the target and release Dox intracellularly. The linker between the carrier peptide and cytotoxic drug is important. An ideal linker would maintain stability in the systemic circulation while allowing the drug to be released only after intracellular uptake of the conjugate by the cancer cells. In [(WR)$_8$WKβA]-Dox conjugate, an ester bond is utilized to attach Dox with a glutaryl linker, which is further attached to the peptide via an amide bond (FIG. 28A). Ester and amide bonds are known to be susceptible to esterases and amidases, respectively, abundantly found in plasma and intracellular compartments such as the endosomes and lysosomes of cancer cells.

Figure 28B:
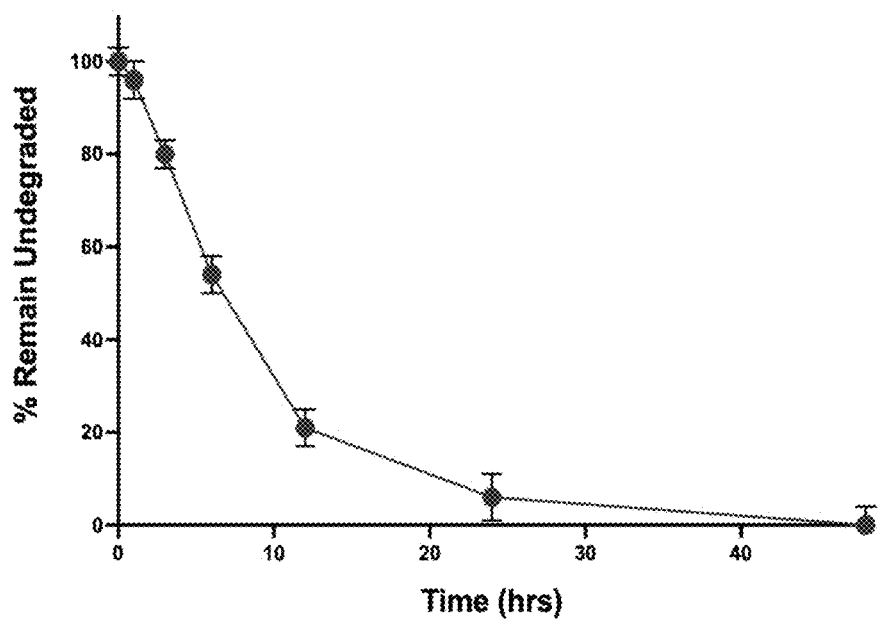
Figure 28C:
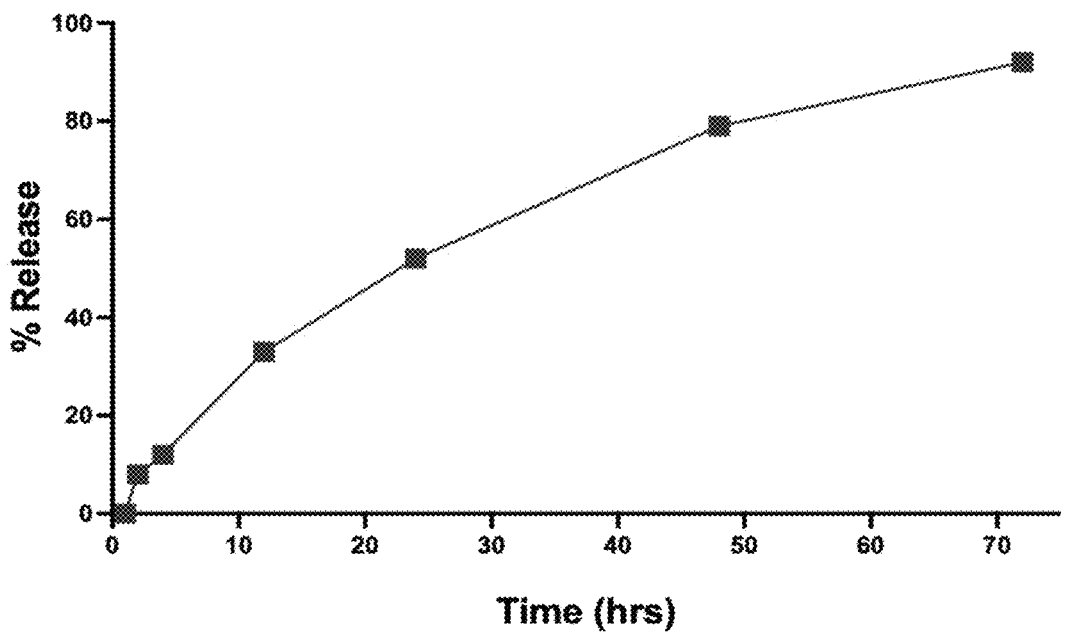

Thus, to determine the fate of the conjugate, a stability study mimicking the physiological environment using the human serum was conducted. Data are represented in the form of the percentage remaining of undegraded peptide-Dox conjugate against time by measuring area under the curve in analytical HPLC chromatogram (FIG. 28B). [(WR)$_8$ WKβA]-Dox conjugate (5 μM) showed only 7% degradation after 1 h incubation with human plasma. However, 80% intact conjugate was observed at the 3 h time point. At 6 h, approximately 50% of the conjugate has been digested by enzymes present in human plasma. Half-life ($t_{1/2}$) for [(WR)$_8$WKβA]-Dox conjugate was (approximately 6 h), and only 6% of the conjugate was still intact at 24 h. The intact conjugate could remain stable enough to reach the target within 1-2 h.

In the same context, a cellular hydrolysis study was conducted to measure the release of free Dox in the cancer microenvironment. Intracellular hydrolysis for [(WR)$_8$WKβA]-Dox conjugate was monitored in leukemia CCRF-CEM cells. The cells (1.37×10$^7$) were first incubated with the conjugate (5 μM) for 4 h. Then, the incubation was continued with drug-free medium to determine the possibility of intracellular hydrolysis to free Dox. Data are represented in the form of percentage release of free Dox against time by measuring the area under the curve (AUC) in analytical HPLC chromatograms (FIG. 30). The cellular hydrolysis data exhibit that the [(WR)$_8$WKβA]-Dox conjugate was hydrolyzed intracellularly and released Dox in a time-dependent manner. More than 36% of free Dox was released intracellularly within 12 h. Approximately 100% of Dox was released from the conjugate intracellularly within 72 h (FIG. 30C). These data suggest that the uptake, retention, and sustained intracellular hydrolysis of [(WR)$_8$WKβA]-Dox conjugate to free Dox contribute to the overall activity of the conjugate as a potential prodrug.

Conclusions

In this study, [(WR)$_8$WKβA]-Dox conjugate was studied as a prodrug and evaluated against various cancer cell lines, including TNBC and Dox-resistant cells, in comparison to the free drug and the corresponding physical mixtures. The peptide-Dox conjugate demonstrated superior antiproliferative activity when compared with free Dox. The conjugate inhibited the cell proliferation of ovarian adenocarcinoma (SK-OV-3) by 59%, and the TNBC cells MB-MDA-231 and MCF-7 by 71% and 77%, respectively, at a concentration of 5 μM after 72 h of incubation. In contrast, Dox inhibited the proliferation of SK-OV-3, MDA-231, and MCF-7 by 35%, 63%, and 57%, respectively. Furthermore, [(WR)$_8$WKβA]-Dox conjugate significantly reduced antiproliferative activity against Dox-resistant cells (MES-SA/MX2), by 92% when compared with free Dox, which decreased proliferation by only 15% at 5 μM. Confocal microscopy experiments and cellular uptake studies confirmed the antiproliferative results, demonstrating the internalization of the conjugate in TNBC and Dox-resistant cells. The cellular uptake was found to be mostly through an endocytosis-independent pathway. These data indicate that the conjugate has potential as a peptide-based prodrug in Dox-resistant cells Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of the invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the invention may be utilized in accordance with the teachings herein. Accordingly, the invention is not limited to that precisely as shown and described.

What is claimed is:
1. A drug delivery system comprising a peptide targeting agent conjugated to a pharmaceutical agent,
wherein the peptide targeting agent is a cyclic or hybrid cyclic linear peptide comprising tryptophan (W), arginine (R), and lysine (K) residues; and wherein the peptide targeting agent comprises,
(2)
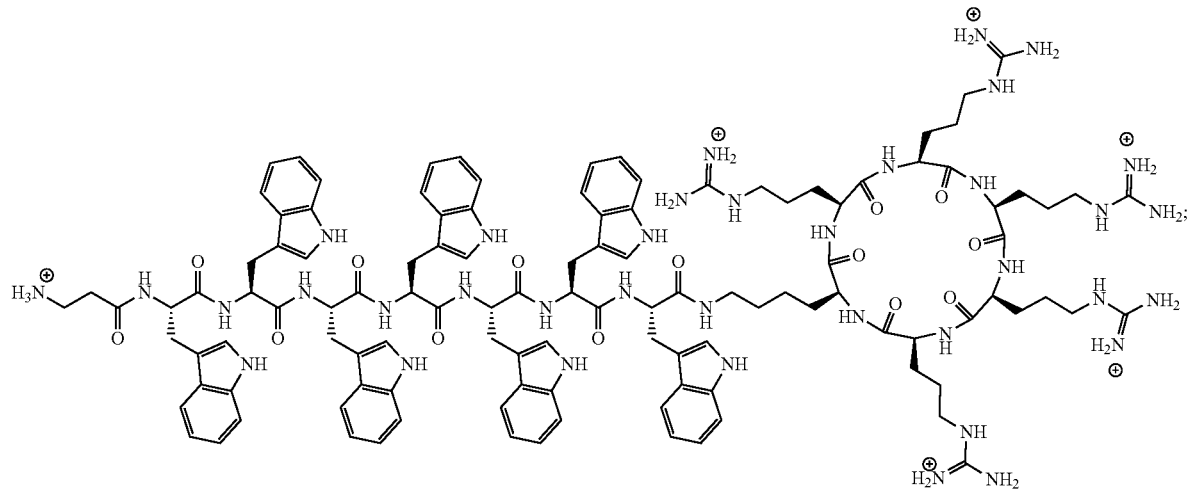
cyclic-linear [R₅K]W₇A
(3)
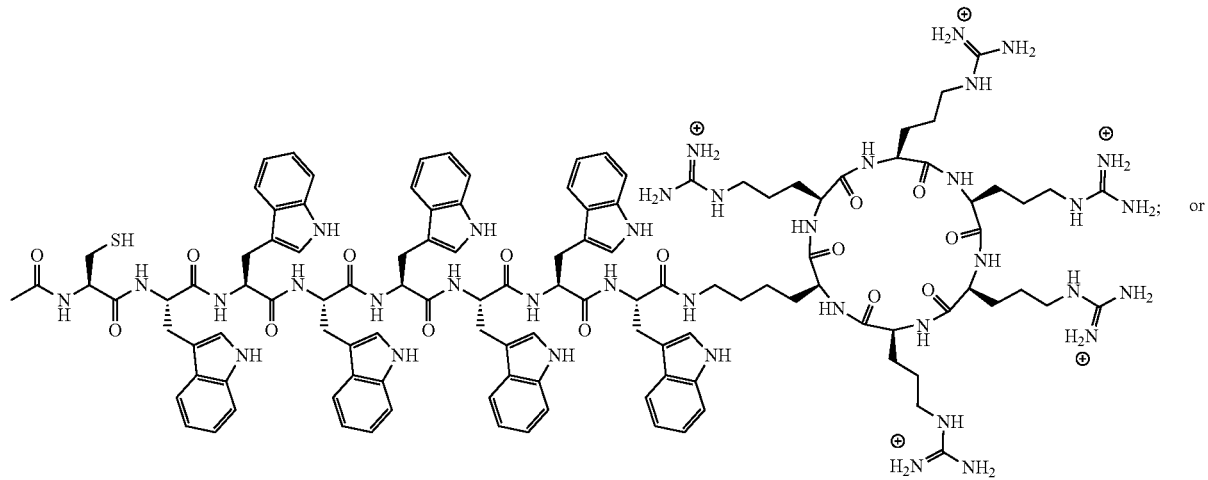
Cyclic-Linear [R₅K]W₇C
or

-continued

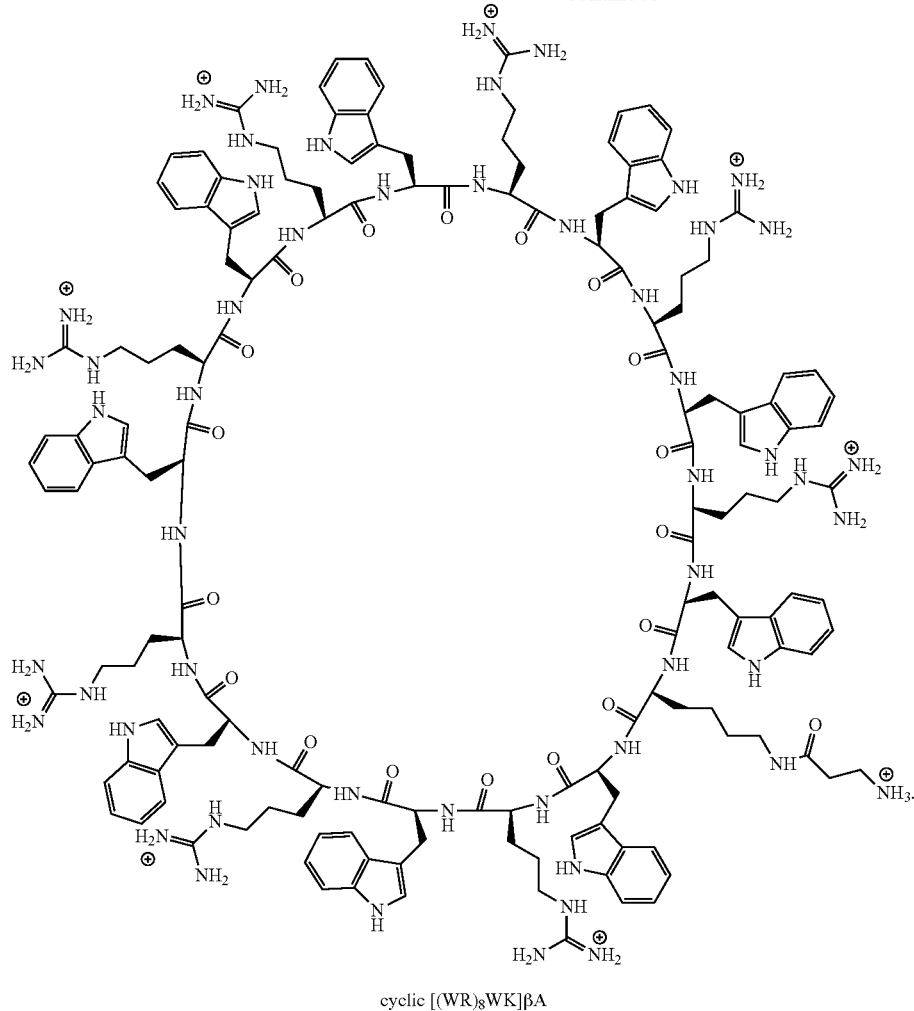

cyclic [(WR)₈WK]βA

2. The drug delivery system of claim 1, wherein the peptide targeting agent comprises cyclic-linear [R₅K]W₇A.

3. The drug delivery system of claim 1, wherein the peptide targeting agent comprises cyclic-linear [R₅K]W₇C.

4. The drug delivery system of claim 1, wherein the peptide targeting agent comprises cyclic [(WR)₈WK]βA.

5. The drug delivery system of claim 1, wherein the pharmaceutical agent is selected from the group consisting of altretamine, bendamustine, busulfan, carboplatin, carmustine, chlorambucil, cisplatin, cyclophosphamide, dacarbazine, ifosfamide, lomustine, mechlorethamine, melphalan, oxaliplatin, temozolomide, thiotepa, trabectedin, streptozocin, azacitidine, 5-fluorouracil, 6-mercaptopurine, capecitabine, cladribine, clofarabine, cytarabine, decitabine, floxuridine, fludarabine, gemcitabine, hydroxyurea, methotrexate, nelarabine, pemetrexed, pentostatin, pralatrexate, thioguanine, trifluridine, tipiracil, daunorubicin, doxorubicin, epirubicin, idarubicin, valrubicin, bleomycin, dactinomycin, mitomycin-c, mitoxantrone, irinotecan, topotecan, etoposide, mitoxantrone, teniposide, cabazitaxel, docetaxel, nab-paclitaxel, paclitaxel, vinblastine, vincristine, vinorelbine, all-trans-retinoic acid, arsenic trioxide, asparaginase, eribulin, hydroxyurea, ixabepilone, mitotane, omacetaxine, pegaspargase, procarbazine, romidepsin, vorinostat, and any combination thereof.

6. The drug delivery system of claim 5, wherein the chemotherapeutic drug is doxorubicin.

\* \* \* \* \*